United States Patent
Mukerji et al.

(10) Patent No.: US 7,208,590 B2
(45) Date of Patent: Apr. 24, 2007

(54) GENES INVOLVED IN POLYKETIDE SYNTHASE PATHWAYS AND USES THEREOF

(75) Inventors: Pradip Mukerji, Columbus, OH (US); Suzette L. Pereira, Westerville, OH (US)

(73) Assignee: Abbott Laboratories, Abbott Park, IL (US)

( * ) Notice: Subject to any disclaimer, the term of this patent is extended or adjusted under 35 U.S.C. 154(b) by 444 days.

(21) Appl. No.: 10/619,532

(22) Filed: Jul. 15, 2003

(65) Prior Publication Data

US 2005/0014231 A1    Jan. 20, 2005

(51) Int. Cl.
  C12N 15/52    (2006.01)
  C12N 9/00     (2006.01)
  C12N 15/74    (2006.01)
  C12N 15/79    (2006.01)
  C12P 7/64     (2006.01)

(52) U.S. Cl. ............... 536/23.2; 435/41; 435/69.1; 435/252.3; 435/320.1

(58) Field of Classification Search ............... None
See application file for complete search history.

(56) References Cited

U.S. PATENT DOCUMENTS 6,140,486 A    10/2000  Facciotti et al.
6,566,583 B1    5/2003  Facciotti et al.
2002/0194641 A1  12/2002  Metz et al.
2004/0235127 A1* 11/2004  Metz et al. .......... 435/183

OTHER PUBLICATIONS

Allen, E.E., et al., "Monounsaturated but Not Polyunsaturated Fatty Acids Are Required for Growth of the Deep-Sea Bacterium *Photobacterium profundum* SS9 at High Pressure and Low Temperature", *Appl. And Env. Microbiol.*, 65(4):1710-1720 (1999).

Kendrick, A. & Ratledge, C., "Lipids of Selected Molds Grown for Production of n-3 and n-6 Polyunsaturated Fatty Acids", *LIPIDS*, 27(1):15-20 (1992).

Knutzon, D.S., et al., "Identification of $\Delta 5$-Desaturase from *Mortierella alpina* by Heterologous Expression in Bakers' Yeast and Canola", *J. Biol. Chem.*, 273(45):29360-29366 (1998).

Huang, Y-S., et al., "Cloning of $\Delta 12$- and $\Delta 6$-Desaturases from *Mortierella alpina* and Recombinant Production of γ-Linolenic Acid in *Saccharomyces cerevisiae*", *Lipids*, 34(7):649-659 (1999).

(Continued)

*Primary Examiner*—Nashaat T. Nashed
*Assistant Examiner*—William W. Moore
(74) *Attorney, Agent, or Firm*—Cheryl L. Becker

(57) ABSTRACT

The subject invention relates to isolated nucleic acid sequences or genes involved in polyketide synthase (PKS) biosynthetic pathways. In particular, such pathways are involved in the production of polyunsaturated fatty acids (PUFAs) such as, for example, Eicosapentaenoic acid (EPA) and Docosahexaenoic acid (DHA). Specifically, the invention relates to isolating nucleic acid sequences encoding proteins involved in eukaryotic PUFA-PKS systems and to uses of these genes and encoded proteins in PUFA-PKS systems, in heterologous hosts, for the production of PUFAs such as EPA and DHA.

13 Claims, 25 Drawing Sheets

Organization of PUFA-PKS genes from *Thraustochytrium aureum* ATCC 34304

KS=β-keto acyl synthase
MAT=MalonylCoA transferase
ACP=Acyl carrier protein
KR=Ketoacyl-ACP reductase
AT=Acyl transferase

OTHER PUBLICATIONS

Metz, J.G., "Production of Polyunsaturated Fatty Acids by Polyketide Synthases in Both Prokaryotes and Eukaryotes", *Science*, 293:290-293 (2001).

Morita, N., et al., "Cloning and sequencing of clustered genes involved in fatty acid biosynthesis from the docosahexaenoic acid-producting bacterium, *Vibrio marinus* strain MP-1", *Biotechnology Letters*, 21:641-646 (1999).

Parker-Barnes, J. M., et al., "Identification and characterization of an enzyme involved in the elongation of n-6 and n-3 polyunsaturated fatty acids", *PNAS*, 97(15):8284-8289 (2000).

Qiu, X., et al., "Identification of a $\Delta 4$ Fatty Acid Desaturase from *Thraustochytrium* sp. Involved in the Biosynthesis of Docosahexanoic Acid by Heterologous Expression in *Saccharomyces cerevisiae* and *Brassica juncea*", *J. Biol. Chem.*, 276(34):31561-31566 (2001).

Tanaka, M., et al., "Isolation of clustered genes that are notably homologous to the eicosapentaenoic acid biosynthesis gene cluster from the docosahexaenoic acid-producing bacterium *Vibrio marinus* strain MP-1", *Biotechnol. Ltrs.*, 21:939-945 (1999).

Watanabe, K., et al., "Fatty Acid Synthesis of an Eicosapentaenoic Acid-Producing Bacterium: *De Novo* Synthesis, Chain Elongation, and Desaturation Systems", *J. Biochem.*, 122(2):467-473 (1997).

Yazawa, K., "Production of Eicosapentaenoic Acid from Marine Bacteria", *Lipids*, 31(Suppl):S297-S300 (1996).

\* cited by examiner

Comparison of the predicted amino acid sequence of the *T. aureum* probe 'TA-PKS-1-consensus' and the homologous region on ORF A of *Schizochytrium* PKS gene cluster (Accession number AAK72879).

Quality:        1269          Length:   525
Ratio:          2.469         Gaps:     10
Percent Similarity: 61.690    Percent Identity: 52.849

```
       Match display thresholds for the alignment(s):
                  | = IDENTITY
                  : = 2
                  . = 1

TA-PKS-1-consensus.pep x aak72879.genpept..

1 LCKTLDLEWPH..VFARSIDIELGANEETAAQAIFEELSCPDLTVREAGY  48
     ||||: |||    ||.| :||  | . | || ||  |:.| |: :|| |
2277 LCKTIGLEWSESDVFSRGVDIAQGMHPEDAAVAIVREMACADIRIREVGI 2326

49 TKDGKRWTTEARPVGLGKPKQALRSSDVFLVSGGARGITPVCVRELAKSI  98
     ..|  |  | . | |..:   ||  ||||||||||.|:||: : |
2327 GANQQRCTIRAAKLETGNPQRQIAKDDVLLVSGGARGITPLCIREITRQI 2376

99 SGGTFVLLGRSPL.ADDPAWACGV.EEANIGTAAMAHLKAEFAAGRGPKP 146
     .|| ::|||||  . |  :|||  |:  :|   :    ||   |. |||  |||
2377 AGGKYILLGRSKVSASEPAWCAGITDEKAVQKAATQELKRAFSAGEGPKP 2426

147 TPKAHKALVGSVLGAREVLGSLESIRAQGARAEYVSCDVSCAERVKAVVD 196
     ||:|   |||||||||||| .| | | :| | |||.| | |
2427 TPRAVTKLVGSVLGAREVRSSIAAIEALGGKAIYSSCDVNSAADVAKAVR 2476

197 DLERRVGA.VTGVVHASGVLRDKSVERLELADFEVVYGTKVDGLLNLLQA 245
     | | ..|| |.|:||||||||||: :|:    :|: |:|||| || ||| |
2477 DAESQLGARVSGIVHASGVLRDRLIEKKLPDEFDAVFGTKVTGLENLLAA 2526

246 VDRPKLRHLVLFSSLAGFHGNTGQAVYAMANEALNKMAFHLETAMPGLSV 295
     |||  |:|:||||||||||||||| ||. ||||||||||    || |   .||
2527 VDRANLKHMVLFSSLAGFHGNVGQSDYAMANEALNKMG..LELA.KDVSV 2573

296 KTIGFGPWDGGMVNDALKAHFASMGVQIIPLDGGAETVSRIIGACSPTQV 345
```

FIG.1A

```
      |.| |||||||||   ||  |  |||||||  :|||:||.||:    || ::
2574 KSICFGPWDGGMVTPQLKKQFQEMGVQIIPREGGADTVARIVLGSSPAEI 2623

346 LVGNWGLPPVVPNASVHKITVRLGGESANPFLSSHTIQGRKVLPMTXALG 395
     |||||  |      .   :   ::  .| ||||  | ||||:||||| |:|
2624 LVGNWRTPSKKVGSDTITLHRKISAKS.NPFLEDHVIQGRRVLPMTLAIG 2672

396 LLAEAARGLYVGHQVXGIEDAQVFQGVVLDKGATCEVQLRRESSTASPSE 445
     |||  ||: |: .  |:|||.|.|| .|   |||  |    |||
2673 SLAETCLGLFPGYSLWAIDDAQLFKGVTVDGDVNCEVTL..TPSTAPSGR 2720

446 VVLSASLNVFAAGKVVPAYRAHVVIGASGPRTGGVQLELKDLGVDADPAC 495
     | . |.|  |..||.||||||  :||    |   ::   |  |||||
2721 VNVQATLKTFSSGKLVPAYRAVIVLSNQGAPPANATMQPPSL..DADPAL 2768

496 SVGKGALYDGRTLFHGPAFQYMDEV 520
      .|..|||:||||||||. .|:|
2769 ...QGSVYDGKTLFHGPAFRGIDDV 2790
```

FIG.1B

Comparison of the predicted amino acid sequence of the *T. aureum* probe
'TA-PKS-1-consensus' and the homologous region on ORF 5 of *Shewanella* PKS
gene cluster (Accession number AAB81123).

Quality:      641                 Length:   551
Ratio:        1.233               Gaps:     16
Percent Similarity: 47.379        Percent Identity: 39.919

Match display thresholds for the alignment(s):
            | = IDENTITY
            : = 2
            . = 1

TA--PKS-1-consensus.pep x aab81123.genpept

```
   1 LCKTLDLEWPHVFARSIDIELGANEETAAQAIFEELSCPDLTVREAGYTK  50
     | |||  ||| || || |.:||    . | || ||      . | | .
2094 LTKTLSHEWPQVFCRALDIATDVDATHLADAITSELFDSQAQLPEVGLSL 2143

51 .DGK..RWTTEARPVGLGKPKQALRSSDVFLVSGGARGITPVCVRELAKS  97
     |||   | |  |         |  | |.| ||.|||:|:|   | || |
2144 IDGKVNRVTLVAAEAADKTAKAELNSTDKILVTGGAKGVTFECALALA.S 2192

98 ISGGTFVLLGRSPLADDPAWACGVEEANIGTAAMAHLKAEFAAGRGPKPT 147
     |   |:| ||| |   |.|| |  :  . .||.||:        | |||
2193 RSQSHFILAGRSELQALPSWAEGKQTSELKSAAIAHI.....ISTGQKPT 2237

148 PKAHKALVGSVLGAREVLGSLESIRAQGARAEYVSCDVSCAERVKAVVDD 197
     || .| |  | . |: .| .   || |||||| ||.. . : |
2238 PKQVEAAVWPVQSSIEINAALAAFNKVGASAEYVSMDVTDSAAITAA... 2284

198 LERRVGAVTGVVHASGVLRDKSVERLELADFEVVYGTKVDGLLNLLQAVD 247
     | |  :||.:| .||| || ::    ||:   ||||||.|| || |.:
2285 LNGRSNEITGLIHGAGVLADKHIQDKTLAELAKVYGTKVNGLKALLAALE 2334

248 RPKLRHLVLFSSLAGFHGNTGQAVYAMANEALNKMAFHLETAMPGLSVKT 297
     |::  | :||| |||:|| ||. |||.|: ||| |   |  | .
2335 PSKIKLLAMFSSAAGFYGNIGQSDYAMSNDILNKAALQFTARNPQAKVMS 2384

298 IGFGPWDGGMVNDALKAHFASMGVQIIPLDGGAETVSRIIGACSPTQVLV 347
```

FIG.2A

```
           .||||||||  |||   |   || :|||  |||  . : | .  |.|:
2385 FNWGPWDGGMVNPALKKMFTERGVYVIPLKAGAELFATQLLAETGVQLLI 2434
          .              .              .         .         .         .
 348 G.............NWG..LPPVVPNASVHK.....IT.VRLG 369
          |                   | | |   | |   |    :|  ||
2435 GTSMQGGSDTKATETASVKKLNAGEVLSASHPRAGAQKTPLQAVTATRLL 2484

370 GESANPFLSSHTIQGRKVLPMTXALGLLAEAARGLYVGHQVXGIEDAQVF 419
     || |:  | | |   |||    |:  :  |||  :  .| ||  : | ..
2485 TPSAMVFIEDHRIGGNSVLPTVCAIDWMREAASDM.LGAQVK.VLDYKLL 2532

420 QGVVLDKGATCEVQLRRESSTASPSEVVLSASLNVFAAGKVVPAYRAHVV 469
      .|:| :     |.  |  | .       |  |  |:.     |:  |  |:|  .:
2533 KGIVFETDEPQELTL..ELTPDDSDEATLQALIS..CNGR..PQYKATLI 2576

470 LGASGPRTGGVQLELKDLGVDADPACSVGKGALYDGRTLFHGPAFQYMDE 519
       . :     | :|     . | . |  ||   |||||| | .
2577 SDNADIKQLNKQFDL......SAKAITTAK.ELYSNGTLFHGPRLQGIQS 2619

Organization of PUFA-PKS genes from *Thraustochytrium aureum* ATCC 34304
ORF A-8748 bp
ORF B-6123 bp
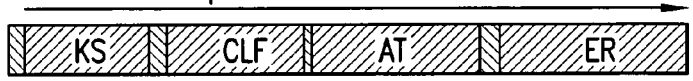
KS=β-keto acyl synthase
MAT=MalonylCoA transferase
ACP=Acyl carrier protein
KR=Ketoacyl-ACP reductase
AT=Acyl transferase
FIG.3

Sequence ID Nos. and Corresponding Sequences:

SEQ ID NO 1:
5'-AGC GGA TAA CAA TTT CAC ACA GG-3'

SEQ ID NO 2:
CACGAGGCCAAGCATTCGAGCAAAGCGCTCAACCAGCAGATCCCAGG
CGGGCGCGCCTGCTTCGTGGGCGTCTCGCGAATCGACGGACAGCTCG
GACTTAGCGGAGCTTGCGCGAAAGGAAAGGGCTGGGCTGAGGCCGCA
GAGATTGCTCAGCAAGGAGCCGTCGCAGGCTTGTGCAAGACCTTGGA
CCTAGAGTGGCCGCACGTCTTCGTCGCAGCATCGACATCGAGCTTGG
CGCGAACGAAGAAACAGCTGCGCAAGCAATCTTTGAGGAGCTCTCTT
GCCCGGACCTAACGGTGCGCGAAGCAGGATACACCAAAGACGGCAA
GCGGTGGACGACTGAGGCGCGACCGGTTGGGCTTGGCAAGCCCAAGC
AGGCACTACGTTCTTCGGACGTCTTCTTGGTTTCTGGTGGGCGCGGGG
AATTACACCTGTTTGCGTTCGCGAGTTGGCCAAATCGATCAGTGGTGG
CACTTTTGTCCTCCTCGGGCGGTCCCCTCTCGCTGATGATCCGGCGTGG
GCTTGCGGCGTCGAGGAAGCAAACATTGGGACAGCCGCTATGGCGCA
CCTCAAGGCCGAGTTCGCAGCCGGGCGCGGCCCGAAGCCGACGCCAA
AGGCCCACAAAGCACTCGTTGGGAGCGTCCTGGGGCGCGCGAAGTC
CTTGGTTCGCTAGAGAGTATTCGCGCCCAGGGTGCGCGCGCCGAGTAC
GT

SEQ ID NO:3:
TCGCCAACACAAGTTCTGGTTGGCAACTGGGGCTTGCCCCCTGTAGTT
CCTAACGCGAGCGTGCACAAGATTACTGTGAGGCTTGGCGGGGAGTC
TGCAAACCCTTTCCTGTCCTCCCACACGATTCAAGGCAGAAAGGTCTT
GCCGATGACTGYGGCGCTTGGGCTTCTCGCTGAGGCGGCTCGAGGGCT
CTACGTCGGTCACCAAGTAGYCGGGATTGAGGACGCCCAAGTCTTCCA
GGGAGTCGTGTTGGACAAAGGGGCGACGTGTGAGGTCCAGCTTCGCC
GCGAGTCTTCGACTGCAAGCCCAAGCGAGGTTGTGCTGAGTGCTTCGC
TCAATGTATTCGCGGCGGGAAAGGTTGTGCCTGCGTACCGCGCGCATG
TCGTGCTCGGCGCTTCAGGGCCACGCACTGGCGGCGTGCAGCTTGAAC
TGAAAGATTTGGGCGTGGACGCCGACCCTGCTTGCTCCGTTGGCAAGG
GTGCGCTGTACGACGGTAGGACGCTGTTCCATGGGCCGGCGTTTCAGT
ACATGGATGAGGTTCCCTGGTGCTCGCCTGCAGAGCTTGCCGTGCGGT
GCCGTGTCGTTCCGAGCGCGGCTCAGGACCGCGGCCAATATGTTTCGC
GCGGAGTGTTGTACGACCCGTTCCTGAACGACACGGTGTTTCAAGCTC
TCCTTGTTTGGGCCCGTCTGGTCAGGGACAGCGCTTCGCTACCGAGCA
ACGTTGAACGAATCTCGTTCCACGGCCAGCCGCCGAGCGAGGGCGAG
GTGTAGTACACCACGCTCAAGCTGGACAGTGCTGCGAGCGGGCCGCT
CGACCCGATTGCAACAGGCGCATTTCTTCCTCCACCGAGCTTGCGGGG
CGGTCTTTGCATCAGGGCGAGCGAGTGTGGTTCTGAACAAGGCTCTTT
CGTATGATGGCTCTCGACCCAAAGGCGAGTAGAGTACTCTACTCAGTA

FIG.4-1

CTCCTTTTCACATACCGGCAGGCAGCGTTGCTGTGGGATGGCCGGGGG
CTCTTCTGCACGCGGCTCC

SEQ ID NO:4:
GAATTCGGCACGAGGCCGGCCTCACGACGCAGGTTGTTCGGTTCCGCG
CTGCAGGTCTGTCACGCAACGCGGACGGCTCTGTTCGAGTCCGCAACC
GCATCATCGGAAAGATTTCGCGCACGGAGCTCGCGGAGATGTTCATTC
GCCCCGCTCCGGAGGCCCTCTTGACCAAGTTGGTTGCGTCGGGTGAGA
TTTCGGCCGAGCAGMNGCCTGGCCAAACAAGTGCCGATGCCGACGAC
ATTGCCGTCGAGSAGAACTCGGGCGGCCACACGGACAATCGCCCGAT
CCATGTCATCCTTCCGCTGATCATCGCGCTCCGCAACAGGCTGCACAA
GGAGTGCGGTTACCCGGCGAGCCTTCGCGTTCGAGTTGGCGCGGGTGG
CGGGATCGGCTGCCCGCTTGCAGCAACTGCGGCCTTCAACATGGGCGC
CGCCTTTCTCGTGACAGGAACAGTCAACCAACTCAGCCGGCAGTCGG
GCACCTGCGACGCGGTGCGCATSAGCTTTTCAAAAGCGACCTACTCGG
ACATCACAATGGCGCCCGCCGCAGATATGTTTGACCAGGGGGTTGAG
CTCCAGGTGCTCAAGAAGGGCACCATGTTTCCGTCGCGCGCCAAGAA
GCTCTACGAGCTGTTTTGCACGTACAACTCGKTCGACGAGATGCCCGC
CGAGGAGCTCGCGCGGGTTGAGAAGCSGATYTTCCAAAAGCCCCTCG
CGGSCGTATGGGACGAGACGAAAGACTTTTACATCAACCGTCTCCACA
ACGAGGACAAGATCGAACGCGCAGAAAAGGATGGCAAGCTCAAGAT
GTCGCTCTCGTTCCGCTGGTACCTTGGCCTGAGTTCGTTCTGGGCCAAC
AATGGAATCGCCGACCGCGTGCTGGACTATCAAGTGTGGTGCGGCCCT
GCGATTGGGGCCTGGAACGACTTTGCCAAGGGATCCTACCTCGACGCC
GAGGTCTGCGGCCAGTTTCCTTGCGTTGTGCAGGTCAACCTGCAGATC
CTCCACGCGCGGCCTACATGCAGCGCCTTCTGGCCGTCAAGCATGACC
CGCGCATCGAGTTTGACCTCGAGGACCCGGTCTTTGGTACGCCCCCAC
TGCCGCGCTCTAAAGCGATGCAGCAACGCACTCTTTCGGAGGCCCGTC
GCTGCAGCACTTGTGCGAACTCGATAGGGTTTCTTTCAAGATTTCAATC
AACAAAACAAGTATTGGAATGACAAAAAAAAAAAAAAAACTCGAG

SEQ ID NO:5:
5'- CTT GTG CAA GAC CTT GGA CCT AGA G-3'

SEQ ID NO:6:
5'-GAA CCT CAT CCA TGT ACT GAA ACG C-3'

SEQ ID NO:7:
TTGTGCAAGA CCTTGGACCT AGAGTGGCCG CACGTCTTCG
CTCGCAGCAT CGACATCGAG CTTGGCGCGA ACGAAGAAAC
AGCTGCGCAA GCAATCTTTG AGGAGCTCTC TTGCCCGGAC
CTAACGGTGC GCGAAGCAGG ATACACCAAAGACGGCAAGC
GGTGGACGAC TGAGGCGCGA CCGGTTGGGC TTGGCAAGCC
CAAGCAGGCA CTACGTTCTT CGGACGTCTT CTTGGTTTCT
GGTGGGGCGC GGGGAATTAC ACCTGTTTGC GTTCGCGAGT

FIG.4-2

TGGCCAAATC GATCAGTGGTGGCACTTTTG TCCTCCTCGG
GCGGTCCCCT CTCGCTGATG ATCCGGCGTGGGCTTGCGGC
GTCGAGGAAG CAAACATTGG ACAGCCGCT ATGGCGCACC
TCAAGGCCGA GTTCGCAGCC GGGCGCGGCC CGAAGCCGAC
GCCAAAGGCCCACAAAGCAC TCGTTGGGAG CGTCCTGGGG
GCGCGCGAAG TCCTTGGTTCGCTAGAGAGT ATTCGCGCCC
AGGGTGCGCG CGCCGAGTAC GTTCCTGCGACGTTTCGTG
TGCGGAGCGC GTCAAGGCCG TCGTCGACGA TCTCGAGCGA
CGGGTCGGGG CTGTAACTGG GGTTGTGCAC GCCTCTGGTG
TTCTCCGAGACAAGTCCGTT GAGCGCTTGG AGCTCGCCGA
CTTCGAGGTC GTGTACGGCACCAAGGTGGA CGGCCTGCTC
AACCTGCTGC AGGCCGTGGA CCGCCCAAACTCCGGCACT
TGGTCCTCTT CAGCTCCCTG GCCGGTTTCC ACGGCAACAC
TGGGCAGGCC GTGTACGCTA TGGCGAATGA GGCGCTGAAC
AAGATGGCCTTCCATTTGGA AACTGCGATG CCTGGCCTCT
CGGTCAAGAC GATCGGGTTTGGACCTTGGG ACGGCGGCAT
GGTCAACGAT GCGCTGAAAG CGCACTTTGCGTCTATGGGC
GTCCAAATTA TTCCGCTCGA CGGYGGCGCG GAGACCGTTT
CCCGAATCAT CGGGGCGTGC TCGCCAACAC AAGTTCTGGT
TGGCAACTGGGGCTTGCCCC CTGTAGTTCC TAACGCGAGC
GTGCACAAGA TTACTGTGAGGCTTGGCGGG GAGTCTGCAA
ACCCTTTCCT GTCCTCCCAC ACGATTCAAGGCAGAAAGGT
CTTGCCGATG ACTGYGGCGC TTGGGCTTCT CGCTGAGGCG
GCTCGAGGGC TCTACGTCGG TCACCAAGTA GYCGGGATTG
AGGACGCCCAAGTCTTCCAG GGAGTCGTGT TGGACAAAGG
GGCGACGTGT GAGGTCCAGCTTCGCCGCGA GTCTTCGACT
GCAAGCCCAA GCGAGGTTGT GCTGAGTGCTTCGCTCAATG
TATTCGCGGC GGGAAAGGTT GTGCCTGCGT ACCGCGCGCA
TGTCGTGCTC GGCGCTTCAG GGCCACGCAC TGGCGGCGTG
CAGCTTGAACTGAAAGATTT GGGCGTGGAC GCCGACCCTG
CTTGCTCCGT TGGCAAGGGTGCGCTGTACG ACGGTAGGAC
GCTGTTCCAT GGGCCGGCGT TCAGTACATGGATGAGGTT C

SEQ ID NO:8:
CGCAAGTGCATCCGGCCATCATTGGGCCATCATTGGGCCATCATTGGT
GTTTTGGGCCGCGCTTTGCGGATCGTCCGGCCGATCAGGTACGAGGCC
ACGAACCTACGTCGTTTGCCGCGCTCAGGCTGGTTGGTTGCACTTGGA
CTCTTCTGTGACCTTTCATCGTGTGCAGGCAAACTCGATTTGCAGACCC
GAGACACGGCGAAGGATCCGTGCTGCAAACGCAAGTGGAGTGCGTCG
AGAGCACCGCCGAGACCAAGAGCCGAGGCAGACAAGGCCAGCAACG
AGATGGAGACAAAGGACGATCGCGTTGCGATCGTGGGCATGTCGGCC
ATACTGCCTTGCGGTGAGTCAGTGCGCGAGTCGTGGGAGGCGATTCGC
GAGGGGCTCGATTGCCTGCAGGACCTGCCTGCGGACCGAGTCGATAT
CACGGCGTACTACGACCCGAACAAGACAACCAAGGACAAGATCTACT
GCAAGCGCGGCGGCTTCATTCCCGAGTATGACTTTGACGCGCGCGAGT

FIG.4-3

```
TCGGCCTCAACATGTTCCAGATGGAGGACTCGGACGCCAACCAAACC
GTGACTTTGCTCAAGGTCAAGGAGGCTCTCGAGGACGCCGGGGTGGA
GCCCTTCACAAAGAAGAAGAAGAACATTGGCTGCGTGCTCGGCATCG
GCGGCGGGCAGAAGGCGAGCCACGAGTTTTACTCCCGACTCAACTAT
GTGGTCGTGGAGAAGGTGCTTCGCAAGATGAACCTCCCCGACGAGGT
TGTCGAGGCCGCCGTCGAAAAGTACAAGGCCAACTTTCCTGAATGGC
GCCTCGACTCGTTCCCTGGGTTCTTGGCAACGTGACCGCCGGGCGGT
GCAGCAACGTCTTCAACATGGAAGGCATGAACTGCGTCGTGGACGCT
GCGTGCGCCAGCTCGCTCATCGCGATCAAGGTTGCCATTGATGAGCTC
CTCCACGGGGACTGCGACACCATGATTGCCGGTGCGACCTGCACCGA
CAACTCGATCGGGATGTACATGGCCTTTTCCAAAACCCCAGTTTTCTCC
ACCGACCAGAGCGTCAAGGCGTACGACGCCAAGACGAAAGGCATGC
TCATCGGCGAAGGCTCGGCCATGGTCGTGCTCAAGCGGTACGCGGAC
GCCGTTCGGGATGGTGATGAGATCCATGCCGTCATCAGGGCATGCGCC
TCGTCCAGCGACGGCAAGGCTGCTGGCATTTACGCACCGACGGTGTCG
GGTCAAGAAGAGGCACTGCGGCGCGCGTACGCCCGAGCTGGCGTGGA
CCCCTCCACCGTCACGCTGGTGGAGGGCCACGGCACTGGCACACCCG
TCGGGGACCGGATTGAGCTGACCGCCTTGCGCAACGTCTTTGACGCAG
CCAACAAAGGCCGCAAGGAAACAGTCGCGGTGGGAAGCATCAAGTC
GCAGATCGGTCACCTGAAGGCCGTGGCCGGCTTTGCCGGTCTCGTCAA
GGTTGTCATGGCCCTCAAGCACAAGACGCTGCCGCAGACCATCAACG
TTCACGACCCGCCCGCACTGCACGACGGCTCGCCCATCCAGGATTCGA
GTCTTTACATCAACACGATGAACCGGCCCTGGTTTACGGCACCTGGCG
TCCCCCGCCGTGCAGGCATCTCTAGCTTTGGGTTTGGCGGCGCCAACT
ACCACGCTGTTCTCGAAGAGGCCGAGCCTGAGCACGCGAAGCCGTAT
CGCATGAACCAAGTTCCAACAACCGGTGCTCTTGCACGCAAGCTCCGCG
TCAGCTCTTGCCTCCATCTGCGACGCTCAGGCCGACGCGCTCCAGGCC
GCCGTCTCGCCCGAAGCCAGCAAGCACGCAGACTACCGCGCCATCGT
AGCGTTCCATGAAGCGTTTAAGCTTCGCGCTGGAGTGCCGGCCGGCCA
TGCTCGAATTGGCTTTGTGTCCGGCAGCGCGGCAGCAACGCTTGCAGT
GCTCCGAGCCGCCTCTGCAAAACTCAAGCAGTCGAGTGCGACGCTCG
AATGGACCCTGCTCCGCGAGGGCGTCACGTACCGCTCCGCCGCGATG
CACACTCCTGGCAGTGTCGCTGCTCTGTTTGCCGGGCAAGGCGCGCAG
TACACGCACATGTTCGCTGACGTTGCCATGAACTGGCCACCGTTTCGA
AGCGCCGTGCAAGAGATGGATGCCGCTCAAGTCACGGCGGCAGCGCC
GAAGCGCCTCAGCGAGGTCCTGTATCCGCGCAAGCCGTACGCTGCAG
AGCCCGAGCAAGACAACAAGGCCATCTCGATGACGATTAACTCGCAA
CCGGCCCTCATGGCCTGCGCTGCTGGGGCGTTTGAGGTGTTTCGTCAA
GCTGGTCTTGCGCCCGACCACGTCGCGGGTCATTCTCTCGGCGAGTTT
GGTGCTTTGCTCGCCGCTGGATGCGCAAGCCGTGAGGAGCTCTTCCGT
CTGGTCTGCAGCAGAGCGAAGGCAATGCAAGACGTTCCCAAGCCAAG
CGAGGGCGTCATGGCAGCTGTCATCGGCCGTGGTGCTGACAAGCTCA
CGCTGCAAGGCGATGGTGCGTGGCTTGCCAACTGCAACTCGCCAAGC
CAAGTGGTCATTTCCGGCGACAAGACTGCTGTCGAGCGTGAATCCAGC
CGGTTGGCAGGCCTTGGCTTCAGGATCATTCCGCTTGCATGCGAAGGC
```

FIG.4-4

```
GCCTTCCATTCACCGCACATGACGGCGGCCCAGGCCACGTTTCAGGCT
GCACTGGACAGCCTCAAGATCTCCACCCCGACGAACGGGGCGCGCCT
GTACAACAACGTTTCCGGAAAGACCTGCCGATCCCTGGGTGAACTCC
GCGACTGCCTGGGCAAGCACATGACAAGTCCTGTGCTCTTCCAGGCAC
AGGTAGAGAACATGTACGCTGCCGGGGCGCGCATTTTCGTGGAGTTTG
GCCCGAAGCAAGTCCTCTCCAAGCTCGTAGGCGAGATTCTCGCCGAC
AAGTCAGACTTTGTGACAGTCGCGGTCAACTCGTCATCGTCCAAGGAC
AGCGACGTGCAACTTCGTGAAGCTGCTGCGAAGCTCGCGGTCCTTGGC
GTCCCGTTGGCGAACTTTGACCCTTGGGAGCTCTGCGACGCGCGGCGT
CTTCGCGAATGCCCGCGATCCAAGACGACGTTGCGCTTGTCTGCAGCG
ACCTACGTGTCGAACAAGACCCTTGCTGCTAGGGAGAAGGTCATGGA
GGACAACTGCGACTTTCTTCGCTCTTTGCCTCCGGTCCAGCAAGCCA
AGAGATGGAGCGAGAAATAGCCAACCTTCGCGCTGAGCTGGAGGCGG
CCCAACGCCAGCTTGACACGGCCAAAACCCAGCTTGCTCGAAAGCAA
GTGCAGGACCCCACCGCTGACCGACAGCGCGATATGATTGCCAAGCA
CCGATCCACACTCGCAGCAATGGTGAAGGAATTCGAGGCTCTGGCAA
GTGGTAGTCCTTGCGCTGTTCCGTTGCGCCTGTGGTGGACACTGCTGT
CGAAGACGTGCCTTTTGCGGACAAGGTCTCGACGCCACCGCCCCAAG
TCACTTCCGCTCCCATCGCCGAGCTCGCGCGCGCCGAGGCCGTCGTCA
TGGAGGTTCTCGCTGCCAAGACTGGCTACGAGGTCGACATGATCGAG
GCCGACATGCTGCTCGACGCCGAGCTCGGCATCGACTCGGTCAAGCG
CATTGAGATCCTGGCAGCTGTCCAGGCCCAGCTCGGGGTCGAGGCCA
AGGACGTCGACGCGCTCAGCCGCACACGAACAGTTGGCGAGGTCGTT
GACGCCATGAAGGCTGAGATCGGCGGGCAAGCGACCAGTGCGCCTTC
GCCGATGGCCCAGCCCCAAGCCTCAGCACCATCACCGTCCCCTACTGC
CTCTGTGCTGCCTAAGCCTGTTGCTTTACCAGCTAGTGTCGATCCCGCC
AAGCTCGCGCGCGCCGAAGCGGTCGTCATGGAGGTTCTCGCCGCCAA
GACTGGCTACGAGGTCGACATGATCGAGGCTGACATGCTGCTCGACG
CCGAGCTCGGCATCGACTCGGTCAAGCGCATTGAGATCCTGGCGGCTG
TCCAAGCTCAGCTCGGGGTCGAGGCCAAGGATGTCGACGCGCTCAGC
CGCACACGCACTGTTGGCGAGGTCGTTGATGCCATGAAGGCTGAGAT
CGGCGGGCAAGCGACCAGCGCACCTGCGTCCGTGGCCCAGCCCCAAG
CCTCAGCACCATCACCGTCCGCAACAACTGCCTCTGTGCTGCCTAAGC
CTGTTGCTGCACCAACTAGCGCCGATCCCGCCAAGCTCGCGCGCGCCG
AAGCCGTCGTCATGGAGGTTCTCGCTGCCAAGACTGGCTACGAGGTCG
ACATGATCGAGGCTGACATGCTGCTCGACGCCGAGCTCGGCATCGACT
CGGTCAAGCGCATTGAGATCCTGGCGGCTGTCCAAGCCCAGCTCGGG
GTCGAGGCCAAGGACGTCGACGCGCTCAGCCGCACACGCACGGTTGG
CGAGGTCGTCGAGGCCATGAAGGCTGAGATCGGCGGGCAAGCGACC
AGTGCACCTGCGTCCGTGGCCCAGCCCCAAATCTCTGTGTCCCCTACG
CCTCTCGCTGCATCTCCTAGTGCCGATCCTGCCAAGCTCGCGCGCGCC
GAAGCCGTCGTCATGGAGGTTCTCGCTGCCAAGACTGGCTACGAGGTC
GACATGATCGAGGCTGACATGCTGCTCGACGCCGAGCTCGGCATCGA
CTCCGTCAAGCGCATCGAGATCCTGGCGGCTGTCCAGGCCCAGCTCGG
GGTCGAGGCCAAGGACGTCGACGCGCTCAGCCGCACACGCACTGTTG
```

FIG.4-5

```
GCGAGGTCGTTGACGCCATGAAGGCTGAGATCGGCGGGCAAGCGACC
AGTGCGCCTGCATCCGTGGCCCAGCCCCAAGCCTCAGCACCGTCGCC
GTCCGCTACTGCCTCTGTGCTGCCTAAGCCTGTTGCTGCACCAACTAGC
GCCGATCCCGCCAAGCTCGCGCGCGCCGAAGCCGTCGTCATGGAGGT
TCTCGCTGCCAAGACTGGCTACGAGGTCGACATGATCGAGGCTGACAT
GCTGCTCGACGCCGAGCTCGGCATCGACTCGGTCAAGCGCATCGAGA
TCCTGGCGGCTGTCCAAGCCCAGCTCGGGGTCGAGGCCAAGGACGTC
GACGCGCTCAGCCGCACACGCACGGTTGGCGAGGTCGTCGAGGCCAT
GAAGGCTGAGATCGGCGGGCAAGCGACCAGTGCACCTGCGTCCATGG
CCCAGCCCCAAATCTCTGTGTCCCCTACGCCTCTCGCTGCATCTCCTAG
TGCCGATCCTGCCAAGCTCGCGCGCGCCGAGGCCGTCGTCATGGAGGT
TCTCGCTGCCAAGACTGGCTACGAGGTCGACATGATCGAGGCCGACA
TGCTGCTCGACGCCGAGCTCGGCATCGACTCGGTCAAGCGCATCGAG
ATCCTGGCGGCTGTCCAAGCTCAGCTCGGGGTCGAGGCCAAGGACGT
CGACGCGCTCAGCCGCACACGCACGGTTGGCGAGGTCGTTGATGCCA
TGAAGGCTGAGATCGGCGGGCAAGCGACCAGTGCGCCTGCATCCGTG
GCCCAGCCCCAAGCCTCAGCACCGTCGCCGTCCGCTACTGCCTCTGCG
CCTGTTACGCCTCTCGCTGCACCAGCTAGTGTCGATCCCGCCAAGCTC
GCGCGCGCCGAAGCCGTCGTCATGGAGGTTCTCGCCGCCAAGACTGG
CTACGAGGTCGACATGATCGAGGCTGACATGCTGCTCGACGCCGAGC
TCGGCATCGACTCCGTCAAGCGGATTGAGATCCTGGCGGCTGTCCAAG
CCCAGCTCGGGGTCGAGGCCAAGGACGTCGACGCGCTCAGCCGCACA
CGCACTGTTGGCGAGGTCGTTGACGCCATGAAGGCTGAGATCGGCGG
GCAAGCGACCAGCGCACCTGCGTCCGTGGCCCAGCCCCAAGCCTCAG
CACCGTCGCCGTCCGCTACTGCCTCTGTGCTGCCTAAGCCTGTTGCTTC
ACCAGCTAGTGTCGATCCCGCCAAGCTCGCGCGCGCCGAAGCGGTCG
TCATGGAGGTTCTCGCTGCCAAGACTGGCTACGAGGTCGACATGATCG
ACGCTGACATGCTGCTCGACGCCGAGCTCGGCATCGACTCCGTCAAGC
GCATCGAGATCCTGGCGGCTGTCCAAGCCCAGCTCGGGGTCGAGGCC
AAGGACGTCGACGCGCTCAGCCGCACACGAACGGTTGGCGAGGTCGT
CGAGGCCATGAAGGCTGAGATCGGGGCAGCAGGTCCAAACGATGCA
CAAGCAGCGTCTGGGCATCTCTTTGGCACGGGATGTGAAGACCTGAG
CCTTTGCTCTGCTTCTGTGGTTGAGATTGCTCGTTGCAGCGAACTAGCT
CTGGAGCGCCCGATGGATCGGCCATTCTTATTGTAAGCGATGGATCA
GCATTGCCGGCGGCTCTGGCTAGTCGACTGGGGTCGTGTGCAGTAATC
CTCACGACCGCAGGCGAGACCGACCAATCTGTGCGCTCGACGAAGCA
CGTTGACATGGAAGGGTGGGCGAGGCAGATCTCGTGCGCGCTCTTG
AAGCAGTAGAGTCTCGATTCGGCGTCCCAGGCGGCGTCGTGGTGCTTG
AGCGCGCCTCAGAAACAGCTAGGGACCAGCTTGGCTTTGCCCTGCTGC
TTGCCAAGCATTCGAGCAAAGCGCTCAACCAGCAGATCCCAGGCGGG
CGCGCCTGCTTCGTGGGCGTCTCGCAATCGACGGAAAGCTCGGACTT
AGCGGAGCTTGCGCGAAAGGAAAGGGCTGGGCTGAGGCCGCAGAGA
TTGCTCAGCAAGGAGCCGTCGCGGGCTTGTGCAAGACCTTGGACCTAG
AGTGGCCGCACGTCTTCGCTCGCAGCATCGACATCGAGCTTGGCGCGA
ACGAAGAAACAGCTGCGCAAGCAATCTTTGAGGAGCTCTCTTGCCCG
```

FIG.4-6

GACCTAACGGTGCGCGAAGCAGGATACACCAAAGACGGCAAGCGGT
GGACGACTGAGGCGCGACCGGTTGGGCTTGGCAAGCCCAAGCAGGCA
CTACGTTCTTCGGACGTCTTCTTGGTTTCTGGTGGGGCGCGGGGAATTA
CACCTGTTTGCGTTCGCGAGTTGGCCAAATCGATCAGTGGTGGCACTTT
TGTCCTCCTCGGGCGGTCCCCTCTCGCTGATGATCCGGCGTGGGCTTGC
GGCGTCGAGGAAGCAAACATTGGGACAGCCGCTATGGCGCACCTCAA
GGCCGAGTTCGCAGCCGGGCGCGGCCCGAAGCCGACGCCAAAGGCC
CACAAAGCACTCGTTGGGAGCGTCCTGGGGCGCGCGAAGTCCTTGG
TTCGCTAGAGAGTATTCGCGCCCAGGGTGCGCGCGCCGAGTACGTTTC
CTGCGACGTTTCGTGTGCGGAGCGCGTCAAGGCCGTCGTCGACGATCT
CGAGCGACGGGTCGGGGCTGTAACTGGGGTTGTGCACGCCTCTGGTGT
TCTCCGAGACAAGTCCGTTGAGCGCTTGGAGCTCGCCGACTTCGAGGT
CGTGTACGGCACCAAGGTGGACGGCCTGCTCAACCTGCTGCAGGCCG
TGGACCGCCCCAAACTCCGGCACTTGGTCCTCTTCAGCTCCCTGGCCG
GTTTCCACGGCAACACTGGGCAGGCCGTGTACGCTATGGCGAATGAG
GCGCTGAACAAGATGGCCTTCCATTTGGAAACTGCGATGCCTGGCCTC
TCGGTCAAGACGATCGGGTTTGGACCTTGGGACGGCGGCATGGTCAA
CGATGCGCTGAAAGCGCACTTTGCGTCTATGGGCGTCCAAATTATTCC
GCTCGACGGCGGCGCGGAGACCGTTTCCCCGAATCATCGGGGCGTGCT
CGCCAACACAAGTTCTGGTTGGCAACTGGGGCTTGCCCCCTGTAGTTC
CTAACGCGAGCGTGCACAAGATTACTGTGAGGCTTGGCGGGGAGTCT
GCAAACCCTTTCCTGTCCTCGCACACGATTCAAGGCAGAAAGGTCTTG
CCGATGACTGTGGCGCTTGGGCTTCTCGCTGAGGCGGCTCGAGGGCTC
TACGTCGGTCACCAAGTAGTCGGGATTGAGGACGCCCAAGTCTTCCAG
GGAGTCGTGTTGGACAAAGGGGCGACGTGTGAGGTCCAGCTTCGCCG
CGAGTCTTCGACTGCAAGCCCAAGCGAGGTTGTGCTGAGTGCTTCGCT
CAATGTATTCGCGGCGGGAAAGGTTGTGCCTGCGTACCGCGCGCATGT
CGTGCTCGGCGCTTCAGGGCCACGCACTGGCGGCGTGCAGCTTGAACT
GAAAGATTTGGGCGTGGACGCCGACCCTGCTTGCTCCGTTGGCAAGGG
TGCGCTGTACGACGGTAGGACGCTGTTCCATGGGCCGGCGTTTCAGTA
CATGGATGAGGTTCTCGGTGCTCGCCTGCAGAGCTTGCCGTGCGGTG
CCGTGTCGTTCCGAGCGCGGCTCAGGACCGCGGCCAATTTGTTTCGCG
CGGAGTGTTGTACGACCCGTTCCTGAACGACACGGTGTTTCAAGCTCT
CCTTGTGGGCCCGTCTGGTCAGGGACAGCGCTTCGCTACCGAGCAA
CGTTGAACGAATCTCGTTCCACGGCCAGCCGCCGAGCGAGGGCGAGG
TGTTTTACACCACGCTCAAGCTGGACAGTGCTGCGAGCGGGCCGCTCG
ACCCGATTGCAAAGGCGCAGTTCTTCCTCCACCGAGCTTGCGGGGCGG
TCTTTGCATCAGGGCGAGCGAGTGTGGTTCTGAACAAGGCTCTTTCGTT
TTGA

SEQ ID NO:9:
CAAGCAATCGGCCATCGAGCTGCGCGTTGGAGCTGCCGATCGAAATC
GAAAGCAAGAGGCCACAAGGCTCAGAAAGAGATGAACCAGGGCGGG
AGAAATGACGAGGGCGTCTCGGTGGCGCGCGCGGACCCATGCCCTGA
CACGCGGATCGCTGTCGTGGGCATGGCGGTCGAGTATGCAGGGTGCC

FIG.4-7

```
GCGGCAAGGAAGCGTTCTGGGACACGCTCATGAACGGCAAAATCAAC
TCTGCCTGTATCTCAGACGATCGCCTCGGGTCAGCACGACGAGAAGA
GCACTATGCGCCCGAGAGGTCAAAGTACGCCGATACGTTCTGCAACG
AGAGGTACGGATGCATCGATCCCAAAGTCGACAACGAGCACGACCTG
CTCCTCGGCCTCGCCGCGGCTGCGCTTCAAGACGCGCAGGACAGGCG
CAGCGACGGCGGCAAGTTCGACCCAGCGCAGCTCAAGCGCTGCGGCA
TTGTCAGCGGCTGCCTGTCCTTCCCGATGGACAACCTGCAAGGCGAGC
TGCTCAACCTTTACCAAGCCCATGCTGAGAGGCGGATTGGCAAGCATT
GCTTCGCGGACCAAACGCCCTGGTCGACGCGAACCAGAGCGCTTCAC
CCGCTGCCCGGGGACCCGAGGACCCACCGCGACCCAGCCTCCTTCGT
CGCCGGACAGCTCGGCCTCGGCCCGCTGCACTACTCGCTCGACGCCGC
CTGCGCCTCGGCCCTTTACGTTCTGCGACTCGCTCAGGACCACCTCCTC
TCGGGCGAGGCTGACTTGATGCTGTGCGGAGCGACGTGCTTCCCAGAG
CCCTTCTTCATCCTGACTGGGTTTAGCACGTTCCACGCGATGCCAGTCG
GTGAGAACGGTGTCTCGATGCCGTTTCATCGGGACACGCAAGGGCTG
ACGCCCGGCGAGGGCGGCTCGGTGATGGTGCTCAAGCGCCTCGCGGA
CGCCGAGCGCGACGGAGACCACATCTACGGGACGCTTCTTGGAGCCA
GCTTGAGCAACGCAGGCTGCGGGCTTCCTCTCAAGCCGCACCAGCCA
AGCGAGGAGGCCTGCTTGAAAGCCACCTACGAGCTCGTCGGCGTGCC
GCCCCGAGACGTCCAGTACGTCGAGTGCCACGCCACCGGCACGCCGC
AGGGCGACACCGTCGAGCTCCAAGCCGTCAAAGCCTGCTTTGAGGGC
GCAAGCCCCGGATCGGGTCCACGAAAGGCAACTTCGGACACACCCT
CGTCGCGGCCGGCTTTGCGGGAATGTGCAAGGTTCTCCTTGCAATGGA
GCGCGGCGTGATCCCCCCGACCCCGGGCGTTGACTCTGGCACCCAGAT
TGATCCCCTCGTCGTCACAGCGGCGCTCCCGTGGCCGGATACGCGCGG
CGGGCCGAAACGCGCAGGACTCTCCGCATTCGGATTCGGGGGCACAA
ACGCGCACGCCGTCTTTGAGGAGCATATTCCCTCGAGAGCTCCGCCCG
CAGTACTCTGCCAGCCTCGCCTCGGCAGCGGACCAAACCGAAAGCTT
GCTATCGTCGGCATGGATGCCACGTTTGGATCCTTGAAGGGTCTCTCC
GCACTAGAAGCTGCGCTTTACGAGGCAAGGCACGCTGCGCGGCCCCT
GCCTGCGAAGCGCTGGCGCTTCTTGGGCGGGGACGAGTCCTTTCTCCA
CGAGATCGGACTCGAGTGCTCTCCGCACGGGTGCTACATTGAGGACGT
GGATGTGGACTTTAAGCGACTCCGCACGCCAATGGTGCCGGAGGACT
TGCTCCGGCCGCAACAGCTCCTGGCCGTGTCGACGATTGACAAGGCC
ATCCTCGACTCGGGCTTGGCCAAGGGCGGCAACGTGGCTGTCCTTGTC
GGCCTCGGGACGGACCTCGAGCTCTACCGCCACCGAGCTCGGGTTGC
GCTTAAGGAGCGTCTTCAAGGACTGGTTCGCTCTGCCGAGGGAGGAG
CCCTGACGTCTCGCCTGATGAACTATATCAATGATAGCGGAACGTCGA
CCTCCTACACGTCGTATATCGGCAACCTCGTCGCCACGCGCGTCTCGT
CCCAGTGGGGCTTCACTGGGCCGTCGTTCACCGTCACGGAAGGGGCC
AACTCGGTCCATCGGTGCGCCCAGCTCGCCAAGTACATGCTCGACCGC
GGCGAGGTCGACGCCGTCGTGGTTGCAGGAGTCGACCTGTGCGGGAG
CGCCGAGGCGTTCTTCGTGAGGTCGCGCCGCATGCAGATCTCGAAAA
GTCAGCGCCCGGCCGCGCCGTTTGACCGCGCCGCAGACGGCTTCTTCG
CGGGGGAAGGGTGCGGCGCCCTCGTCTTCAAACGCCTGACTGACTGT
```

FIG.4-8

```
GTGTCTGGCGAGCGAATCTACGCGTCCCTCGACTCGGTCGTCGTCGCA
ACCACGCCGCGCGCCGCTCTTCGTGCTGCCGCAGGGTCGGCGCGGGTT
GACCCAGCCAGCATCGACATGGTCGAGCTGAGCGCAGATTCCCACCG
GTTTGTGCGGGCGCCAGGCACCGTGGCTCAGCCTCTGACAGCCGAAGT
CGAGGTCGGGGCGGTGCGGGAAGTGATCGGGACCGCGGGGAGGGGC
TCTCGAAGCGTGGCCGTCGGATCGGTCCGCGCCAACGTCGGGGACGC
AGGGTTTGCTTCCGGGGCCGCTGCCCTCGTAAAAACTGCGCTCTGCTT
GCACAACCGCTACTTGGCGGCTACCCCAGGCTGGATGCGCCTGCTGC
CGGCGTGGATTTTGGTGCCGAGCTGTACGTTTGCCGCGAGTCGCGTGC
TTGGGTCAAGAACGCCGGCGTTGCACGGCACGCCGCAATTTCTGGCGT
GGACGAAGGCGGGTCGTGCTATGGGCTGGTTCTTTCGGACGTGCCTGG
GCAGTACGAGACCGGCAACCGCATCTCCTCCAGGCCGAGTCGCCCA
AGCTCTTGCTCCTCGGCTCCAGACCACGCCGCCTTGCTGGACAAGG
TGGCGGCCGAGCTCGCAGCCCTTGAGCAAGCCGACGGCTTGAGCGCC
GCCGCGGCTGCCGTAGACCGCTTACTCGGCGAGTCGCTCGTCGGTTGC
GCGGCTGGCAGCGGCGGGCTGACCCTTTGCTTGGTGGCTTCGCCTGCC
AGCCTCCACAAGGAGCTTGCGCTGGCCCATCGAGGGATCCCGCGCTG
CATCAAAGCACGGCGCGACTGGGCCAGCCCGGCAGGGAGCTACTTCG
CCCCGGAGCCGATCGCAAGCGACCGCGTCGCGTTCATGTACGGGGAA
GGACGAAGCCCGTACTGCGGCGTCGGCCGCGACCTCCACCGGATCTG
GCCCGCGCTGCATGAGCGGGTGAACGCCAAGACTGTCAACCTCTGGG
GTGACGGTGACGCCTGGCTGCTGCCACGTGCAACCTCGGCCGAGGAA
GAGGAGCAACTCTGCCGCAACTTCGACTCGAACCAGGTTGAGATGTTT
CGAACGGGCGTGTACATCTCGATGTGCTTGACCGACCTCGCTCGAAGC
TTGATTGGACTGGGCCCTAAGGCGAGCTTTGGGCTCAGCCTAGGCGAG
GTTTCCATGCTCTTCGCTCTGAGCGAGTCCAACTGTAGACTGTCGGAG
GAAATGACCCGCAGGCTCCGTGCGTCCCGGTGTGGAACTCGGAGCT
CGCCGTCGAGTTCAACGCCCTTCGAAAGTTGTGGGGGGTCGCGCCGGG
GGCACCCGTCGACTCGTTCTGGCAAGGTTATGTCGTGCGCGCAACGCG
GGCTCAGGTGGAGCAAGCCATTGGGGAGGACAATCAGTTTGTGCGTC
TCCTGATCGTGAACGACTCGCAATCAGTCCTGATCGCCGGCAAGCCGG
CGGCGTGCGAAGCCGTAATTGCTCGCATCGGGTCTATTCTTCCCCCGCT
GCAAGTGTCGCAAGGCATGGTGGGGCACTGTGCCGAGGTCTTGCCGT
ACACGAGCGAGATCGGGCGCATCCACAACATGCTTCGCTTCCCATCGC
AGGACGAAACGGGCGGTTGCAAAATGTACTCTAGCGTCTCAAACTCG
CGCATCGGGCCAGTCGAGGAGAGCCAGATGGGCCCAGGCACTGAGCT
CGTTTTCTCGCCGTCAATGGAAGACTTTGTCGCCCAGCTGTACTCGCGA
GTTGCAGACTTTCCGGCGATCACCGAGGCGGTTTACCAGCAGGGTCAT
GACGTGTTTGTCGAAGTGGGGCCGGACCATTCACGGTCGGCTGCTGTC
CGCTCCACGCTTGGACCCACTCGGCGACACATCGCTGTGGCGATGGAC
CGCAAGGGTGAGTCAGCTTGGTCGCAGCTTCTGAAAATGCTGGCTACG
CTTGCGTCGCACCGCGTGCCGGGCCTGGACCTTTCATCCATGTACCAC
CCCGCAGTGGTGGAGCGTTGCAGGCTGGCGCTGGCAGCACAACGATC
GGGCCAGCCAGAGCAGCGGAACAAGTTTTTGCGCACGATAGAGGTGA
ATGGGTTCTACGACCCGGCCGACGCGACCATCCCTGAGGCCGTCGCA
```

FIG.4-9

ACAATTCTGCCGGCAACTGCTGCGATTTCGCCTCCAAAGCTTGGCGCT
CCGCACGACTCGCAACCCGAGGCGGAGGCTCGCCCCGTGGGCGAGGC
CTCTGTGCCAAGGCGGGCCACGAGCTCGAGCAAATTGGCCAGGACGC
TTGCCATCGATGCTTGCGACTCCGACGTGCGCGCCGCCTTGCTGGACC
TGGACGCGCCAATCGCGGTCGGCGGCTCCTCGCGCGCCCAAGTCCCG
CCGTGCCCAGTGAGCGCGCTCGGAAGCGCCGCCTTTCGAGCGGCACA
CGGCGTCGATTATGCGCTCTACATGGGCGCAATGGCCAAAGGCGTCG
CGTCAGCGGAGATGGTCATCGCTGCTGGCAAGGCCCGCATGCTCGCGT
CATTTGGCGCGGGGGGGCTTCCCCTGGGCGAGGTCGAAGAGGCGTTG
GACAAGATCCAGGCCGCTCTGCCCGAGGGGCCGTTCGCCGTCAACCT
CATTCACTCGCCGTTCGATCCAAACCITGAGGAGGGCAACGTCGAGCT
GTTCCTGAGGCGCGGTATCCGGCTGGTCGAGGCCTCTGCGTTCATGTC
GGTCACGCCGTCGTTGGTGCGCTACCGAGTCGCCGGACTCGAGCGAG
GCCCTGGCGGGACCGCCCGAGTGCTGAACCGCGTGATTGGCAAGGTG
AGCCGTGCGGAGCTCGCAGAAATGTITATGCGGCCGCCTCCCGCCGCG
ATCGTCTCCAAGCTCCTCGCCCAGGGCCTGGTCACTGAGGAGCAGGC
GTCACTTGCAGAGATCGTCCCACTGGTTGACGACGTTGCAATCGAAGC
CGACTCGGGCGGTCACACAGACAACCGCCCGATCCACGTCGTTTTGCC
CGTCGTCCTCGCGCTGCGAGACCGCGTCATGCGTGAGTGCAAGTATCC
AGCCGCCAATCGCGTCCGCGTGGGCGCCGGAGGCGGGATCGGCTGCC
CTGCCGCGGCGCGAGCTGCGTTCGACATGGGCGCAGCATTCGTTCTCA
CGGGCTCGATCAACCAGCTCACGCGCCAGGCTGGGACGAGCGACAGC
GTGCGTGCTGCCCTTGCACGCGCGACCTACTCGGACGTGACAATGGCC
CCGGCGGCCGATATGTITGACCAGGGCGTCAAGCTGCAGGTCTTGAAG
CGCGGCACGATGTTCCCGGCGCGCGCAAACAAGCTGTACGAGTTGTTC
ACCACTTACCAGTCGCTGGACGCGATCCCTCGGGCTGAGCTGGCTCGC
CTGGAAAAGCGAGTTTTCCGCATGTCCATCGACGAGGT1TGGAACGA
AACCAAGCAGTTCTACGAGACCCGGCTCAACAACCCCGCCAAGGTTG
CCCGGGCGGAGCGCGACCCCAAGCTCAAGATGTCGCTCTGCTTTCGGT
GGTACTTGTCGAAAAGCTCCAAGTGGGCATCGACCTGGACAAGTTGGG
CGCGAGCTGGACTACCAGGTCTGGTGCGGCCCCACGATTGGCGCTTTC
AACGAGTTCGTGAAGGGGTCCAGCCTCGACGCGGAGGCTTGCGGGGG
GCGGTTTCCTTGCGTTGTGCGCGTTAACCAGGAGATATTATGTGGCGCT
GCTTACGAGCAGCGACTGGCGCGTTTCATGCTGCTCGCTGGCCGGGAA
AGCGCGGACGCGTTGGCGTACACGGTTGCGGAAGCCAGATAG

SEQ ID NO:10:
RKCIRPSLGHHWAIIGVLGRALRIVRPIRYEATNLRRLPRSGWLVALGLFCD
LSSCAGKLDLQTRDTAKDPCCKRKWSASRAPPRPRAEADKASNEMETKD
DRVAIVGMSAILPCGESVRESWEAIREGLDCLQDLPADRVDITAYYDPNKT
TKDKIYCKRGGFIPEYDFDAREFGLNMFQMEDSDANQTVTLLKVKEALED
AGVEPFTKKKKNIGCVLGIGGGQKASHEFYSRLNYVVVEKVLRKMNLPDE
VVEAAVEKYKANFPEWRLDSFPGFLGNVTAGRCSNVFMEGMNCVVDA
ACASSLIAIKVAIDELLHGDCDTMIAGATCTDNSIGMYMAFSKTPVFSTDQ
SVKAYDAKTKGMLIGEGSAMVVLKRYADAVRDGDEIHAVIRACASSSDGK

FIG.4-10

AAGIYAPTVSGQEEALRRAYARAGVDPSTVLVEGHGTGTPVGDRIELTAL
RNVFDAANKGRKETVAVGSIKSQIGHLKAVAGFAGLVKVVMALKHKTLP
QTINVHDPPALHDGSPIQDSSLYINTMNRPWFTAPGVPRRAGISSFGFGGA
NYHAVLEEAEPEHAKPYRMNQVPQPVLLHASSASALASICDAQADALQA
AVSPEASKHADYRAIVAFHEAFKLRAGVPAGHARIGFVSGSAAATLAVLR
AASAKLKQSSATLEWTLLREGVTYRSAAMHTPGSVAALFAGQGAQYTHM
FADVAMNWPPFRSAVQEMDAAQVTAAAPKRLSEVLYPRKPYAAEPEQD
NKAISMTINSQPALMACAAGAFEVFRQAGLAPDHVAGHSLGEFGALLAA
GCASREELFRLVCSRAKAMQDVKPSEGVMAAVIGRGADKLTLQGDGAW
LANCNSPSQVVISGDKTAVERESSRLAGLGFRIIPLACEGAFHSPHMTAAQ
ATFQAALDSLKISTPTNGARLYNNVSGKTCRSLGELRDCLGKHMTSPVLFQ
AQVENMYAAGARIFVEFGPKQVLSKLVGEILADKSDFVTVAVNSSSSKDSD
VQLREAAAKLAVLGVPLANFDPWELCDARRLRECPRSKTTLRLSAATYVS
NKTLAAREKVMEDNCDFSSLFASGPASQEMEREIANLRAELEAAQRQLDT
AKTQLARKQVQDPTADRQRDMIAKHRSTLAAMVKEFEALASGSPCAVPF
APVVDTAVEDVPFADKVSTPPPQVTSAPIAELARAEAVVMEVLAAKTGYE
VDMIEADMLLDAELGIDSVKRIEILAAVQAQLGVEAKDVDALSRTRTVGE
VVDAMKAEIGGQATSAPSPMAQPQASAPSPSPTASVLPKPVALPASVDPA
KLARAEAVVMEVLAAKTGYEVDMIEADMLLDAELGIDSVKRIEILAAVQA
QLGVEAKDVDALSRTRTVGEVVDAMKAEIGGQATSAPASVAQPQASAPS
PSATTASVLPKPVAAPTSADPAKLARAEAVVMEVLAAKTGYEVDMIEAD
MLLDAELGIDSVKRIEILAAVQAQLGVEAKDVDALSRTRTVGEVVEAMKA
EIGGQATSAPASVAQPQISVSPTPLAASPSADPAKLARAEAVVMEVLAAKT
GYEVDMIEADMLLDAELGIDSVKRIEILAAVQAQLGVEAKDVDALSRTRT
VGEVVDAMKAEIGGQATSAPASVAQPQASAPSPSATASVLPKPVAAPTSA
DPAKLARAEAVVMEVLAAKTGYEVDMIEADMLLDAELGIDSVKRIEILAA
VQAQLGVEAKDVDALSRTRTVGEVVEAMKAEIGGQATSAPASMAQPSQIS
VSPTPLAASPSADPAKLARAEAVVMEVLAAKTGYEVDMIEADMLLDAEL
GIDSVKRIEILAAVQAQLGVEAKDVDALSRTRTVGEVVDAMKAEIGGQAT
SAPASVAQPQASAPSPSATASAPVTPLAAPASVDPAKLARAEAVVMEVLA
AKTGYEVDMIEADMLLDAELGIDSVKRIEILAAVQAQLGVEAKDVDALSR
TRTVGEVVDAMKAEIGGQATSAPASVAQPQASAPSPSATASVLPKPVASP
ASVDPAKLARAEAVVMEVLAAKTGYEVDMIDADMLLDAELGIDSVKRIEI
LAAVQAQLGVEAKDVDALSRTRTVGEVVEAMKAEIGAAGPNDAQAASG
HLFGTGCEDLSLCSASVVELARCSELALERPMDRPILIVSDGSALPAALASRL
GSCAVILTTAGETDQSVRSTKHVDMEGWGEADLVRALEAVESRFGVPGGV
VVLERASETARDQLGFALLLAKHSSKALNQQIPGGRACFVGVSRIDGKLGL
SGACAKGKGWAEAAEIAQQGAVAGLCKTLDLEWPHVFARSIDIELGANE
ETAAQAIFEELSCPDLTVREAGYTKDGKRWTTEARPVGLGKPKQALRSSDV
FLVSGGARGITPVCVRELAKSISGGTFVLLGRSPLADDPAWACGVEEANIG
TAAMAHLKAEFAAGRGPKPTPKAHKALVGSVLGAREVLGSLESIRAQGA
RAEYVSCDVSCAERVKAVVDDLERRVGAVTGVVHASGVLRDKSVERLELA
DFEVVYGTKVDGLLNLLQAVDRPKLRHLVLFSSLAGFHGNTGQAVYAMA
NEALNKMAFHLETAMPGLSVKTIGFGPWDGGMVNDALKAHFASMGVQI
IPLDGGAETVSRIIGACSPTQVLVGNWGLPPVVPNASVHKITVRLGGESAN

FIG.4-11

PFLSSHTIQGRKVLPMTVALGLLAEAARGLYVGHQVVGIEDAQVFQGVVL
DKGATCEVQLRRESSTASPSEVVLSASLNVFAAGKVVPAYRAHVVLGASG
PRTGGVQLELKDLGVDADPACSVGKGALYDGRTLFHGPAFQYMDEVLRC
SPAELAVRCRVVPSAAQDRGQFVSRGVLYDPFLNDTVFQALLVWARLVRD
SASLPSNVERISFHGQPPSEGEVFYTTLKLDSAASGPLDPIAKAQFFLHRAC
GAVFASGRASVVLNKALSF

SEQ ID NO:11:
QAIGHRAARWSCRSKSKARGHKAQKEMNQGGRNDEGVSVARADPCPDT
RIAVVGMAVEYAGCRGKEAFWDTLMNGKINSACISDDRLGSARREEHYA
PERSKYADTFCNERYGCIDPKVDNEHDLLLGLAAAALQDAQDRRSDGGK
FDPAQLKRCGIVSGCLSFPMDNLQGELLNLYQAHAERRIGKHCFADQTPW
STRTRALHPLPGDPRTHRDPASFVAGQLGLGPLHYSLDAACASALYVLRL
AQDHLLSGEADLMLCGATCFPEPFFILTGFSTFHAMPVGENGVSMPFHRD
TQGLTPGEGGSVMVLKRLADAERDGDHIYGTLLGASLSNAGCGLPLKHQ
PSEEACLKATYELVGVPPRDVQYVECHATGTPQGDTVELQAVKACFEGAS
PRIGSTKGNFGHTLVAAGFAGMCKVLLAMERGVIPPTPGVDSGTQIDPLV
VTAALPWPDTRGGPKRAGLSAFGF GGTNAHAVFEEHIPSRAPPAVLCQPR
LGSGPNRKLAIVGMDATFGSLKGLSALEAALYEARHAARPLPAKRWRFLG
GDESFLHEIGLECSPHGCYIEDVDVDFKRLRTPMVPEDLLRPQQLLAVSTID
KAILDSGLAKGGNVAVLVGLGTDLELYRHRARVALKERLQGLVRSAEGG
ALTSRLMNYINDSGTSTSYTSYIGNLVATRVSSQWGFTGPSFTVTEGANSVH
RCAQLAKYMLDRGEVDAVVVAGVDLCGSAEAFFVRSRRMQISKSQRPAA
PFDRAADGFFAGEGCGALVFKRLTDCVSGERIYASLDSVVVATTPRAALRA
AAGSARVDPASIDMVELSADSHRFVRAPGTVAQPLTAEVEVGAVREVIGT
AGRGSRSVAVGSVRANVGDAGFASGAAALVKTALCLHNRYLAATPGWD
APAAGVDFGAELYVCRESRAWVKNAGVARHAAISGVDEGGSCYGLVLSD
VPGQYETGNRISLQAESPKLLLLSAPDHAALLDKVAAELAALEQADGLSA
AAAAVDRLLGESLVGCAAGSGGLTLCLVASPASLHKELALAHRGIPRCIK
ARRDWASPAGSYFAPEPIASDRVAFMYGEGRSPYCGVGRDLHRIWPALHE
RVNAKTVNLWGDGDAWLLPRATSAEEEQLCRNFDSNQVEMFRTGVYIS
MCLTDLARSLIGLGPKASFGLSLGEVSMLFALSESNCRLSEEMTRRLRASPV
WNSELAVEFNALRKLWGVAPGAPVDSFWQGYVVRATRAQVEQAIGEDN
QFVRLLIVNDSQSVLIAGKPAACEAVIARIGSILPPLQVSQGMVGHCAEVLP
YTSEIGRIHNMLRFPSQDETGGCKMYSSVSNSRIGPVEESQMGPGTELVFSPS
MEDFVAQLYSRVADFPAITEAVYQQGHDVFVEVGPDHSRSAAVRSTLGPT
RRHIAVAMDRKGESAWSQLLKMLATLASHRVPGLDLSSMYHPAVVERCR
LALAAQRSGQPEQRNKFLRTIEVNGFYDPADATIPEAVATILPATAAISPPK
LGAPHDSQPEAEARPVGEASVPRRATSSSKLARTLAIDACDSDVRAALLDL
DAPIAVGGSSRAQVPPCPVSALGSAAFRAAHGVDYALYMGAMAKGVASA
EMVIAAGKARMLASFGAGGLPLGEVEEALDKIQAALPEGPFAVNLIHSPFD
PNLEEGNVELFLRRGIRLVEASAFMSVTPSLVRYRVAGLERGPGGTARVLN
RVIGKVSRAELAEMFMRPPPAAIVSKLLAQGLVTEEQASLAEIVPLVDDVAI
EADSGGHTDNRPIHVVLPVVLALRDRVMRECKYPAANRVRVGAGGGIGC
PAAARAAFDMGAAFVLTGSINQLTRQAGTSDSVRAALARATYSDVTMAP

FIG.4-12

AADMFDQGVKLQVLKRGTMFPARANKLYELFTTYQSLDAIPRAELARLEK
RVFRMSIDEVWNETKQFYETRLNNPAKVARAERDPKLKMSLCFRWYLSKS
SKWASTGQVGRELDYQVWCGPTIGAFNEFVKGSSLDAEACGGRFPCVVRV
NQEILCGAAYEQRLARFMLLAGRESADALAYTVAERAR

SEQ ID NO:12:
ATGGAGACAAAGGACGATCGCGTTGCGATCGTGGGCATGTCGGCCAT
ACTGCCTTGCGGTGAGTCAGTGCGCGAGTCGTGGGAGGCGATTCGCG
AGGGGCTCGATTGCCTGCAGGACCTGCCTGCGGACCGAGTCGATATC
ACGGCGTACTACGACCCGAACAAGACAACCAAGGACAAGATCTACT
GCAAGCGCGGCGGCTTCATTCCCGAGTATGACTTTGACGCGCGCAGT
TCGGCCTCAACATGTTCCAGATGGAGGACTCGGACGCCAACCAAACC
GTGACTTTGCTCAAGGTCAAGGAGGCTCTCGAGGACGCCGGGGTGGA
GCCCTTCACAAAGAAGAAGAACATTGGCTGCGTGCTCGGCATCG
GCGGCGGGCAGAAGGCGAGCCACGAGTTTTACTCCCGACTCAACTAT
GTGGTCGTGGAGAAGGTGCTTCGCAAGATGAACCTCCCCGACGAGGT
TGTCGAGGCCGCCGTCGAAAAGTACAAGGCCAACTTTCCTGAATGGC
GCCTCGACTCGTTCCCTGGGTTTCTTGGCAACGTGACCGCCGGGCGGT
GCAGCAACGTCTTCAACATGGAAGGCATGAACTGCGTCGTGGACGCT
GCGTGCGCCAGCTCGCTCATCGCGATCAAGGTTGCCATTGATGAGCTC
CTCCACGGGGACTGCGACACCATGATTGCCGGTGCGACCTGCACCGA
CAACTCGATCGGGATGTACATGGCCTTTTCCAAAACCCCAGTTTTCTCC
ACCGACCAGAGCGTCAAGGCGTACGACGCCAAGACGAAAGGCATGC
TCATCGGCGAAGGCTCGGCCATGGTCGTGCTCAAGCGGTACGCGGAC
GCCGTTCGGGATGGTGATGAGATCCATGCCGTCATCAGGGCATGCGCC
TCGTCCAGCGACGGCAAGGCTGCTGGCATTTACGCACCGACGGTGTCG
GGTCAAGAAGAGGCACTGCGGCGCGCGTACGCCCGAGCTGGCGTGGA
CCCCTCCACCGTCACGCTGGTGGAGGGCCACGGCACTGGCACACCCG
TCGGGGACCGGATTGAGCTGACCGCCTTGCGCAACGTCTTTGACGCAG
CCAACAAAGGCCGCAAGGAAACAGTCGCGGTGGGAAGCATCAAGTC
GCAGATCGGTCACCTGAAGGCCGTGGCCGGCTTTGCCGGTCTCGTCAA
GGTTGTCATGGCCCTCAAGCACAAGACGCTGCCGCAGACCATCAACG
TTCACGACCCGCCCGCACTGCACGACGGCTCGCCCATCCAGGATTCGA
GTCTTTACATCAACACGATGAACCGGCCCTGGTTTACGGCACCTGGCG
TCCCCCGCCGTGCAGGCATCTCTAGCTTTGGGTTTGGCGGCGCCAACT
ACCACGCTGTTCTCGAAGAGGCCGAGCCTGAGCACGCGAAGCCGTAT
CGCATGAACCAAGTTCCACAACCGGTGCTCTTGCACGCAAGCTCCGCG
TCAGCTCTT

SEQ ID NO:13:
METKDDRVAIVGMSAILPCGESVRESWEAIREGLDCLQDLPADRVDITAYY
DPNRGGFIPEYDFDAREFGLNMFQMEDSDANQTVTLLKVKEALEDAGVEP
FTK
KKKNIGCVLGIGGGQKASHEFYSRLNYVVVEKVLRKMNLPDEVVEAAVEK
YKANFPEWRLDSFPGFLGNV TAGRCSNVFN

FIG.4-13

MEGMNCVVDAACASSLIAIK
VAIDELLHGDCDTMIAGATCTDNSIGMYMAFSKTPVFSTDQSVKAYDAKT
KGMLIGEGSAMVVLKRYADAVRDGDEIHAVIRACASSSDGKAAGIYAPTV
SGQEEALRRAYARAGVDPSTVTLVEGHGTGTPVGDRIELTALRNVFDAAN
KGRKETVAVG SIKSQIGHLK
AVAGFAGLVKVVMALKHKTLPQTINVHDPP
ALHDGSPIQDSSLYINTMNRPWFTAPGVPRRAGISSFGFGGANYHAVLEE
AEPEHAKPYRMNQVPQPVLLHASSASAL

SEQ ID NO:14:
CAGTCGAGTGCGACGCTCGAATGGACCCTGCTCCGCGAGGGCGTCAC
GTACCGCTCCGCCGCGATGCACACTCCTGGCAGTGTCGCTGCTCTGTTT
GCCGGGCAAGGCGCGCAGTACACGCACATGTTCGCTGACGTTGCCAT
GAACTGGCCACCGTTTCGAAGCGCCGTGCAAGAGATGGATGCCGCTC
AAGTCACGGCGGCAGCGCCGAAGCGCCTCAGCGAGGTCCTGTATCCG
CGCAAGCCGTACGCTGCAGAGCCCGAGCAAGACAACAAGGCCATCTC
GATGACGATTAACTCGCAACCGGCCCTCATGGCCTGCGCTGCTGGGGC
GTTTGAGGTGTTTCGTCAAGCTGGTCTTGCGCCCGACCACGTCGCGGG
TCATTCTCTCGGCGAGTTTGGTGCTTTGCTCGCCGCTGGATGCGCAAGC
CGTGAGGAGCTCTTCCGTCTGGTCTGCAGCAGAGCGAAGGCAATGCA
AGACGTTCCCAAGCCAAGCGAGGGCGTCATGGCAGCTGTCATCGGCC
GTGGTGCTGACAAGCTCACGCTGCAAGGCGATGGTGCGTGGCTTGCCA
ACTGCAACTCGCCAAGCCAAGTGGTCATTTCCGGCGACAAGACTGCT
GTCGAGCGTGAATCCAGCCGGTTGGCAGGCCTTGGCTTCAGGATCATT
CCGCTTGCATGCGAAGGCGCCTTCCATTCACCGCACATGACGGCGGCC
CAGGCCACGTTTCAGGCTGCACTGGACAGCCTCAAGATCTCCACCCCG
ACGAACGGGGCGCGCCTGTACAACAACGTTTCCGGAAAGACCTGCCG
ATCCCTGGGTGAACTCCGCGACTGCCTGGGCAAGCACATGACAAGTC
CTGTGCTCTTCCAGGCACAGGTAGAGAACATGTACGCTGCCGGGGCG
CGCATTTTCGTGGAGTTTGGCCCGAAGCAAGTCCTCTCCAAGCTCGTA
GGCGAGATTCTCGCCGACAAGTCAGACTTTGTGACAGTCGCGGTCAAC
TCGTCATCGTCCAAGGACAGCGACGTGCAACTTCGTGAAGCTGCTGCG
AAGCTCGCGGTCCTTGGCGTCCCGTTGGCGAACTTTGACCCTTGGGAG
CTCTGCGACGCGCGGCGTCTTCGCGAATGCCCGCGATCCAAGACGAC
GTTGCGCTTGTCTGCAGCGACCTACGTGTCGAACAAGACCCTTGCTGC
TAGGGAGAAGGTCATGGAGGACAACTGCGACTTTTCTTCGCTCTTTGC
CTCCGGTCCAGCAAGCCAAGAGATGGAGCGAGAAATAGCCAACCTTC
GCGCTGAGCTGGAGGCGGCCCAACGCCAGCTTGACACGGCCAAA

SEQ ID NO:15:
QSSATLEWTLLREGVTYRSAAMHTPGSVAALFAGQGAQYTHMFADVAM
NWPPFRSAVQEMDAAQVTAAAPKRLSEVLYPRKPYAAEPEQDNKAISMTI
NSQPALMACAAGAFEVFRQAGLAPDHVAGHSLGEFGALLAAGCASREEL
FRLVCSRAKAMQDVPKPSEGVMAAVIGRGADKLTLQGDGAWLANCNSP
SQVVISGDKTAVERESSRLAGLGFRIIPLACEGAFHSPHMTAAQATFQAAL

FIG.4-14

DSLKISTPTNGARLYNNVSGKTCRSLGELRDCLGKHMTSPVLFQAQVENM
YAAGARIFVEFGPKQVLSKLVGEILADKSDFVTVAVNSSSSKDSDVQLREA
AAKLAVLGVPLANFDPWELCDARRLRECPRSKTTLRLSAATYVSNKTLAA
REKVMEDNCDFSSLFASGPASQEMEREIANLRAELEAAQRQLDTAK

SEQ ID NO:16:
CAAGTCACTTCCGCTCCCATCGCCGAGCTCGCGCGCGCCGAGGCCGTC
GTCATGGAGGTTCTCGCTGCCAAGACTGGCTACGAGGTCGACATGATC
GAGGCCGACATGCTGCTCGACGCCGAGCTCGGCATCGACTCGGTCAA
GCGCATTGAGATCCTGGCAGCTGTCCAGGCCCAGCTCGGGGTCGAGG
CCAAGGACGTCGACGCGCTCAGCCGCACACGAACAGTTGGCGAGGTC
GTTGACGCCATGAAGGCTGAGATCGGCGGG

SEQ ID NO:17:
QVTSAPIAELARAEAVVMEVLAAKTGYEVDMIEADMLLDAELGIDSVKRIE
ILAAVQAQLGVEAKDVDALSRTRTVGEVVDAMKAEIGG

SEQ ID NO:18:
CATCTCTTTGGCACGGGATGTGAAGACCTGAGCCTTTGCTCTGCTTCTG
TGGTTGAGATTGCTCGTTGCAGCGAACTAGCTCTGGAGCGCCCGATGG
ATCGGCCCATTCTTATTGTAAGCGATGGATCAGCATTGCCGGCGGCTC
TGGCTAGTCGACTGGGGTCGTGTGCAGTAATCCTCACGACCGCAGGCG
AGACCGACCAATCTGTGCGCTCGACGAAGCACGTTGACATGGAAGGG
TGGGGCGAGGCAGATCTCGTGCGCGCTCTTGAAGCAGTAGAGTCTCG
ATTCGGCGTCCCAGGCGGCGTCGTGGTGCTTGAGCGCGCCTCAGAAAC
AGCTAGGGACCAGCTTGGCTTTGCCCTGCTGCTTGCCAAGCATTCGAG
CAAAGCGCTCAACCAGCAGATCCCAGGCGGGCGCGCCTGCTTCGTGG
GCGTCTCGCGAATCGACGGAAAGCTCGGACTTAGCGGAGCTTGCGCG
AAAGGAAAGGGCTGGGCTGAGGCCGCAGAGATTGCTCAGCAAGGAG
CCGTCGCGGGCTTGTGCAAGACCTTGGACCTAGAGTGGCCGCACGTCT
TCGCTCGCAGCATCGACATCGAGCTTGGCGCGAACGAAGAAACAGCT
GCGCAAGCAATCTTTGAGGAGCTCTCTTGCCCGGACCTAACGGTGCGC
GAAGCAGGATACACCAAAGACGGCAAGCGGTGGACGACTGAGGCGC
GACCGGTTGGGCTTGGCAAGCCCAAGCAGGCACTACGTTCTTCGGAC
GTCTTCTTGGTTTCTGGTGGGGCGCGGGGAATTACACCTGTTTGCGTTC
GCGAGTTGGCCAAATCGATCAGTGGTGGCACTTTTGTCCTCCTCGGGC
GGTCCCCTCTCGCTGATGATCCGGCGTGGGCTTGCGGCGTCGAGGAAG
CAAACATTGGACAGCCGCTATGGCGCACCTCAAGGCCGAGTTCGCA
GCCGGGCGCGGCCCGAAGCCGACGCCAAAGGCCCACAAAGCACTCG
TTGGGAGCGTCCTGGGGGCGCGCGAAGTCCTTGGTTCGCTAGAGAGTA
TTCGCGCCCAGGGTGCGCGCGCCGAGTACGTTTCCTGCGACGTTTCGT
GTGCGGAGCGCGTCAAGGCCGTCGTCGACGATCTCGAGCGACGGGTC
GGGGCTGTAACTGGGGTTGTGCACGCCTCTGGTGTTCTCCGAGACAAG
TCCGTTGAGCGCTTGGAGCTCGCCGACTTCGAGGTCGTGTACGGCACC
AAGGTGGACGGCCTGCTCAACCTGCTGCAGGCCGTGGACCGCCCAA

FIG.4-15

ACTCCGGCACTTGGTCCTCTTCAGCTCCCTGGCCGGTTTCCACGGCAAC
ACTGGGCAGGCCGTGTACGCTATGGCGAATGAGGCGCTGAACAAGAT
GGCCTTCCATTTGGAAACTGCGATGCCTGGCCTCTCGGTCAAGACGAT
CGGGTTTGGACCTTGGGACGGCGGCATGGTCAACGATGCGCTGAAAG
CGCACTTTGCGTCTATGGCGTCCAAATTATTCCGCTCGACGGCGGCG
CGGAGACCGTTTCCCGAATCATCGGGGCGTGCTCGCCAACACAAGTTC
TGGTTGGCAACTGGGGCTTGCCCCCTGTAGTTCCTAACGCGAGCGTGC
ACAAGATTACTGTGAGGCTTGGCGGGGAGTCTGCAAACCCTTTCCTGT
CCTCGCACACGATTCAAGGCAGAAAGGTCTTGCCGATGACTGTGGCG
CTTGGGCTTCTCGCTGAGGCGGCTCGAGGGCTCTACGTCGGTCACCAA
GTAGTCGGGATTGAGGACGCCCAAGTCTTCCAGGGAGTCGTGTTGGAC
AAAGGGGCGACGTGTGAGGTCCAGCCGCCGCGAGTCTTCGACTGC
AAGCCCAAGCGAGGTTGTGCTGAGTGCTTCGCTCAATGTATTCGCGGC
GGGAAAGGTTGTGCCTGCGTACCGCGCGCATGTCGTGCTCGGCGCTTC
AGGGCCACGCACTGGCGGCGTGCAGCTTGAACTGAAAGATTTGGGCG
TGGACGCCGACCCTGCTTGCTCCGTTGGCAAGGGTGCGCTGTACGACG
GTAGGACGCTGTTCCATGGGCCGGCGTTTCAGTACATGGATGAGGTTC
TTCGGTGCTCGCCTGCAGAGCTTGCCGTGCGGTGCCGTGTCGTTCCGA
GCGCGGCTCAGGACCGCGGCCAATTTGTTTCGCGCGGAGTGTTGTACG
ACCCGTTCCTGAACGACACGGTGTTTCAAGCTCTCCTTGTTTGGGCCCG
TCTGGTCAGGGACAGCGCTTCGCTACCGAGCAACGTTGAACGAATCTC
GTTCCACGGCCAGCCGCCGAGCGAGGGCGAGGTGTTTTACACCACGC
TCAAGCTGGACAGTGCTGCGAGCGGGCCGCTCGACCCGATTGCAAAG
GCGCAGTTCTTCCTCCACCGAGCTTGCGGGGCGGTCTTTGCATCAGGG
CGAGCGAGTGTGGTTCTGAACAAGGCTCTTTCGTTT

SEQ ID NO:19:
ASGHLFGTGCEDLSLCSASVVEIARCSELALERPMDRPILIVSDGSALPAAL
ASRLGSCAVILTTAGETDQSVRSTKHVDMEGWGEADLVRALEAVESRFGV
PGGVVVLERASETARDQLGFALLLAKHSSKALNQQIPGGRACFVGVSRIDG
KLGLSGACAKGKGWAEAAEIAQQGAVAGLCKTLDLEWPHVFARSIDIEL
GANEETAA
QAIFEELSCPDLTVREAGYTKDGKRWTTEARPVGLGKPKQALRSSDVFLV
SGGARGITPVCVRELAKSISGGTFVLLGRSPLADDPAWACGVEEANIGTA
AMAHLKAEFAAGRGPKPTKAHKALVGSVLGAREVLGSLESIRAQGARA
E
YVSCDVSCAERVKAVVDDLERRVGAVTGVVHASGVLRDKSVERLELADFE
VVYGTKVDGLLNLLQAVDRPKLRHLVLFSSLAGFHGNTGQAVYAMANE
AL
NKMAFHLETAMPGLSVKTIGFGPWDGGMVNDALKAHFASMGVQIIPLDG
G
AETVSRTIGACSPTQVLVGNWGLPPVVPNASVHKITVRLGGESANPFLSS
HTIQGRKVLPMTVALGLLAEAARGLYVGHQVVGIEDAQVFQGVVLDKGA
T
CEVQLRRESSTASPSEVVLSASLNVFAAGKVVPAYRAHVVLGASGPRTGG

FIG.4-16

VQLELKDLGVDADPACSVGKGALYDGRTLFHGPAFQYMDEVLRCSPAEL
A
VRCRVVPSAAQDRGQFVSRGVLYDPFLNDTVFQALLVWARLVRDSASLPS
NVERISFHGQPPSEGEVFYTTLKLDSAASCPLDPIAKAQFFLHRACGAVF
ASGRASVVLNKALSF

SEQ ID NO:20:
ATGAACCAGGGCGGGAGAAATGACGAGGGCGTCTCGGTGGCGCGCG
GACCCATGCCCTGACACGCGGATCGCTGTCGTGGGCATCGCGGTCGAGTA
TGCAGGGTGCCGCGGCAAGGAAGCGTTCTGGGACACGCTCATGAACGGC
AAAATCAACTCTGCCTGTATCTCAGACGATCGCCTCGGGTCAGCACGACG
AGAAGAGCACTATGCGCCCGAGAGGTCAAAGTACGCCGATACGTTCTGC
AACGAGAGGTACGGATGCATCGATCCCAAAGTCGACAACGAGCACGAC
CTGCTCCTCGGCCTCGCCGCGGCTGCGCTTCAAGACGCGCAGGACAGGCG
CAGCGACGGCGGCAAGTTCGACCCAGCGCAGCTCAAGCGCTGCGGCATT
GTCAGCGGCTGCCTGTCCTTCCCGATGGACAACCTGCAAGGCGAGCTGCT
CAACCTTTACCAAGCCCATGCTGAGAGGCGGATTGGCAAGCATTGCTTCG
CGGACCAAACGCCCTGGTCGACGCGAACCAGAGCGCTTCACCCGCTGCC
CGGGGACCCGAGGACCCACCGCGACCCAGCCTCCTTCGTCGCCGGACAG
CTCGGCCTCGGCCCGCTGCACTACTCGCTCGACGCCGCCTGCGCCTCGGC
CCTTTACGTTCTGCGACTCGCTCAGGACCACCTCCTCGGGCGAGGCTG
ACTTGATGCTGTGCGGAGCGACGTGCTTCCCAGAGCCCTTCTTCATCCTGA
CTGGGTTTAGCACGTTCCACGCGATGCCAGTCGGTGAGAACGGTGTCTCG
ATGCCGTTTCATCGGGACACGCAAGGGCTGACGCCCGGCGAGGGCGGCT
CGGTGATGGTGCTCAAGCGCCTCGCGGACGCCGAGCGCGACGGAGACCA
CATCTACGGGACGCTTCTTGGAGCCAGCTTGAGCAACGCAGGCTGCGGG
CTTCCTCTCAAGCCGCACCAGCCAAGCGAGGAGGCCTGCTTGAAAGCCA
CCTACGAGCTCGTCGGCGTGCCGCCCCGAGACGTCCAGTACGTCGAGTGC
CACGCCACCGGCACGCCGCAGGGCGACACCGTCGAGCTCCAAGCCGTCA
AGCCTGCTTTGAGGGCGCAAGCCCCCGGATCGGGTCCACGAAAGGCAA
CTTCGGACACACCCTCGTCGCGGCCGGCTTTGCGGGAATGTGCAAGGTTC
TCCTTGCAATGGAGCGCGGCGTGATCCCCCCGACCCCGGGCGTTGACTCT
GGCACCCAGATTGATCCCCTCGTCGTCACAGCGGCGCTCCCGTGGCCGGA
TACGCGCGGCGGGCCGAAACGCGCAGGACTCTCCGCATTCGGATTCGGG
GGCACAAACGCGCACGCCGTCTTTGAGGAGCATATTCCCTCGAGAGCT

SEQ ID NO:21:
MNQGGRNDEGVSVARADPCPDTRIAVVGMAVEYAGCRGKEAFWDTLMNG
KINSACISDDRLGSARREEHYAPERSKYADTFCNERYGCIDPKVDNEHDLLLG
LAAAALQDAQDRRSDGGKFDPAQLKRCGIVSGCLSFPMDNLQGELLNLYQA
HAERRIGKHCFADQTPWSTRTRALHPLPGDPRTHRDPASFVAGQLGLGPLHY
SLDAACASALYVLRLAQDHLLSGEADLMLCGATCFPEPFFILTGFSTFHAMPV
GENGVSMPFHRDTQGLTPGEGGSVMVLKRLADAERDGDHIYGTLLGASLSN
AGCGLPLKPHQPSEEACLKATYELVGVPPRDVQYVECHATGTPQGDTVELQA
VKACFEGASPRIGSTKGNFGHTLVAAGFAGMCKVLLAMERGVIPPTPGVDSG

FIG.4-17

TQIDPLVVTAALPWPDTRGGPKRAGLSAFGFGGTNAHAVFEEHIPSRA

SEQ ID NO: 22:

CAGCCTCGCCTCGGCAGCGGACCAAACCGAAAGCTTGCTATCGTCGGCA
TGGATGCCACGTTTGGATCCTTGAAGGGTCTCTCCGCACTAGAAGCTGCG
CTTTACGAGGCAAGGCACGCTGCGCGGCCCCTGCCTGCGAAGCGCTGGC
GCTTCTTGGGCGGGGACGAGTCCTTTCTCCACGAGATCGGACTCGAGTGC
TCTCCGCACGGGTGCTACATTGAGGACGTGGATGTGGACTTTAAGCGACT
CCGCACGCCAATGGTGCCGGAGGACTTGCTCCGGCCGCAACAGCTCCTG
GCCGTGTCGACGATTGACAAGGCCATCCTCGACTCGGGCTTGGCCAAGG
GCGGCAACGTGGCTGTCCTTGTCGGCCTCGGGACGGACCTCGAGCTCTAC
CGCCACCGAGCTCGGGTTGCGCTTAAGGAGCGTCTTCAAGGACTGGTTCG
CTCTGCCGAGGGAGGAGCCCTGACGTCTCGCCTGATGAACTATATCAATG
ATAGCGGAACGTCGACCTCCTACACGTCGTATATCGGCAACCTCGTCGCC
ACGCGCGTCTCGTCCCAGTGGGGCTTCACTGGGCCGTCGTTCACCGTCAC
GGAAGGGGCCAACTCGGTCCATCGGTGCGCCCAGCTCGCCAAGTACATG
CTCGACCGCGGCGAGGTCGACGCCGTCGTGGTTGCAGGAGTCGACCTGTG
CGGGAGCGCCGAGGCGTTCTTCGTGAGGTCGCGCCGCATGCAGATCTCGA
AAAGTCAGCGCCCGGCCGCGCCGTTTGACCGCGCCGCAGACGGCTTCTTC
GCGGGGGAAGGGTGCGGCGCCCTCGTCTTCAAACGCCTGACTGACTGTGT
GTCTGGCGAGCGAATCTACGCGTCCCTCGACTCGGTCGTCGTCGCAACCA
CGCCGCGCGCCGCTCTTCGTGCTGCCGCAGGGTCGGCGCGGGTTGACCCA
GCCAGCATCGACATGGTCGAGCTGAGCGCAGATTCCCACCGGTTTGTGCG
GGCGCCAGGCACCGTGGCTCAGCCTCTGACAGCCGAAGTCGAGGTCGGG
GCGGTGCGGGAAGTGATCGGGACCGCGGGGAGGGGCTCTCGAAGCGTGG
CCGTCGGATCGGTCCGCGCCAACGTCGGGGACGCAGGGTTTGCTTCCGGG
GCCGCTGCCCTCGTAAAAACTGCGCTCTGCTTGCACAACCGCTACTTGGC
GGCTACCCCAGGCTGGGATGCGCCTGCTGCCGGCGTGGATTTTGGTGCCG
AGCTGTACGTTTGCCGCGAGTCGCGTGCTTGGGTCAAGAACGCCGGCGTT
GCACGGCACGCCGCAATTTCTGGCGTGGACGAAGGCGGGTCG

SEQ ID NO:23:
QPRLGSGPNRKLAIVGMDATFGSLKGLSALEAALYEARHAARPLPAKRWRFL
GGDESFLHEIGLECSPHGCYIEDVDVDFKRLRTPMVPEDLLRPQQLLAVSTIDK
AILDSGLAKGGNVAVLVGLGTDLELYRHRARVALKERLQGLVRSAEGGALTS
RLMNYINDSGTSTSYTSYIGNLVATRVSSQWGFTGPSFTVTEGANSVHRCAQL
AKYMLDRGEVDAVVVAGVDLCGSAEFFVRSRRMQISKSQRPAAPFDRAAD
GFFAGEGCGALVFKRLTDCVSGERIYASLDSVVVATTPRAALRAAAGSARVDP
ASIDMVELSADSHRFVRAPGTVAQPLTAEVEVGAVREVIGTAGRGSRVAVGS
VRANVGDAGFASGAAALVKTALCLHNRYLAATPGWDAPAAGVDFGAELYV
CRESRAWVKNAGVARHAAISGVDEGGS

SEQ ID NO:24:
TGCTATGGGCTGGTTCTTTCGGACGTGCCTGGCAGTACGAGACCGGCAA

FIG.4-18

CCGCATCTCCCTCCAGGCCGAGTCGCCCAAGCTCTTGCTCCTCTCGGTCC
AGACCACGCCGCCTTGCTGGACAAGGTGGCGGCCGAGCTCGCAGCCCTT
GAGCAAGCCGACGGCTTGAGCGCCGCCGCGGCTGCCGTAGACCGCTTAC
TCGGCGAGTCGCTCGTCGGTTGCGCGGCTGGCAGCGGCGGGCTGACCCTT
TGCTTGGTGGCTTCGCCTGCCAGCCTCCACAAGGAGCTTGCGCTGGCCCA
TCGAGGGATCCCGCGCTGCATCAAAGCACGGCGCGACTGGGCCAGCCCG
GCAGGGAGCTACTTCGCCCCGGAGCCGATCGCAAGCGACCGCGTCGCGT
TCATGTACGGGGAAGGACGAAGCCCGTACTGCGGCGTCGGCCGCGACCT
CCACCGGATCTGGCCCGCGCTGCATGAGCGGGTGAACGCCAAGACTGTC
AACCTCTGGGGTGACGGTGACGCCTGGCTGCTGCCACGTGCAACCTCGGC
CGAGGAAGAGGAGCAACTCTGCCGCAACTTCGACTCGAACCAGGTTGAG
ATGTTTCGAACGGGCGTGTACATCTCGATGTGCTTGACCGACCTCGCTCG
AAGCTTGATTGGACTGGGCCCTAAGGCGAGCTTTGGGCTCAGCCTAGGCG
AGGTTTCCATGCTCTTCGCTCTGAGCGAGTCCAACTGTAGACTGTCGGAG
GAAATGACCCGCAGGCTCCGTGCGTCCCCGGTGTGGAACTCGGAGCTCG
CCGTCGAGTTCAACGCCCTTCGAAAGTTGTGGGGGGTCGCGCCGGGGGC
ACCCGTCGACTCGTTCTGGCAAGGTTATGTCGTGCGCGCAACGCGGGCTC
AGGTGGAGCAAGCCATTGGGGAGGACAATCAGTTTGTGCGTCTCCTGATC
GTGAACGACTCGCAATCAGTCCTGATCGCCGGCAAGCCGGCGGCGTGCG
AAGCCGTAATTGCTCGCATCGGGTCTATTCTTCCCCCGCTGCAAGTGTCGC
AAGGCATGGTGGGGCACTGTGCCGAGGTCTTGCCGTACACGAGCGAGAT
CGGGCGCATCCACAACATGCTTCGCTTCCCATCGCAGGACGAAACGGGC
GGTTGCAAAATGTACTCTAGCGTCTCAAACTCGCGCATCGGGCCAGTCGA
GGAGAGCCAGATGGGCCCAGGCACTGAGCTCGTTTTCTCGCCGTCAATGG
AAGACTTTGTCGCCCAGCTGTACTCGCGAGTTGCAGACTTTCCGGCGATC
ACCGAGGCGGTTTACCAGCAGGGTCATGACGTGTTTGTCGAAGTGGGGCC
GGACCATTCACGGTCGGCTGCTGTCCGCTCCACGCTTGGACCCACTCGGC
GACACATCGCTGTGGCGATGGACCGCAAGGGTGAGTCAGCTTGGTCGCA
GCTTCTGAAAATGCTGGCTACGCTTGCGTCGCACCGCGTGCCGGGCCTG

SEQ ID NO:25:
CYGLVLSDVPGQYETGNRISLQAESPKLLLLSAPDHAALLDKVAAELAALEQA
DGLSAAAAVDRLLGESLVGCAAGSGGLTLCLVASPASLHKELALAHRGIPR
CIKARRDWASPAGSYFAPEPIASDRVAFMYGEGRSPYCGVGRDLHRIWPALHE
RVNAKTVNLWGDGDAWLLPRATSAEEEQLCRNFDSNQVEMFRTGVYISMC
LTDLARSLIGLGPKASFGLSLGEVSMLFALSESNCRLSEEMTRRLRASPVWNSEL
AVEFNALRKLWGVAPGAPVDSFWQGYVVRATRAQVEQAIGEDNQFVRLLIV
NDSQSVLIAGKPAACEAVIARIGSILPPLQVSQGMVGHCAEVLPYTSEIGRIHN
MLRFPSQDETGGCKMYSSVSNSRIGPVEESQMGPGTELVFSPSMEDFVAQLYSR
VADFPAITEAVYQQGHDVFVEVGPDHSRSAAVRSTLGPTRRHIAVAMDRKGE
SAWSQLLKMLATLASHRVPGL

SEQ ID NO:26:
GCGACCATCCCTGAGGCCGTCGCAACAATTCTGCCGGCAACTGCTGCGAT
TCGCCTCCAAAGCTTGGCGCTCCGCACGACTCGCAACCCGAGGCGGAG

FIG.4-19

```
GCTCGCCCCGTGGGCGAGGCCTCTGTGCCAAGGCGGGCCACGAGCTCGA
GCAAATTGGCCAGGACGCTTGCCATCGATGCTTGCGACTCCGACGTGCGC
GCCGCCTTGCTGGACCTGGACGCGCCAATCGCGGTCGGCGGCTCCTCGCG
CGCCCAAGTCCCGCCGTGCCCAGTGAGCGCGCTCGGAAGCGCCGCCTTTC
GAGCGGCACACGGCGTCGATTATGCGCTCTACATGGGCGCAATGGCCAA
AGGCGTCGCGTCAGCGGAGATGGTCATCGCTGCTGGCAAGGCCCGCATG
CTCGCGTCATTTGGCGCGGGGGGGCTTCCCCTGGGCGAGGTCGAAGAGGC
GTTGGACAAGATCCAGGCCGCTCTGCCCGAGGGGCCGTTCGCCGTCAACC
TCATTCACTCGCCGTTCGATCCAAACCTTGAGGAGGGCAACGTCGAGCTG
TTCCTGAGGCGCGGTATCCGGCTGGTCGAGGCCTCTGCGTTCATGTCGGTC
ACGCCGTCGTTGGTGCGCTACCGAGTCGCCGGACTCGAGCGAGGCCTG
GCGGGACCGCCCGAGTGCTGAACCGCGTGATTGGCAAGGTGAGCCGTGC
GGAGCTCGCAGAAATGTTTATGCGGCCGCCTCCCGCCGCGATCGTCTCCA
AGCTCCTCGCCCAGGGCCTGGTCACTGAGGAGCAGGCGTCACTTGCAGA
GATCGTCCCACTGGTTGACGACGTTGCAATCGAAGCCGACTCGGGCGGTC
ACACAGACAACCGCCCGATCCACGTCGTTTTGCCCGTCGTCCTCGCGCTG
CGAGACCGCGTCATGCGTGAGTGCAAGTATCCAGCCGCCAATCGCGTCC
GCGTGGGCGCCGGAGGCGGGATCGGCTGCCCTGCCGCGGCGCGAGCTGC
GTTCGACATGGGCGCAGCATTCGTTCTCACGGGCTCGATCAACCAGCTCA
CGCGCCAGGCTGGGACGAGCGACAGCGTGCGTGCTGCCCTTGCACGCGC
GACCTACTCGGACGTGACAATGGCCCCGGCGGCCGATAGTTTGACCAG
GGCGTCAAGCTGCAGGTCTTGAAGCGCGGCACGATGTTCCCGGCGCGCG
CAAACAAGCTGTACGAGTTGTTCACCACTTACCAGTCGCTGGACGCGATC
CCTCGGGCTGAGCTGGCTCGCCTGGAAAAGCGAGTTTTCCGCATGTCCAT
CGACGAGGTTTGGAACGAAACCAAGCAGTTCTACGAGACCCGGCTCAAC
AACCCCGCCAAGGTTGCCCGGGCGGAGCGCGACCCCAAGCTCAAGATGT
CGCTCTGCTTTCGGTGGTACTTGTCGAAAAGCTCCAAGTGGGCATCGACT
GGACAAGTTGGGCGCGAGCTGGACTACCAGGTCTGGTGCGGCCCCACGA
TTGGCGCTTTCAACGAGTTCGTGAAGGGGTCCAGCCTCGACGCGGAGGCT
TGCGGGGGGCGGTTTCCTTGCGTTGTGCGCGTTAACCAGGAGATATTATG
TGGCGCTGCTTACGAGCAGCGACTGGCGCGTTTCATGCTGCTCGCTGGCC
GGGAAAGCGCGGACGCGTTGGCGTACACGGTTGCGGAAGCCAGATAG
```

SEQ ID NO:27:
ATIPEAVATILPATAAISPPKLGAPHDSQPEAEARPVGEASVPRRATSSSKLART
LAIDACDSDVRAALLDLDAPIAVGGSSRAQVPPCPVSALGSAAFRAAHGVDY
ALYMGAMAKGVASAEMVIAAGKARMLASFGAGGLPLGEVEEALDKIQAALP
EGPFAVNLIHSPFDPNLEEGNVELFLRRGIRLVEASAFMSVTPSLVRYRVAGLE
RGPGGTARVLNRVIGKVSRAELAEMFRPPPAAIVSKLLAQGLVTEEQASLAE
IVPLVDDVAIEADSGGHTDNRPIHVVLPVVLALRDRVMRECKYPAANRVRVG
AGGGIGCPAAARAAFDMGAAFVLTGSINQLTRQAGTSDSVRAALARATYSDV
TMAPAAMFDQGVKLQVLKRGTMFPARANKLYELFTTYQSLDAIPRAELARL
EKRVFRMSIDEVWNETKQFYETRLNNPAKVARAERDPKLKMSLCFRWYLSKS
SKWASTGQVGRELDYQVWCGPTIGAFNEFVKGSSLDAEACGGRFPCVVRVN
QEILCGAAYEQRLARFMLLAGRESADALAYTVAEAR

FIG.4-20

GENES INVOLVED IN POLYKETIDE SYNTHASE PATHWAYS AND USES THEREOF

BACKGROUND OF THE INVENTION

1. Technical Field

The subject invention relates to isolated nucleic acid sequences or genes involved in polyketide synthase (PKS) biosynthetic pathways. In particular, such pathways are involved in the production of polyunsaturated fatty acids (PUFAs) such as, for example, Eicosapentaenoic acid (EPA) and Docosahexaenoic acid (DHA). Specifically, the invention relates to isolating nucleic acid sequences encoding proteins involved in eukaryotic PUFA-PKS systems and to uses of these genes and encoded proteins in PUFA-PKS systems, in heterologous hosts, for the production of PUFAs such as EPA and DHA.

2. Background Information

Long chain polyunsaturated fatty acids (PUFAs) that contain 20 or 22 carbon atoms ($C_{20}$-, $C_{22}$-PUFAs) are essential components of membrane phospholipids and serve as precursors of eicosanoids like prostaglandin, leukotrienes and thromboxanes. They also play a pivotal role in various biological functions such as fetal growth and development, retina functioning and the inflammatory response. The n-6 fatty acids and the n-3 fatty acids are the two major classes of long chain PUFAs. In mammals, the major endpoint of the n-6 pathway is arachidonic acid (ARA, 20:4n-6), and the major endpoints of the n-3 pathway are eicosapentaenoic acid (EPA, 20:5n-3) and docosahexaenoic acid (DHA, 22:6n-3). n-6 and n-3 PUFAs are metabolically and functionally distinct, quite often having opposing physiological functions; thus, their balance is important for homeostasis. An excess of n-6 PUFAs shifts the physiological state to one that is prothrombotic and preaggregratory, leading to inflammatory and cardiovascular complications. On the other hand, n-3 PUFAs such as EPA and DHA have been shown to have therapeutic value in prevention and treatment of diseases such as, for example, cardiovascular disease, inflammation, arthritis and cancer. Thus, there is interest in identifying inexpensive and renewable sources of EPA and DHA.

A large number of lower eukaryotes like fungi and algae produce long chain PUFAs such as EPA and DHA. The exact mechanism of PUFA biosynthesis in these organisms is unknown but is presumed to be similar to that of mammals (i.e., an aerobic pathway involving an alternating series of desaturations and elongations catalyzed by a series of enzymes called desaturases and elongases). Many of these enzymes have already been identified in several of these PUFA-rich fungi such as *Thraustochytrium* sp., *Mortierella* sp., etc (Knutzon et al., *J. Biol. Chem* (1998) 273:29360–29366; Parker-Barnes et al., *Proc. Natl. Acad. Sci. USA*. (2000) 97:8284–8289; Huang et al., *Lipids* (1999) 34:649–659; Qiu et al., *J. Biol. Chem.* (2001) 276:31561–31566).

Recently, Metz et al. (*Science* (2001) 293: 290–293) proposed that DHA biosynthesis in *Schizochytrium*, an organism that belongs to the Thraustochytrid family, occurs via a novel polyketide synthase (PKS) pathway rather than the desaturase/elongase pathway (see also U.S. Pat. No. 6,566,583). This mechanism is thought to be similar to that used for EPA/DHA production in prokaryotes like *Shewanella* (Yazawa, *Lipids* (1996) 31 Suppl: S297–300) and *Vibrio* (Morita et al., *Biotechnol. Lett.* (1999) 21:641–646). In particular, PUFA production is initiated by the condensation between a short chain starter unit like acetyl CoA and an extender unit like malonyl CoA. The C4 acyl chain formed is covalently attached to an acyl carrier protein (ACP) domain of the PKS complex and goes through successive rounds of reduction, dehydration, reduction, and condensation, with the acyl chain growing by C2 units with each round. A novel dehydratase/isomerase has been proposed to exist in the complex (Metz et al., *Science* (2001) 293:290–293) that can catalyze trans- to cis-conversion of the double bonds, thus generating double bonds in the correct position of EPA and DHA.

The genes involved in the PUFA-PKS pathway have been identified from a number of marine organisms including *Shewanella*. In *Shewanella*, these genes were arranged in five open reading frames (ORFs) of ~20 kb in length and were shown to be sufficient for EPA production when tested in *E. coli* (Yazawa, *Lipids* (1996) 31 Suppl: S297–300). Examination of the protein sequences encoded by these five ORFs revealed that at least eleven enzymatic domains could be identified, seven of which were more strongly related to PKS proteins (Metz et al., *Science* (2001) 293:290–293) rather than to the fatty acid synthase (FAS) proteins that were suggested earlier (Watanabe et al., *J. Biochem.* (1997) 122:467).

It has been suggested that in *Shewanella*, at least some of the double bonds are introduced into EPA by a dehydratase-isomerase mechanism catalyzed by the fabA-like domain present in ORF 7 of the *Shewanella* PUFA-PKS cluster (Metz et al., *Science* (2001) 293:290–293). Expression studies of the *Shewanella* PKS gene cluster in *E. coli* revealed that EPA production could take place in the absence of oxygen indicating that the aerobic desaturase pathway did not play any role in EPA production in these marine bacteria. Thus, PUFA production in this marine bacteria is thought to occur via a novel PKS-like pathway and this is thought to be widespread in marine bacteria that make PUFAs, since genes with high homology to the *Shewanella* PUFA-PKS gene cluster have been identified in *Vibrio marinus* (Tanaka et al., *Biotechnol. Lett.* (1999) 21:939) and in *Photobacterium profundum* (Allen et al., *Appli. Environ. Microbiol.* (1999) 65:1710). The PKS pathways for PUFA synthesis in *Shewanella* and *Vibrio marinus* have been described in U.S. Pat. No. 6,140,486.

Genes homologous to the *Shewanella* PUFA-PKS gene cluster were recently identified in *Schizochytrium*, a marine eukaryote that produces DHA (Metz et al., *Science* (2001) 293: 290–293; see also U.S. Pat. No. 6,566,583). Labeling experiments with *Schizochytrium* demonstrated that DHA was produced solely from an acetate precursor, rather than from any $C_{18}$ fatty acid intermediate, pointing to the PKS-PUFA pathway as being functional in DHA production rather than the aerobic desaturase pathway.

Because of the increased demand for PUFAs such as EPA and DHA, alternate sources of these PUFAs are being sought after. The current natural sources of n-3 PUFAs such as fish oil are not economical or renewable and thus not suitable for commercial needs. Thus, the development of transgenic plant oils enriched with ω-3 PUFAs is currently being considered. For this, the plant will need to be genetically engineered to contain desaturase and elongase genes that are involved in EPA/DHA production. However, this would require expression of six to seven separate enzymes simultaneously in plants, and further manipulations might be necessary to control the flux through the pathway, target these genes to specific organelles, and/or modulate gene expression so as to prevent the accumulation of undesirable intermediates. Thus, it would be of interest to identify alternate PUFA biosynthesis pathways such as the PUFA-PKS pathway.

Although the bacterial PUFA-PKS genes do provide a novel resource for producing transgenic plant oils, it is not known how these bacterial genes will function in a eukaryotic host. Also, the source organisms for these genes grow in cold marine environments and their enzyme systems might not function well at or above 30° C. which could pose a problem for expression in some crops. Additionally, the PUFAs in these marine bacteria are not stored in the triglyceride form since these organisms are not oleaginous strains; thus, the PUFA-PKS system in these organisms cannot direct triglyceride formation. These shortcomings may be overcome by identifying additional PUFA-PKS genes from eukaryotic sources that make triglycerides. The identification of a PUFA-PKS gene cluster from *Schizochytrium*, fits this criteria. However, the amount of DHA produced by *Schizochytrium* is low compared to other *Thraustochytrid* species, and a large fraction of this DHA is found in the phospholipid fraction rather than in the triglyceride form (Kendrick et al., *Lipids* (1992) 27:15–20). Therefore, there is a need to identify other PUFA-PKS systems from eukaryotes that produce large amounts of DHA that is found in the triglyceride fraction, as well as EPA. *Thraustochytrium aureum* is an ideal candidate since this organism belongs to the same *Thraustochytrid* family as *Schizochytrium* does, but produces copious amounts of DHA (~30% of the total lipid is DHA) as compared to *Schizochytrium*, and has a major portion of its DHA in the triglycerol fraction (Kendrick et al., *Lipids* (1992) 27:15–20). Identification of the PUFA-PKS system from *Thraustochytrium aureum* provides an excellent alternative for the production of PUFA-enriched transgenic oils.

All U.S. patents and publications referred to herein are hereby incorporated in their entirety by reference.

SUMMARY OF THE INVENTION

The present invention encompasses an isolated nucleic acid sequence or fragment thereof comprising or complementary to a nucleic acid sequence encoding a polypeptide, wherein the amino acid sequence of said polypeptide has at least 65% amino acid identity to an amino acid sequence comprising SEQ ID NO:10.

Additionally, the present invention includes an isolated nucleic acid sequence or fragment thereof comprising or complementary to a nucleic acid sequence having at least 70% nucleotide sequence identity to a nucleic acid sequence comprising SEQ ID NO:8.

Further, the invention also encompasses an isolated nucleic acid sequence or fragment thereof comprising or complementary to a nucleic acid sequence encoding a polypeptide, wherein the amino acid sequence of said polypeptide has at least 65% identity to an amino acid sequence comprising SEQ ID NO:11.

Also, the present invention includes an isolated nucleic sequence or fragment thereof comprising or complementary to a nucleic acid sequence having at least 70% nucleotide sequence identity to a nucleic acid sequence comprising SEQ ID NO:9. Each of the nucleic acid sequences referred to above encodes a functionally active polyketide synthase enzyme. This enzyme modulates the production of at least one polyunsaturated fatty acid (PUFA) when expressed in a host cell. The PUFA may be, for example, eicosapentaenoic acid or docosahexaenoic acid. Further, each of the nucleic acid sequences may be isolated from, for example, *Thraus-tochytrium* sp. and, in particular, from *Thraustocytrium aureum*. The present invention also includes a protein or polypeptide encoded by any one or more of the above-described nucleic acid sequences or fragments thereof.

Additionally, the present invention also encompasses a purified protein or fragment thereof comprising an amino acid sequence having at least 65% amino acid identity to an amino acid sequence comprising SEQ ID NO:10 or SEQ ID NO:11.

Further, the invention includes a method of producing a polyketide synthase enzyme. This method comprises the steps of isolating a nucleic acid sequence comprising SEQ ID NO:8 or SEQ ID NO:9; constructing a vector comprising the isolated nucleic acid sequence operably linked to a regulatory sequence; and introducing the vector into a host cell under time and conditions sufficient for expression of the polyketide synthase enzyme. The host cell may be either a eukaryotic cell or a prokaryotic cell.

The present invention also encompasses a vector comprising a nucleic sequence comprising SEQ ID NO:8 or SEQ ID NO:9, operably linked to a regulatory sequence as well as a host cell comprising this vector. Again, the host cell may be either a eukaryotic cell or a prokaryotic cell.

Moreover, the present invention also includes a plant cell, plant or plant tissue comprising the above-described vector, wherein expression of the nucleic acid sequence of the vector results in production of at least one polyunsaturated fatty acid by the plant cell, plant or plant tissue. The at least one polyunsaturated fatty acid may be, for example, eicosapentaenoic acid (EPA) or docosahexaenoic acid (DHA). The invention also includes one or more plant oils or acids expressed by the plant cell, plant or plant tissue described above.

Additionally, the present invention includes a transgenic plant comprising the above-described vector, wherein expression of the nucleic acid sequence of the vector results in production of at least one polyunsaturated fatty acid in seeds of the transgenic plant.

Further, the present invention also includes a method for producing a polyunsaturated fatty acid. This method comprises the steps of isolating a nucleic acid sequence comprising SEQ ID NO:8 or SEQ ID NO:9; constructing a vector comprising the isolated nucleic acid sequence operably linked to a regulatory sequence; introducing the vector into a host cell for a time and under conditions sufficient for expression of a polyketide synthase enzyme encoded by the isolated nucleic acid sequence; exposing the polyketide synthase enzyme to a substrate to produce a product; and exposing the product to at least one enzyme selected from the group consisting of a ketosynthase, a ketoreductase, a dehydratase, an isomerase, an enoyl reductase, a desaturase and an elongase in order to produce the polyunsaturated fatty acid. The substrate may be, for example, acetyl-CoA malonyl-CoA, malonyl-ACP, methylmalonyl-CoA or methylmalonyl-ACP. The polyunsaturated fatty acid may be, for example, EPA or DHA. The invention also includes a composition comprising at least one polyunsaturated fatty acid produced according to the above-described method. In the composition, the at least one polyunsaturated fatty acid may be, for example, EPA or DHA.

BRIEF DESCRIPTION OF THE DRAWINGS

FIG. 1 illustrates a comparison of the predicted amino acid sequence of the *Thraustochytrium aureum* probe 'TA- PKS-1-consensus' and the homologous region on ORF A of the *Schizochytrium* gene cluster (Accession number AAK72879).

FIG. 2 illustrates a comparison of the predicted amino acid sequence of the *Thraustochytrium aureum* probe 'TA-PKS-1-consensus' and the homologous region on ORF 5 of the *Shewanella* PKS gene cluster (Accession number AAB81123).

FIG. 3 represents the organization of ORFA and ORFB of the PUFA-PKS genes from *Thraustochytrium aureum* (ATCC 34304). (KS=β-keto acyl synthase; MAT=MalonylCoA transferase; ACP=Acyl carrier protein; KR=Ketoacyl-ACP reductase; AT=Acyl transferase; CLF=Chain length factor; ER=Enoyl reductase; DH=Dehydratase)

FIG. 4 illustrates all of the sequences and corresponding sequence identifier numbers referred to herein.

DETAILED DESCRIPTION OF THE INVENTION

The subject invention relates to isolated nucleic acid sequences or molecules (and the proteins encoded thereby) involved in PKS pathways and thus in the production of polyunsaturated fatty acids (PUFAs) such as DHA and EPA. Such PUFAs may be added to, for example, pharmaceutical and nutritional compositions. Furthermore, the subject invention also includes uses of the cDNAs and of the proteins encoded by the genes.

The Nucleic Acid Sequences of the Two Genes (Open Reading Frames A and B) and the Encoded Proteins The nucleic acid sequence of the first isolated gene (ORF A) from *T. aureum* ATCC 34304 is shown in FIG. 4 (SEQ ID NO:8), and the amino acid sequence of the encoded purified protein or enzyme encoded by this nucleic acid sequence is also shown in FIG. 4 (SEQ ID NO:10). Additionally, the nucleic acid sequence of the second isolated gene (ORF B) from *T. aureum* ATCC 34304 is shown in FIG. 4 (SEQ ID NO:9), and the amino acid sequence of the purified protein encoded by this nucleic acid sequence is also shown in FIG. 4 (SEQ ID NO:11).

It should be noted that the present invention also encompasses nucleic acid sequences or molecules (and the corresponding encoded proteins) comprising nucleotide sequences which are at least about at least about 65% identical to, preferably at least about 70% identical to, more preferably at least about 80% identical to, and most preferably at least about 90% identical to the nucleotide sequence of SEQ ID NO:8. Further, the present invention also includes nucleic acid sequences or molecules (and the corresponding encoded proteins) comprising nucleotide sequences which are at least about 65% identical to, preferable at least about 70% identical to, more preferably at least about 80% identical to, and most preferably at least about 90% identical to the nucleotide sequence of SEQ ID NO:9. Complements of these sequences are also encompassed by the present invention. (All integers within the range of 65 to 100 (in terms of percent identity) are also included within the scope of the invention.)

The sequences having the above-described percent identity (or complementary sequences) may be derived from one or more sources other than *T. aureum* (e.g., other eukaryotes (e.g., *Thraustochytrium* spp. (e.g., *Thraustochytrium roseum*)), *Schizochytrium* spp. (e.g., *Schizochytrium aggregatum*), *Conidiobolus* spp. (e.g., *Conidiobolus nanodes*), *Entomorphthora* spp. (e.g., *Entomorphthora exitalis*), *Saprolegnia* spp. (e.g., *Saprolegnia parasitica* and *Saprolegnia diclina*), *Leptomitus* spp. (e.g., *Leptomitus lacteus*), *Entomophthora* spp., *Pythium* spp., *Porphyridium* spp. (e.g., *Porphyridium cruentum*), *Conidiobolus* spp., *Phytophathora* spp., *Penicillium* spp., *Coidosporium* spp., *Mucor* spp. (e.g., *Mucor circinelloides* and *Mucor javanicus*), *Fusarium* spp., *Aspergillus* spp., *Rhodotorula* spp., *Amphidinium carteri*, *Chaetoceros calcitrans*, *Cricosphaera carterae*, *Crypthecodinium cohnii*, *Cryptomonas ovata*, *Euglena gracilis*, *Gonyaulax polyedra*, *Gymnodinium* spp. (e.g. *Gymnodinium nelsoni*), *Gyrodinium cohnii*, *Isochrysis* spp. (e.g. *Isochrysis galbana*), Microalgae MK8805, *Nitzschia frustulum*, *Pavlova* spp. (e.g., *Pavlova lutheri*), *Phaeodactylum tricornutum*, *Prorocentrum cordatum*, *Rhodomonas lens*, and *Thalassiosira pseudonana*), a *Psychrophilic* bacteria (e.g., *Vibrio* spp. (e.g., *Vibrio marinus*)) and a yeast (e.g., *Dipodascopsis uninucleata*.

Furthermore, the present invention also encompasses fragments and derivatives of the nucleic acid sequences of the present invention (i.e., SEQ ID NO:8 (ORF A) and SEQ ID NO:9 (ORF B)) as well as of the corresponding sequences derived from non-*T. aureum* sources, as described above, and having the above-described complementarity or identity. Functional equivalents of the above-sequences (i.e., sequences having polyketide synthase activity) are also encompassed by the present invention.

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appi. Math. 2:482 (1981), by the algorithm of Needleman & Wunsch, *J. Mol. Biol.* 48:443 (1970), by the method of Pearson & Lipman, *Proc. Natl. Acad. Sci.* (USA) 85:2444 (1988) and by computer programs which implement the relevant algorithms (e.g., Higgins et al., CABIOS. 5L151–153 (1989)), FASTDB (Intelligenetics), BLAST (National Center for Biomedical Information; Altschul et al., Nucleic Acids Research 25:3389–3402 (1997)), PILEUP (Genetics Computer Group, Madison, Wis.) or GAP, BEST-FIT, FASTA and TFASTA (Wisconsin Genetics Software Package Release 7.0, Genetics Computer Group, Madison, Wis.) (See U.S. Pat. No. 5,912,120.)

"Identity between two amino acid sequences is defined as the presence of a series of exactly alike or invariant amino acid residues in both sequences (see above definition for identity between nucleic acid sequences). The definitions of "complementarity" and "identity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleic sequence which encodes a protein having polyketide synthase activity and that is hybridizable, under moderately stringent conditions, to a nucleic acid having a nucleotide sequence comprising or complementary to the nucleotide sequences described above. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity, identity or homology between two nucleotide sequences, the greater the value of Tm for hybrids of nucleic acids having those sequences. For hybrids of greater than 100 nucleotides in length, equations for calculating Tm have been derived (see Sambrook et al., supra (1989)). For hybridization with shorter nucleic acids, the position of mismatches becomes more important, and the length of the oligonucleotide determines its specificity (see Sambrook et al., supra (1989)).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" (or "regulatory sequence") refers to a DNA sequence capable of controlling the expression of a coding sequence or functional RNA. The promoter sequence, for example, consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Regulatory sequences (e.g., a promoter) can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most host cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the gene sequence that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

"Stable transformation" refers to the transfer of a nucleic acid fragment into a genome of a host organism, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature (London)* 327:70–73; U.S. Pat. No. 4,945,050), or an *Agrobacterium*-mediated method using an appropriate Ti plasmid containing the transgene (Ishida et al. (1996) Nature Biotech. 14:745–750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al., Cold Spring Harbor Symp. Quant. Biol. 51:263–273 (1986); Erlich et al., European Patent Application 50,424; European Patent Application 84,796; European Patent Application 258,017, European Patent Application 237,362; European Patent Application 201,184, U.S. Pat. No. 4,683,202; U.S. Pat. No. 4,582,788; and Saiki et al. and U.S. Pat. No. 4,683,194). The process utilizes sets of specific in vitro synthesized oligonucleotides to prime DNA synthesis. The design of the primers is dependent upon the sequences of DNA that are to be analyzed. The technique is carried out through many cycles (usually 20–50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such a construct may be itself or may be used in conjunction with a vector. If a vector is used, then the choice of vector is dependent upon the method that will be used to transform host plants, as is well known to those skilled in the art. For example, a plasmid can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411–2418; De Almeida et al., (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

With respect to "polyketides", these entities are secondary metabolites that are synthesized via a series of enzymatic reactions and are analogous to enzymes of the fatty acid synthase (FAS) complex (Hopwood et al., (1990) Annual Rev. Genet. 24:37–66). In particular, the enzymes involved in polyketide biosynthesis are called "polyketide synthase enzymes". For purposes herein, "a functionally active polyketide synthase enzyme" is defined as an enzyme or protein involved in the production of polyunsaturated fatty acids such as, for example, eicosapentaenoic acid and docosahexaenoic acid via a polyketide-like (PKS-like) pathway (such as described for the production of PUFAs by prokaryotes like Shewanella and Vibrio, and the eukaryote Schizochytrium (see U.S. Pat. No. 5,683,898, U.S. Pat. No. 6,140,486 and U.S. Pat. No. 6,566,583)).

Production of the Polyketide Synthase Enzymes

Once the gene encoding the polyketide synthase enzyme has been isolated, it may then be introduced into either a prokaryotic or eukaryotic host cell, through the use of a vector or construct, in order for the host cell to express the protein of interest. The vector, for example, a bacteriophage, cosmid or plasmid, may comprise the nucleic acid sequence encoding the enzyme, as well as any regulatory sequence (e.g., promoter) that is functional in the host cell and is able to elicit expression of the enzyme encoded by the nucleic acid sequence. The regulatory sequence (e.g., promoter) is in operable association with or operably linked to the nucleotide sequence. (A regulatory sequence (e.g., promoter) is said to be "operably linked" with a coding sequence if the regulatory sequence affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, promoters activated in the presence of galactose, for example, GAL1 and GAL10, as well as any other promoters involved in prokaryotic and eukaryotic expression systems. Additionally, nucleic acid sequences which encode other proteins, oligosaccharides, lipids, etc., may also be included within the vector as well as other non-promoter regulatory sequences such as, for example, a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see Molecular Cloning: A Laboratory Manual, $2^{nd}$ ed., Vol. 1–3, ed. Sambrook et al., Cold Spring Harbor Laboratory Press (1989)). The host cell is then cultured under suitable conditions permitting expression of the PUFA that is then recovered and purified.

It should also be noted that one may design a unique triglyceride or oil if one utilizes one construct or vector comprising the nucleotide sequences of two or more genes. This vector may then be introduced into one host cell. Alternatively, each of the sequences may be introduced into a separate vector. These vectors may then be introduced into two host cells, respectively, or into one host cell.

Examples of suitable prokaryotic host cells include, for example, bacteria such as Escherichia coli, Bacillus subtilis, Actinomycetes such as Streptomyces coelicolor, Streptomyces lividans, as well as cyanobacteria such as Spirulina spp. (i.e., blue-green algae). Examples of suitable eukaryotic host cells include, for example, mammalian cells, plant cells, yeast cells such as Saccharomyces spp., Lipomyces spp., Candida spp. such as Yarrowia (Candida) spp., Kluyveromyces spp., Pichia spp., Trichoderma spp. or Hansenula spp., or fungal cells such as filamentous fungal cells, for example, *Aspergillus, Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzyme of interest (i.e., the polyketide synthase enzyme) encoded by one or both of the above-described nucleic acid sequences. More specifically, once the above-described construct is created, it may be inserted into the pronucleus of an embryo. The embryo may then be implanted into a recipient female. Alternatively, a nuclear transfer method could also be utilized (Schnieke et al., *Science* (1997) 278:2130–2133). Gestation and birth are then permitted to occur (see, e.g., U.S. Pat. No. 5,750,176 and U.S. Pat. No. 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene or genes encoding the polyketide synthase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of a polyketide synthase polypeptide, functional transcriptional and translational initiation and termination regions are operably linked to the DNA encoding the polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379. Alternatively, the expressed protein can be an enzyme that produces a product that may be incorporated, either directly or upon further modifications, into a fluid fraction from the host plant. Expression of a polyketide synthase gene or genes, or antisense polyketide synthase transcripts, can alter the levels of specific PUFAS, or derivatives thereof, found in plant parts and/or plant tissues. The polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)), plant cell, plant tissue, corn, potato, sunflower, safflower or flax may also be utilized as a host or host cell, respectively, for expression of the polyketide synthase enzyme(s) which may, in turn, be utilized in the production of polyunsaturated fatty acids. More specifically, desired PUFAs can be expressed in seed. Methods of isolating seed oils are known in the art. Thus, in addition to providing a source for PUFAs, seed oil components may be manipulated through the expression of the polyketide synthase genes, in order to provide seed oils that can be added to nutritional compositions, pharmaceutical compositions, animal feeds and cosmetics. Once again, a vector that comprises a DNA sequence encoding the polyketide synthase enzyme operably linked to a promoter, will be introduced into the plant tissue or plant for a time and under conditions sufficient for expression of the polyketide synthase gene. The vector may also comprise one or more genes which encode other enzymes, for example, elongases, $\Delta$4-desaturase, $\Delta$5-desaturase, $\Delta$6-desaturase, $\Delta$8-desaturase, $\Delta$9-desaturase, $\Delta$10-desaturase, $\Delta$12-desaturase, $\Delta$13-desaturase, $\Delta$15-desaturase, $\Delta$17-desaturase and/or $\Delta$19-desaturase. The plant tissue or plant may produce the relevant substrate (e.g., DGLA, GLA, STA, AA, ADA, EPA, 20:4n-3, etc.) upon which the enzymes act or a vector encoding enzymes which produce such substrates may be introduced into the plant tissue, plant cell, plant, or host cell of interest. In addition, substrate may be sprayed on plant tissues expressing the appropriate enzymes. Using these various techniques, one may produce PUFAs (e.g., n-3 fatty acids such as EPA or DHA) by use of a plant cell, plant tissue, plant, or host cell of interest. It should also be noted that the invention also encompasses a transgenic plant comprising the above-described vector, wherein expression of the nucleotide sequence of the vector results in production of a polyunsaturated fatty acid in, for example, the seeds of the transgenic plant.

The substrates which may be produced by the host cell either naturally, transgenically or exogenously supplied (e.g., acetyl-CoA, malonyl-CoA, malonyl-ACP, methylmalonyl-CoA and methylmalonyl-ACP), as well as the enzymes which may be encoded by DNA sequences introduced in the vector (e.g., polyketide synthase (i.e., $\beta$-ketoacyl synthase (or ketoacyl synthase), ketoreductase, dehydratase, and enoyl reductase), which is subsequently introduced into the host cell, in which EPA and/or DHA is produced. It should be noted that the host cell may produce some of the enzymes (i.e., ketosynthase, ketoreductase, dehydratase and enoyl reductase) endogenously if the PKS genes are expressed individually on different expression vectors.

With respect to the encoded polyketide synthase proteins, it should be noted that the present invention not only encompasses the amino acid sequence of the protein shown in SEQ ID NO:10 but also encompasses proteins comprising amino acid sequences which are at least about 65% identical to, preferably at least about 75% identical to, more preferably at least about 85% identical to and most preferably at least 95% identical to the amino acid sequence shown in SEQ ID NO:10. (All integers within the range of 65 to 100 (in terms of percent identity) are also included within the scope of the invention.) Further, the present invention also encompasses the amino acid sequence of the protein shown in SEQ ID NO:11 as well as all proteins comprising amino acid sequences which are at least about 60% identical to, preferably at least about 70% identical to, more preferably at least about 80% identical to and most preferably at least 90% identical to the amino acid sequence shown in SEQ ID NO:11. (All integers within the range of 60 to 100 (in terms of percent identity) are also included within the scope of the invention.)

In view of the above, the present invention also encompasses a method of producing one or more of the polyketide synthase enzymes described above comprising the steps of: 1) isolating the desired nucleic acid sequence(s) of the gene encoding the synthase(s) (i.e., SEQ ID NO:8 and/or SEQ ID NO:9; 2) constructing a vector comprising said nucleic acid sequence(s); and 3) introducing said vector into a host cell under time and conditions sufficient for the production of the polyketide synthase enzyme(s).

The present invention also encompasses a method of producing polyunsaturated fatty acids comprising exposing the initial substrates (e.g., acetyl CoA, malonyl CoA, malonyl-ACP, methylmalonyl-CoA and methylmalonyl-ACP) to one or more of the polyketide synthase enzymes described above such that the polyketide synthase converts the initial substrates to a polyunsaturated fatty acid (i.e., EPA or DHA), when additional enzymes are utilized. For example, endogenous acetyl CoA and malonyl CoA (which are found in every cell) are initially condensed by one or more of the polyketide synthases of the present invention. A four-carbon unit fatty acid chain is then formed. In the process, one carbon is lost as carbon dioxide. Subsequently, the four-carbon unit goes through a reduction catalyzed by ketoreductase, dehydration catalyzed by dehydratase, and perhaps another reduction catalyzed by enoyl reductase. Then, the four carbon fatty acid chain is thought to go through repeat cycles and gets extended by two carbons with each cycle until the chain eventually reaches 20 carbon (EPA) or 22 carbons (DHA).

The exact mechanism for the insert of cis double bonds into EPA/DHA is not known but this has been proposed through the action of a bifunctional dehydratase/2-trans, 3-cis isomerase (DH/2,3I) as seen in *E. coli* (Metz et al., *Science* (2001) 293:290–293). Since the PKS cycle extends the chain in two-carbon increments, while the double bond in EPA occurs every third carbon, it has been proposed that the double bonds at carbon atom 14 and carbon atom 8 of EPA are generated by a bifunctional dehydratase/2-trans,2 cis isomerase (DH/2,2I). This is followed by the incorporation of a cis double bond into the elongating fatty acyl chain (Metz et al., *Science* (2001) 293:290–293).

Uses of the PUFA-Polyketide Synthase Genes and Enzymes Encoded Thereby

As noted above, the isolated nucleic acid sequences (or genes) and the corresponding encoded polyketide synthase enzymes (or purified polypeptides) encoded thereby have many uses. For example, each nucleic acid sequence and corresponding encoded enzyme may be used in the production of polyunsaturated fatty acids, for example, EPA and DHA, as mentioned above. These polyunsaturated fatty acids (i.e., those produced by activity of the polyketide synthase enzyme(s)) may be added to, for example, nutritional compositions, pharmaceutical compositions, cosmetics, and animal feeds, all of which are encompassed by the present invention. Additionally, this system may be used in combination with other genes involved in PUFA biosynthesis such as, for example, the desaturases and elongases involved in DHA production (e.g., Δ4-desaturase and C20-elongase) or related enzymes. Several of these uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced by use of at least one polyketide synthase enzyme, produced using the respective polyketide synthase gene, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed starch. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions. Nutritional compositions of particular interest include but are not limited to those utilized for enteral and parenteral supplementation for infants, specialist infant formulae, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio). An oil or fatty acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substance boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight % of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as AA, from about 0.22% to about 0.67% as DGLA, and from about 0.27% to about 1.04% as GLA. Thus, fatty acids such as DGLA, AA, EPA and/or docosahexaenoic acid (DHA), produced in accordance with the present invention, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of AA, DGLA and GLA. More preferably, the oil blend will comprise from about 0.3 to 30% AA, from about 0.2 to 30% DGLA, and/or from about 0.2 to about 30% GLA.

Parenteral nutritional compositions comprising from about 2 to about 30 weight percent fatty acids calculated as triglycerides are encompassed by the present invention. The preferred composition has about 1 to about 25 weight percent of the total PUFA composition as GLA (U.S. Pat. No. 5,196,198). Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of AA, DGLA and GLA can be adapted for a particular given end use. When formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to AA can be used to precisely control the PUFA ratios. For example, a 5% to 10% conversion rate of DGLA to AA can be used to produce an AA to DGLA ratio of about 1:19, whereas a conversion rate of about 75% to 80% can be used to produce an AA to DGLA ratio of about 6:1. Therefore, whether in a cell culture system or in a host animal, regulating the timing, extent and specificity of elongase expression, as well as the expression of other desaturases, can be used to modulate PUFA levels and ratios. The PUFAs/acids produced in accordance with the present invention (e.g., AA and DGLA) may then be combined with other PUFAs/acids (e.g., GLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the fatty acids and/or resulting oils produced using at least one of the polyketide synthase genes in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% of AA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the PUFAs produced using the polyketide synthase enzymes of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., Am. J. Clin. Nutr. Vol. 57 (Suppl.) 732S–737S). Altered fatty acid metabolism and composition have been demonstrated in diabetic animals.

Furthermore, the compositions of the present invention comprising PUFAs produced either directly or indirectly through the use of the polyketide synthase enzyme(s), may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., Adv. Exp. Med. Biol. Vol. 83, p. 85–101, 1976), reduction or prevention of gastrointestinal bleeding and other side effects of non-steroidal anti-inflammatory drugs (see U.S. Pat. No. 4,666, 701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention, the PUFAs of which are produced by use of the polyketide synthase enzymes of the present invention, include use in the treatment of AIDS, multiple sclerosis, and inflammatory skin disorders, as well as for maintenance of general health.

Veterinary Applications

It should be noted that the above-described PUFA-containing pharmaceutical and nutritional compositions may be utilized in connection with animals (i.e., domestic or non-domestic), as well as humans, as animals experience many of the same needs and conditions as humans. For example, the oil or acids produced using the polyketide synthase enzymes of the present invention may be utilized in animal feed supplements, animal feed substitutes, animal vitamins or in animal topical ointments.

The present invention may be illustrated by the use of the following non-limiting examples:

EXAMPLE I

Construction of BAC Library from *Thraustochytrium aureum* (ATCC 34304)

*Thraustochytrium aureum* (ATCC 34304) is an organism that produces copious amounts of polyunsaturated fatty acids (PUFAs) such as DHA which can amount to ~30%–40% of its total fatty acid, a major portion of which appears in its triacylglyceride fraction. This organism belongs to the Thraustochytrid family of marine organisms, which include organisms like *Schizochytrium, Ulkenia, Aplanochytrium* etc, many of which make DHA. Recent studies with *Schizochytrium* have revealed the presence of polyketide synthase (PKS) gene clusters that are involved in DHA biosynthesis (Metz et al., *Science* (2001) 293:290–293; U.S. Pat. No. 6,566,583), similar to the PKS gene clusters seen in the EPA- and DHA-producing prokaryotes like *Shewanella* (Yazawa, K., (1996) *Lipids* 31 Suppl.: S297–300) and *Vibrio* (Morita et al., (1999) *Biotechn. Lett.* 21:641–646). Since *Thraustochytrium aureum* and *Schizochytrium* belong to the same family, it was thought that perhaps a similar set of PKS genes might exist in *Thraustochytrium aureum* that are involved in DHA biosynthesis.

To identify the PKS genes involved in EPA/DHA production in *T. aureum*, genomic libraries were constructed in the BAC vectors, TrueBlue-BAC2 (Genomics One, Inc., Quebec, Canada), or pCC1BAC (Epicenter, Madison, Wis.) and screened with PKS gene probes. For the construction of BAC libraries, high molecular weight genomic DNA was needed. The isolation of this high molecular weight genomic DNA from *T. aureum* was carried out as follows: Frozen fungal pellets were crushed in liquid nitrogen, mixed with Tris-saturated phenol:TE (1:1), and incubated for 10 min at room temperature (RT). The mixture was centrifuged at 6000 rpm for 10 min at RT, after which the aqueous phase was mixed with an equal volume of chloroform: isoamyl alcohol (24:1), and centrifuged as before. The DNA from the aqueous phase thus obtained was precipitated with 0.6 volumes of isopropanol, spun at 13,000 rpm for 20 min, and the pellet thus obtained washed with 70% ethanol, dissolved in TE (pH 8) and then treated with RNase A. The genomic DNA (gDNA) was purified by extractions with phenol: chloroform:isoamyl alcohol (25:24:1), followed by chloroform:isoamyl alcohol (24:1) extraction. The DNA in the aqueous phase was precipitated with 2.5 volumes of ethanol, spun down and washed with ethanol as mentioned earlier. The quality of the isolated gDNA was analyzed by pulsed field gel electrophoresis (PFGE) (CHEF; Amersham Pharmacia, Piscataway, N.J.). The gDNA thus isolated was ~150–200 Kb in size and did not show much shearing.

The purified gDNA was partially digested using ClaI for a time interval of 5 min to 40 min to give a desired size range of 30–40 kb, and digested DNA was separated on a 1.2% low melting temperature agarose pulse field gel electrophoresis (PFGE) gel. The appropriate sized fractions were excised from the low melting agarose PFGE, eluted from the excised gel, and precipitated using LiCl/Glycogen. The DNA thus obtained was purified by ethanol precipitation as described previously. The size range of the fractions was confirmed on PFGE.

For construction of the BAC library, the TrueBlue-BAC2 vector (Genomics One, Inc., Quebec, Canada) was linearized with ClaI, dephosphorylation with Calf Intestinal Alkaline Phosphatase, and ligated to the ClaI digested gDNA insert in a molar ratio of 1:5. Ligation was carried out for 16 h at 16° C., followed by transformation into Electromax DH10B *E. coli* competent cells (Invitrogen, Carlsbad, Calif.). Colonies were grown on selective media containing 25 µg/ml chlormaphenicol, 0.03 mM IPTG and 0.003% Xgal and incubated overnight at 37° C. The average insert size of the library was ~32 kb, library size was $4.8 \times 10^3$, with a vector background of 24%.

A BAC library was also constructed in pCC1BAC vector (Epicenter, Madison, Wis.). Here, the BAC vector was digested with BamHI, dephosphorylation with Calf Intestinal Alkaline Phosphatase, and ligated to the BamHI partially digested gDNA insert in a molar ratio of 1:5. Following ligation, EPI300 *E. coli* electrocompetent cells (Epicenter, Madison, Wis.) were transformed, and transformants grown on selective media containing 12.5 µg/ml Chloramphenicol, 0.4 mM isopropylthiogalactoside (IPTG) and 40 µg/ml Xgal and incubated overnight at 37° C. The average insert size of the library was ~50 kb, library size was $10^4$, with a vector background of 2%.

Example II

Identification of PKS Gene Probes from *Thraustochytrium aureum* (ATCC 34304) for Colony Hybridization Some of the PKS probes used for the screening of the BAC libraries were identified by random sequencing of a cDNA library constructed from *T. aureum*. The cDNA library was constructed as follows: *T. aureum* (ATCC 34304) cells were grown in BY+ Media (#790, Difco, Detroit, Mich.) at room temperature for 4 days, in the presence of light, and with constant agitation (250 rpm) to obtain the maximum biomass. These cells were harvested by centrifugation at 5000 rpm for 10 min. and rinsed in ice-cold RNase-free water. These cells were then lysed in a French Press at 10,000 psi, and the lysed cells were directly collected into TE buffered phenol. Proteins from the cell lysate were removed by repeated phenol: chloroform (1:1 v/v) extraction, followed by a chloroform extraction. The nucleic acids from the aqueous phase were precipitated at –70° C. for 30 minutes using 0.3M (final concentration) sodium acetate (pH 5.6) and one volume of isopropanol. The precipitated nucleic acids were collected by centrifugation at 15,000 rpm for 30 minutes at 4° C., vacuum-dried for 5 minutes and then treated with DNaseI (RNase-free) in 1× DNase buffer (20 mM Tris-Cl, pH 8.0; 5 mM $MgCl_2$) for 15 minutes at room temperature. The reaction was quenched with 5 mM EDTA (pH 8.0) and the RNA further purified using the Qiagen RNeasy Maxi kit (Qiagen, Valencia, Calif.) as per the manufacturer's protocol.

Messenger RNA (mRNA) was isolated from total RNA using oligo dT cellulose resin, and the pBluescript II XR library construction kit (Stragene, La Jolla, Calif.) was used to synthesize double stranded cDNA which was then directionally cloned (5' EcoRI/3' XhoI) into pBluescript II SK(+) vector (Stragene, La Jolla, Calif.). The *T. aureum* library contained approximately $2.5 \times 10^6$ clones, each with an average insert size of approximately 700 bp.

Random sequencing of this library was carried out on five thousand primary clones which sequenced from the 5' end using the M13 forward primer (5'-AGC GGA TAA CAA TTT CAC ACA GG-3' [SEQ ID NO:1]). Sequencing was carried out using the ABI BigDye sequencing kit (Applied Biosystems, CA) and the MegaBase Capillary DNA sequencer (Amersham Biosciences, Piscataway, N.J.). The predicted protein sequences of the library were compared with the predicted protein sequences present in the public database (Genbank) using the NCBI BLASTX program.

Three contigs (Contig 53 [SEQ ID NO:2], Contig 58 [SEQ ID NO:3], and Contig 1763 [SEQ ID NO:4]) were thus identified from the cDNA library sequencing data, which shared homology with regions from published PUFA-PKS genes from *Shewanella* and *Schizochytrium* (Table 1). Sequence comparison of the predicted protein sequences were carried out using the 'BestFit' program in GCG (GCG Wisconsin Package, Madison, Wis.).

TABLE 1

Identification of Regions in *T. aureum* With Homology to *Shewanella* PUFA-PKS Genes and *Schizochytrium* PUFA-PKS Genes

| Contig # | Length of clone | Location | % Amino Acid Identity (*Shewanella*) | % Amino acid Identity (*Schizochytrium*) |
|---|---|---|---|---|
| 53 | 713 bp | Region upstream of Ketoacyl reductase (KR) *Shewanella*-ORF 5 *Schizochytrium*-ORF A | 41% in 246 aa overlap | 36% in 239 aa overlap |
| 58 | 1023 bp | Region downstream of Ketoacyl reductase (KR) *Shewanella*-ORF 5 *Schizochytrium*-ORF A | 32% in 231 aa overlap | 43% in 262 aa overlap |
| 1763 | 1240 bp | Enoyl Reductase (ER) *Shewanella*-ORF 8 *Schizochytrium*-ORF B | 52% in 312 aa overlap | 75% in 329 aa overlap |

Since Contig 53 and Contig 58 were predicted to lie on one open reading frame (ORF) of the PKS cluster, the region between the two contigs which would include the Ketoacyl reductase gene was amplified by PCR using the following primers:

(forward primer) RO 1447 (5'-CTTGTGCAAGAC CTTG-GACCTAGAG-3'[SEQ ID NO:5]) based on the sequence of Contig 53;

(reverse primer) RO 1448 (5'-GAACCTCATCCATGTACT-GAAACGC-3') [SEQ ID NO:6] based on the sequence of Contig 58.

PCR amplification was carried out using 2 µl of *T. aureum* genomic DNA as a template in a 50 µl total volume containing: PCR buffer [40 mM Tricine-KOH (pH 9.2), 15 mM KOAc, 3.5 mM Mg(OAc)$_2$, 3.75 µg/ml BSA (final concentration)], 200 µM each deoxyribonucleotide triphosphate, 10 pmole of each primer and 0.5 µl of "Advantage"-brand cDNA polymerase (Clonetech, Palo Alto, Calif.). Amplification was carried out as follows: initial denaturation at 94° C. for 3 minutes, followed by 35 cycles of the following: 94° C. for 1 min, 60° C. for 30 sec, 72° C. for 1 min. A final extension cycle of 72° C. for 7 min was carried out, followed by reaction termination at 4° C. The ~1.56 kb PCR product thus produced was labeled 'TA-PKS-1-consensus' or 'TA-PKS-1-1' (SEQ ID NO:7) and was used as a probe for screening the BAC clones to identify clones containing the PKS ORF A region. The predicted protein encoded by TA-PKS 1-1 displayed 52.8% amino acid identity with the homologous region in the *Schizochytrium* ORF A (FIG. 1), and 39.9% amino acid identity with the homologous region in ORF 5 of the *Shewanella* PKS gene cluster (FIG. 2), as estimated by using the BestFit program (GCG, Madison, Wis.). In addition, attempts were made to PCR amplify regions of the PKS cluster corresponding to the β-ketoacyl synthase, malonyl CoA transferase, and the acyl transferase, using degenerate primers that contained conserved motifs shared by PKS genes from *Schizochytrium* (Metz et al., *Science* (2001) 293:290–293), *Shewanella* (Yazawa, K., *Lipids* (1996) 31 Suppl.: S297–300), *Vibrio* (Morita et al., *Biotechnol. Lett.* (1999) 21:641–646) and *Photobacterium* (Allen et al., *Microbiology* (2002) 148: 1903–1913). However these attempts were unsuccessful.

To identify BAC clones containing the additional sequences present in the PUFA PKS cluster, the Contig 1763 (SEQ ID NO:4) was used as a probe for colony hybridization to identify clones containing genes homologous to, for example, the PUFA-PKS genes in ORF 7 and ORF 8 of *Shewanella*. A list of the various probes used for screening the *T. aureum* BAC library is indicated in Table 2.

TABLE 2

Probes Used for Screening the *T. aureum* Genomic BAC Library by Colony Hybridization

| Probe Name | Probe Length | Location on the *Schizochytrium* gene cluster |
|---|---|---|
| TA-PKS-1-1 | 1560 bp | ORF A |
| Contig 1763 | 602 bp | ORF B |

Example III

Identification of PUFA-PKS-Related Sequences from *Thraustochytrium aureum*

For screening of the *T. aureum* BAC library with the various probes described above, the library was plated on selective media as described in Example II, and white colonies were replica plated onto Hybond-N+ nylon membranes (Amersham Pharmacia, Piscataway, N.J.). The colonies were then lysed by incubation in 10% SDS for 5 min, denatured in [0.5N NaOH, 1.5M NaCl] buffer for 5 min, and neutralized in a solution containing [1.5M NaCl, 0.5M Tris.Cl (pH 7.4)] for 5 min. The membranes were then incubated in 2×SSC buffer with 0.1% SDS for 5 min, followed by treatment with 0.4 N NaOH for 20 min. Finally the filters were washed once in 2×SSC buffer for 20 min, followed by a wash in 5×SSC buffer for 5 min., and were finally dried at room temperature.

For hybridization, the membranes were prehybridized at 65° C. for 10 h in a buffer solution containing [1% BSA, 1 mM etylenediaminetetraacedic acid (EDTA)(pH 8.0), 0.5M NaHPO4 (pH 7.4), 7% SDS, and 10 ug/ml salmon sperm DNA]. Primary hybridization was carried out in 30 ml of the same buffer solution containing DNA probes that were labeled with $^{32}$p by random primer labeling using a kit (Stratagene, La Jolla, Calif.). Specific activity of the probes were >10$^9$ dpm/µg. Hybridization was carried out at 55° C. for 16–18 h, which was followed by two washes; the first wash was in a buffer containing [1×SSC+0.1% SDS] at 55° C. for 30 min; the second wash was carried out in a buffer containing [0.1×SSC+0.1% SDS] at 65° C. for 30 min. Membranes were then used to expose X-ray film at −80° C. overnight. Positive colonies that were detected by the first screening were subjected to a second round of screening using the same hybridization and washing conditions described above. Colonies selected from the secondary screen were subjected to a PCR screen using primers specific for the probes used, to confirm the presence of the probe sequence in the BAC clones identified.

The TA-PKS 1-1 probe, that contained sequence that was homologous to the ORF A region of the PKS gene cluster in *Schizochytrium* and ORF 5 of the PKS gene cluster in *Shewanella*, was used for screening the BAC library constructed in True-Blue BAC2 vector. This screening resulted in the identification of nine putative positive clones, all of which contained the TA-PKS1-1 probe sequence which was determined by PCR screening. Partial sequencing of three of these nine clones revealed the presence of gene sequences that were homologous to genes present in ORF A and ORF B of the *Schizochytrium* PUFA-PKS gene cluster, as well as homologous to genes present in the ORF 5, ORF 6 and ORF 7 of the *Shewanella* PUFA-PKS gene cluster. Sequences corresponding to those present in ORF C of the *Schizochytrium* PUFA-PKS cluster or homologous to genes in ORF 8 of *Shewanella* as well as the Dehydratase (DH) genes in ORF 7 of *Shewanella* were not detected in any of these BAC clones. One of these three BAC clones (BAC #164) was selected for full-length sequencing, to determine the entire sequence of the putative PKS gene cluster and also corresponds to sequences present in ORF 5, ORF 6, ORF 7 and ORF 8 of the *Shewanella* PUFA-PKS domains. The full-length sequence of ~50 kb BAC #164 revealed the presence of genes that were organized in the same sequential order as those present in ORF A and ORF B of the *Schizochytrium* PKS gene clusters. The biologically active domains of the *Thraustochytrium aureum* PKS gene cluster are depicted in FIG. 3. Details of the domains contained in each ORF are described below.

*Thraustochytrium aureum* ORFs Present on BAC #164

SEQ ID NO:8 ORF A 38,716 to 47,463 8748 bases Frame1 (forward)

SEQ ID NO:9 ORF B 31,128 to 37,250* 6123 bases Frame2(reverse)

* reverse sequence extending from position 37,250 to 31,128 is shown in SEQ ID NO:9

Open Reading Frame A (ORF A)

The complete nucleotide sequence of ORF A is 8748 bp including the stop codon (SEQ ID NO:8), and encodes a protein of 2915 amino acids (SEQ ID NO:10). Within ORF A, eleven domains were identified which include:

a. a β-keto-acyl-ACP synthase (KS) domain
b. a malonyl-CoA:ACP acyltransferase (MAT) domain
c. eight acyl carrier protein (ACP) domains
d. a ketoreductase (KR) domain The sequences of individual domains provided herein are thought to contain the full-length of the sequence encoding the functional domain, in addition to some flanking regions within the ORF. These domains were identified based on homology comparison with bacterial PUFA-PKS (Metz et al., (2001) *Science* 293:290–293) systems as well as the *Schizochytrium* PUFA-PKS system (Yazawa, K., (1996) 31 Suppl:S297–300). This was done using 'TfastA' (GCG Wisconsin Package, Madison, Wis.), which uses a method of Pearson and Lipman (Pearson et al., *Proc. Natl. Acad. Sci. USA* (1988) 85:2444–48) to search for similarities between a query peptide sequence and a group of nucleotide sequences translated in all six reading frames. The sequences obtained from *Thraustochytrium aureum* were searched against the GenBank public domain database. In addition, other programs used for analysis include 'BestFit' (GCG Wisconsin Package) which inserts gaps to obtain the optimal alignment of the best region of similarity between two sequences, and 'Gap' (GCG Wisconsin Package) which uses the algorithm of Needleman and Wunsch (*J. Mol. Biol.* (1970) 48:443–53) to align two sequences so as to maximize the number of matches and minimize the number of gaps. In addition, a program Pfam (Bateman et al., (2002) *Nucleic Acids Res.* 30:276–280) was used for analysis. This program can compare proteins or regions of proteins to existing protein domains or conserved protein regions, thus grouping proteins into families based on predicted function.

The domains within ORF A are represented in Table 3.

TABLE 3

Protein Domains Present in ORF A of the PUFA-PKS genes from *Thraustochytrium aureum*

| ORF A Domains | Position on Nucleotide Sequence@ SEQ ID NO: 8 | Position on Protein Sequence@ SEQ ID NO: 10 | Conserved Motif/Family |
|---|---|---|---|
| KS | 289–1764 (SEQ ID NO: 12) | 97–588 (SEQ ID NO: 13) | DXAC* (*acyl binding site $C_{302}$) |
| MAT | 1975–3305 (SEQ ID NO: 14) | 659–1101 (SEQ ID NO: 15) | GHS*XG (*acyl binding site $S_{787}$) |
| ACP | 3511–3777 (SEQ ID NO: 16)& 3880–4137 4243–4500 4576–4833 4936–5193 5269–5526 5629–5886 5989–6243 | 1172–1259 (SEQ ID NO: 17) 1295–1380 1415–1501 1527–1611 1648–1732 1758–1843 1878–1962 1997–2082 | LGIDS* (*pantetheine binding site S) |
| KR | 6280–8745 (SEQ ID NO: 18) | 2094–2916 (SEQ ID NO: 19) | short chain dehydrogenase family |

@The actual start and end positions of the domain may be internal to the sequence listed.
&The nucleotide and amino acid sequence of the ACP proteins are highly conserved and hence the domain of only one sequence is represented in the sequence identifier.

Open Reading Frame B (ORF B)

The complete nucleic acid sequence of ORF B is 6123 bp (SEQ ID NO:9) including the stop codon, and encodes a protein of 2040 amino acids (SEQ ID NO:11). Within ORF B, four domains were identified which include:

a. β-keto-acyl-ACP synthase (KS) domain
b. a chain length factor (CLF) domain
c. an acyl transferase (AT) domain
d. an enoyl-ACP-reductase (ER) domain The domains in ORF B were determined based on homology with the prokaryotic and eukaryotic PUFA-PKS systems as described for ORF A. The sequences of individual domains provided herein are thought to contain the full-length sequence encoding the functional domain, in addition to some flanking regions within the ORF. The domains within ORF B are represented in Table 4.

TABLE 4

Protein Domains Present in ORF B of the PUFA-PKS Genes From *Thraustochytrium aureum*

| ORF B Domains | Position on Nucleotide Sequence@ SEQ ID 9 | Position on Protein Sequence@ SEQ ID 11 | Conserved Motif/Family |
|---|---|---|---|
| KS | 79–1461 (SEQ ID NO: 20) | 27–487 (SEQ ID NO: 21) | DXAC* (*acyl-binding site $C_{237}$) |
| CLF | 1480–2814 (SEQ ID NO: 22) | 494–938 (SEQ ID NO: 23) | KS active site motif without acyl-binding cysteine |
| AT | 2815–4302 (SEQ ID NO: 24) | 939–1434 (SEQ ID NO: 25) | GXS*XG (* acyl-binding site $S_{1167}$) |

TABLE 4-continued

Protein Domains Present in ORF B of the PUFA-PKS Genes From *Thraustochytrium aureum*

| ORF B Domains | Position on Nucleotide Sequence@ SEQ ID 9 | Position on Protein Sequence@ SEQ ID 11 | Conserved Motif/Family |
|---|---|---|---|
| ER | 4441–6123 (SEQ ID NO: 26) | 1481–2041 (SEQ ID NO: 27) | |

@The actual start and end positions of the domain may be internal to the sequence listed.

The overall amino acid sequence comparison of the two ORFs containing the PUFA-PKS genes from *Thraustochytrium aureum* with that of the published *Schizochytrium* PUFA-PKS genes is displayed in Table 5. This sequence comparison was carried out using the 'Gap' program in the GCG Wisconsin package, except where indicated.

TABLE 5

Comparison of the PUFA-PKS Gene Clusters from *Thraustochytrium aureum* with that from *Schizochytrium* and *Shewanella*

| PKS-ORFs Identified from *T. aureum* | Length of ORFs from *T. aureum* | % Amino Acid Sequence Identity with *Schizochytrium* PKS-ORFs | % Amino Acid Sequence Identity With *Shewanella* PUFA-PKS-ORFs |
|---|---|---|---|
| ORF A | 8748 bp | 61.1% identity with ORF A | 38.4% identity with ORF 5: *KAS domain-49.2% identity *MAT domain-40% identity *ACP domain-~40% identity *KS domain-45% identity |
| ORF B | 6123 bp | 59.4% identity with ORF B | 21.9% identity with ORF 6: *AT domain-25.8% identity 26% identity with ORF 7: *KS domain-38.3% identity *CLF domain-36.8% identity 48.4% identity with ORF 8: *ER domain-55.2% identity |

*Alignments carried out using the "Bestfit" program of GCG.

The functionality of the *Shewanella* PKS gene cluster in generation of long chain PUFAs such as EPA has been well-established (see U.S. Pat. No. 5,683,898; Yazawa, *Lipids* (1996) 31 Suppl:S297–300; Metz et al., *Science* (2001) 293:290–293). In addition, sequences from other organisms such as *Vibrio marinus*, which share sequence homology or identity with the *Shewanella* PUFA-PKS genes, have also been shown to be involved in long chain PUFA production (see U.S. Pat. No. 6,140,486; Tanaka et al., *Biotechnol. Lett.* (1999) 21:939). The high sequence homology or identity between the *Thraustochytrium aureum* PKS genes identified herein and the active domains of the *Shewanella* PUFA-PKS gene cluster (see Table 5) indicates that the isolated sequences identified herein have similar functional utility as that of the *Shewanella* and *Vibrio* PKS genes in the production of EPA and DHA.

Example IV

Production of PUFAs in Transgenic Plants

The two ORFs from *Thraustochytrium aureum* may be cloned into suitable plant expression cassettes to be used for plant transformation. Since ORF A and ORF B are within the vicinity of each other, they may be cloned into a single expression cassette in one plant or into two separate expression cassettes in separate plants. If separate plants are used, a heterozygous seed may be produced by crossing the two transgenic plants. Standard transformation protocols may be used which include *Agrobacterium* transformation, or particle bombardment transformation protocols. Transformants may be identified by growing plants on selective media, and transformation of the full-length constructs may be verified by Southern Blot analysis. Immature seeds may also be tested for protein expression of the enzymes encoded by the two ORFs by immunoblotting. The best expressing plants may then be selected and further propagated for further experimentation. The seeds may also be analyzed for (EPA/DHA) PUFA production, and the best producers grown out and developed through conventional breeding techniques.

SEQUENCE LISTING

```
<160> NUMBER OF SEQ ID NOS: 27

<210> SEQ ID NO 1
<211> LENGTH: 23
<212> TYPE: DNA
<213> ORGANISM: Artificial Sequence
<220> FEATURE:
<223> OTHER INFORMATION: M13 Forward Primer

<400> SEQUENCE: 1
agcggataac aatttcacac agg                                              23
```

<210> SEQ ID NO 2
<211> LENGTH: 713
<212> TYPE: DNA
<213> ORGANISM: T. aureum

<400> SEQUENCE: 2

| | | | | | |
|---|---|---|---|---|---|
| cacgaggcca | agcattcgag | caaagcgctc | aaccagcaga | tcccaggcgg | gcgcgcctgc | 60 |
| ttcgtgggcg | tctcgcgaat | cgacggacag | ctcggactta | gcggagcttg | cgcgaaagga | 120 |
| aagggctggg | ctgaggccgc | agagattgct | cagcaaggag | ccgtcgcagg | cttgtgcaag | 180 |
| accttggacc | tagagtggcc | gcacgtcttc | gctcgcagca | tcgacatcga | gcttggcgcg | 240 |
| aacgaagaaa | cagctgcgca | agcaatcttt | gaggagctct | cttgcccgga | cctaacggtg | 300 |
| cgcgaagcag | gatacaccaa | agacggcaag | cggtggacga | ctgaggcgcg | accggttggg | 360 |
| cttggcaagc | ccaagcaggc | actacgttct | tcggacgtct | tcttggtttc | tggtggggcg | 420 |
| cggggaatta | cacctgtttg | cgttcgcgag | ttggccaaat | cgatcagtgg | tggcactttt | 480 |
| gtcctcctcg | gcggtccccc | tctcgctgat | gatccggcgt | gggcttgcgg | cgtcgaggaa | 540 |
| gcaaacattg | gacagccgc | tatggcgcac | ctcaaggccg | agttcgcagc | cgggcgcggc | 600 |
| ccgaagccga | cgccaaaggc | ccacaaagca | ctcgttggga | gcgtcctggg | ggcgcgcgaa | 660 |
| gtccttggtt | cgctagagag | tattcgcgcc | cagggtgcgc | gcgccgagta | cgt | 713 |

<210> SEQ ID NO 3
<211> LENGTH: 1023
<212> TYPE: DNA
<213> ORGANISM: T. aureum

<400> SEQUENCE: 3

| | | | | | |
|---|---|---|---|---|---|
| tcgccaacac | aagttctggt | tggcaactgg | ggcttgcccc | ctgtagttcc | taacgcgagc | 60 |
| gtgcacaaga | ttactgtgag | gcttggcggg | gagtctgcaa | acccttttcct | gtcctcccac | 120 |
| acgattcaag | gcagaaaggt | cttgccgatg | actgyggcgc | ttgggcttct | cgctgaggcg | 180 |
| gctcgagggc | tctacgtcgg | tcaccaagta | gycgggattg | aggacgccca | agtcttccag | 240 |
| ggagtcgtgt | tggacaaagg | ggcgacgtgt | gaggtccagc | ttcgccgcga | gtcttcgact | 300 |
| gcaagcccaa | gcgaggttgt | gctgagtgct | tcgctcaatg | tattcgcggc | gggaaaggtt | 360 |
| gtgcctgcgt | accgcgcgca | tgtcgtgctc | ggcgcttcag | ggccacgcac | tggcggcgtg | 420 |
| cagcttgaac | tgaaagattt | gggcgtggac | gccgaccctg | cttgctccgt | tggcaagggt | 480 |
| gcgctgtacg | acggtaggac | gctgttccat | gggccggcgt | ttcagtacat | ggatgaggtt | 540 |
| ccctggtgct | cgcctgcaga | gcttgccgtg | cggtgccgtg | tcgttccgag | cgcggctcag | 600 |
| gaccgcggcc | aatatgtttc | gcgcggagtg | ttgtacgacc | cgttcctgaa | cgacacggtg | 660 |
| tttcaagctc | tccttgtttg | ggcccgtctg | gtcaggaca | gcgcttcgct | accgagcaac | 720 |
| gttgaacgaa | tctcgttcca | cggccagccg | ccgagcgagg | gcgaggtgta | gtacaccacg | 780 |
| ctcaagctgg | acagtgctgc | gagcgggccg | ctcgacccga | ttgcaacagg | cgcatttctt | 840 |
| cctccaccga | gcttgcgggg | cggtctttgc | atcagggcga | gcgagtgtgg | ttctgaacaa | 900 |
| ggctctttcg | tatgatggct | ctcgacccaa | aggcgagtag | agtactctac | tcagtactcc | 960 |
| ttttcacata | ccggcaggca | gcgttgctgt | gggatggccg | ggggctcttc | tgcacgcggc | 1020 |
| tcc | | | | | | 1023 |

<210> SEQ ID NO 4
<211> LENGTH: 1240

```
<212> TYPE: DNA
<213> ORGANISM: T. aureum
<220> FEATURE:
<221> NAME/KEY: misc_feature
<222> LOCATION: (208)...(208)
<223> OTHER INFORMATION: n=a,t,c, or g

<400> SEQUENCE: 4
gaattcggca cgaggccggc ctcacgacgc aggttgttcg gttccgcgct gcaggtctgt      60
cacgcaacgc ggacggctct gttcgagtcc gcaaccgcat catcggaaag atttcgcgca     120
cggagctcgc ggagatgttc attcgccccg ctccggaggc cctcttgacc aagttggttg     180
cgtcgggtga gatttcggcc gagcagmngc ctggccaaac aagtgccgat gccgacgaca     240
ttgccgtcga gsagaactcg ggcggccaca cggacaatcg cccgatccat gtcatccttc     300
cgctgatcat cgcgctccgc aacaggctgc acaaggagtg cggttacccg gcgagccttc     360
gcgttcgagt tggcgcgggt ggcgggatcg gctgcccgct tgcagcaact gcggccttca     420
acatgggcgc cgccttttctc gtgacaggaa cagtcaacca actcagccgg cagtcgggca     480
cctgcgacgc ggtgcgcats agcttttcaa aagcgaccta ctcggacatc acaatggcgc     540
ccgccgcaga tatgtttgac caggggggttg agctccaggt gctcaagaag ggcaccatgt     600
ttccgtcgcg cgccaagaag ctctacgagc tgttttgcac gtacaactcg ktcgacgaga     660
tgcccgccga ggagctcgcg cgggttgaga agcsgatytt ccaaaagccc ctcgcggscg     720
tatgggacga gacgaaagac ttttacatca accgtctcca caacgaggac aagatcgaac     780
gcgcagaaaa ggatggcaag ctcaagatgt cgctctcgtt ccgctggtac cttggcctga     840
gttcgttctg ggccaacaat ggaatcgccg accgcgtgct ggactatcaa gtgtggtgcg     900
gccctgcgat tggggcctgg aacgactttg ccaagggatc ctacctcgac gccgaggtct     960
gcggccagtt tccttgcgtt gtgcaggtca acctgcagat cctccacgcg cggcctacat    1020
gcagcgcctt ctggccgtca agcatgaccc gcgcatcgag tttgacctcg aggacccggt    1080
ctttggtacg cccccactgc cgcgctctaa agcgatgcag caacgcactc tttcggaggc    1140
ccgtcgctgc agcacttgtg cgaactcgat agggtttctt tcaagatttc aatcaacaaa    1200
acaagtattg gaatgacaaa aaaaaaaaaa aaaactcgag                          1240

<210> SEQ ID NO 5
<211> LENGTH: 24
<212> TYPE: DNA
<213> ORGANISM: Artificial Sequence
<220> FEATURE:
<223> OTHER INFORMATION: RO 1447 Forward Primer

<400> SEQUENCE: 5
cttgtgcaag accttggacc taga                                             24

<210> SEQ ID NO 6
<211> LENGTH: 24
<212> TYPE: DNA
<213> ORGANISM: Artificial Sequence
<220> FEATURE:
<223> OTHER INFORMATION: RO 1448 Reverse Primer

<400> SEQUENCE: 6
gaacctcatc catgtactga aacg                                             24

<210> SEQ ID NO 7
<211> LENGTH: 1561
<212> TYPE: DNA
<213> ORGANISM: T. aureum
```

<400> SEQUENCE: 7

```
ttgtgcaaga ccttggacct agagtggccg cacgtcttcg ctcgcagcat cgacatcgag    60
cttggcgcga acgaagaaac agctgcgcaa gcaatctttg aggagctctc ttgcccggac   120
ctaacggtgc gcgaagcagg atacaccaaa gacggcaagc ggtggacgac tgaggcgcga   180
ccggttgggc ttggcaagcc caagcaggca ctacgttctt cggacgtctt cttggttcct   240
ggtggggcgc ggggaattac acctgtttgc gttcgcgagt tggccaaatc gatcagtggt   300
ggcacttttg tcctcctcgg gcggtcccct ctcgctgatg atccggcgtg gcttgcggc    360
gtcgaggaag caaacattgg acagccgct atggcgcacc tcaaggccga gttcgcagcc    420
gggcgcggcc cgaagccgac gccaaaggcc cacaaagcac tcgttgggag cgtcctgggg   480
gcgcgcgaag tccttggttc gctagagagt attcgcgccc agggtgcgcg cgccgagtac   540
gtttcctgcg acgtttcgtg tgcggagcgc gtcaaggccg tcgtcgacga tctcgagcga   600
cgggtcgggg ctgtaactgg ggttgtgcac gcctctggtg ttctccgaga caagtccgtt   660
gagcgcttgg agctcgccga cttcgaggtc gtgtacggca ccaaggtgga cggcctgctc   720
aacctgctgc aggccgtgga ccgccccaaa ctccggcact tggtcctctt cagctccctg   780
gccggtttcc acggcaacac tgggcaggcc gtgtacgcta tggcgaatga ggcgctgaac   840
aagatggcct tccatttgga aactgcgatg cctggcctct cggtcaagac gatcgggttt   900
ggaccttggg acggcggcat ggtcaacgat gcgctgaaag cgcactttgc gtctatgggc   960
gtccaaatta ttccgctcga cggygcgcg gagaccgttt cccgaatcat cggggcgtgc  1020
tcgccaacac aagttctggt tgcaactggg gcttgcccc ctgtagttcc taacgcgagc  1080
gtgcacaaga ttactgtgag gcttggcggg gagtctgcaa accctttcct gtcctcccac  1140
acgattcaag gcagaaaggt cttgccgatg actgyggcgc ttgggcttct cgctgaggcg  1200
gctcgagggc tctacgtcgg tcaccaagta gycgggattg aggacgccca agtcttccag  1260
ggagtcgtgt tggacaaagg ggcgacgtgt gaggtccagc ttcgccgcga gtcttcgact  1320
gcaagcccaa gcgaggttgt gctgagtgct tcgctcaatg tattcgcggc gggaaaggtt  1380
gtgcctgcgt accgcgcgca tgtcgtgctc ggcgcttcag ggccacgcac tggcggcgtg  1440
cagcttgaac tgaaagattt gggcgtggac gccgaccctg cttgctccgt tggcaagggt  1500
gcgctgtacg acggtaggac gctgttccat gggccggcgt ttcagtacat ggatgaggtt  1560
c                                                                 1561
```

<210> SEQ ID NO 8
<211> LENGTH: 8748
<212> TYPE: DNA
<213> ORGANISM: T. aureum

<400> SEQUENCE: 8

```
cgcaagtgca tccggccatc attgggccat cattgggcca tcattggtgt tttgggccgc    60
gctttgcgga tcgtccggcc gatcaggtac gaggccacga acctacgtcg tttgccgcgc   120
tcaggctggt tggttgcact tggactcttc tgtgaccttt catcgtgtgc aggcaaactc   180
gatttgcaga cccgagacac ggcgaaggat ccgtgctgca aacgcaagtg gagtgcgtcg   240
agagcaccgc cgagaccaag agccgaggca gacaaggcca gcaacgagat ggagacaaag   300
gacgatcgcg ttgcgatcgt gggcatgtcg gccatactgc cttgcggtga gtcagtgcgc   360
gagtcgtggg aggcgattcg cgagggggctc gattgcctgc aggacctgcc tgcggaccga   420
gtcgatatca cggcgtacta cgacccgaac aagacaacca aggacaagat ctactgcaag   480
```

```
cgcggcggct tcattcccga gtatgacttt gacgcgcgcg agttcggcct caacatgttc    540
cagatggagg actcggacgc caaccaaacc gtgactttgc tcaaggtcaa ggaggctctc    600
gaggacgccg gggtggagcc cttcacaaag aagaagaaga acattggctg cgtgctcggc    660
atcggcggcg ggcagaaggc gagccacgag ttttactccc gactcaacta tgtggtcgtg    720
gagaaggtgc ttcgcaagat gaacctcccc gacgaggttg tcgaggccgc cgtcgaaaag    780
tacaaggcca actttcctga atggcgcctc gactcgttcc ctgggttttct tggcaacgtg   840 accgccgggc ggtgcagcaa cgtcttcaac atggaaggca tgaactgcgt cgtggacgct    900
gcgtgcgcca gctcgctcat cgcgatcaag gttgccattg atgagctcct ccacggggac    960
tgcgacacca tgattgccgg tgcgacctgc accgacaact cgatcgggat gtacatggcc   1020
ttttccaaaa ccccagtttt ctccaccgac cagagcgtca aggcgtacga cgccaagacg   1080
aaaggcatgc tcatcggcga aggctcggcc atggtcgtgc tcaagcggta cgcggacgcc   1140
gttcgggatg gtgatgagat ccatgccgtc atcagggcat gcgcctcgtc cagcgacggc   1200
aaggctgctg gcatttacgc accgacggtg tcgggtcaag aagaggcact gcggcgcgcg   1260
tacgcccgag ctggcgtgga cccctccacc gtcacgctgg tggagggcca cggcactggc   1320
acacccgtcg gggaccggat tgagctgacc gccttgcgca acgtctttga cgcagccaac   1380
aaaggccgca aggaaacagt cgcggtggga agcatcaagt cgcagatcgg tcacctgaag   1440
gccgtggccg gctttgccgg tctcgtcaag gttgtcatgg ccctcaagca caagacgctg   1500
ccgcagacca tcaacgttca cgacccgccc gcactgcacg acggctcgcc catccaggat   1560
tcgagtcttt acatcaacac gatgaaccgg ccctggttta cggcacctgg cgtcccccgc   1620
cgtgcaggca tctctagctt tgggtttggc ggcgccaact accacgctgt tctcgaagag   1680
gccgagcctg agcacgcgaa gccgtatcgc atgaaccaag ttccacaacc ggtgctcttg   1740
cacgcaagct ccgcgtcagc tcttgcctcc atctgcgacg tcaggccgga cgcgctccag   1800
gccgccgtct cgcccgaagc cagcaagcac gcagactacc gcgccatcgt agcgttccat   1860
gaagcgttta gcttcgcgc tggagtgccg gccggccatg ctcgaattgg ctttgtgtcc   1920
ggcagcgcgg cagcaacgct tgcagtgctc cgagccgcct ctgcaaaact caagcagtcg   1980
agtgcgacgc tcgaatggac cctgctccgc gagggcgtca cgtaccgctc cgccgcgatg   2040
cacactcctg gcagtgtcgc tgctctgttt gccgggcaag gcgcgcagta cacgcacatg   2100
ttcgctgacg ttgccatgaa ctggccaccg tttcgaagcg ccgtgcaaga gatggatgcc   2160
gctcaagtca cggcggcagc gccgaagcgc ctcagcgagg tcctgtatcc gcgcaagccg   2220
tacgctgcag agcccgagca agacaacaag gccatctcga tgacgattaa ctcgcaaccg   2280
gccctcatgg cctgcgctgc tggggcgttt gaggtgtttc gtcaagctgg tcttgcgccc   2340
gaccacgtcg cgggtcattc tctcggcgag tttggtgctt tgctcgccgc tggatgcgca   2400
agccgtgagg agctcttccg tctggtctgc agcagagcga aggcaatgca agacgttccc   2460
aagccaagcg agggcgtcat ggcagctgtc atcggccgtg gtgctgacaa gctcacgctg   2520
caaggcgatg gtgcgtggct tgccaactgc aactcgccaa gccaagtggt catttccggc   2580
gacaagactg ctgtcgagcg tgaatccagc cggttggcag gccttggctt caggatcatt   2640
ccgcttgcat gcgaaggcgc cttccattca ccgcacatga cggcggccca ggccacgttt   2700
caggctgcac tggacagcct caagatctcc accccgacga acggggcgcg cctgtacaac   2760
aacgtttccg gaaagacctg ccgatccctg ggtgaactcc gcgactgcct gggcaagcac   2820
atgacaagtc ctgtgctctt ccaggcacag gtagagaaca tgtacgctgc cggggcgcgc   2880
```

```
attttcgtgg agtttggccc gaagcaagtc ctctccaagc tcgtaggcga gattctcgcc    2940
gacaagtcag actttgtgac agtcgcggtc aactcgtcat cgtccaagga cagcgacgtg    3000
caacttcgtg aagctgctgc gaagctcgcg gtccttggcg tcccgttggc gaactttgac    3060
ccttgggagc tctgcgacgc gcggcgtctt cgcgaatgcc cgcgatccaa gacgacgttg    3120
cgcttgtctg cagcgaccta cgtgtcgaac aagacccttg ctgctaggga aaggtcatg    3180 gaggacaact gcgactttc ttcgctcttt gcctccggtc cagcaagcca agagatggag    3240
cgagaaatag ccaaccttcg cgctgagctg gaggcggccc aacgccagct tgacacggcc    3300
aaaacccagc ttgctcgaaa gcaagtgcag gaccccaccg ctgaccgaca gcgcgatatg    3360
attgccaagc accgatccac actcgcagca atggtgaagg aattcgaggc tctggcaagt    3420
ggtagtcctt gcgctgttcc gtttgcgcct gtggtggaca ctgctgtcga agacgtgcct    3480
tttgcggaca aggtctcgac gccaccgccc aagtcactt ccgctcccat cgccgagctc    3540
gcgcgcgccg aggccgtcgt catggaggtt ctcgctgcca agactggcta cgaggtcgac    3600
atgatcgagg ccgacatgct gctcgacgcc gagctcggca tcgactcggt caagcgcatt    3660
gagatcctgg cagctgtcca ggcccagctc ggggtcgagg ccaaggacgt cgacgcgctc    3720
agccgcacac gaacagttgg cgaggtcgtt gacgccatga aggctgagat cggcgggcaa    3780
gcgaccagtg cgccttcgcc gatggcccag ccccaagcct cagcaccatc accgtcccct    3840
actgcctctg tgctgcctaa gctgttgct ttaccagcta gtgtcgatcc cgccaagctc    3900
gcgcgcgccg aagcggtcgt catggaggtt ctcgccgcca agactggcta cgaggtcgac    3960
atgatcgagg ctgacatgct gctcgacgcc gagctcggca tcgactcggt caagcgcatt    4020
gagatcctgg cggctgtcca agctcagctc ggggtcgagg ccaaggatgt cgacgcgctc    4080
agccgcacac gcactgttgg cgaggtcgtt gatgccatga aggctgagat cggcgggcaa    4140
gcgaccagcg cacctgcgtc cgtggcccag ccccaagcct cagcaccatc accgtccgca    4200
acaactgcct ctgtgctgcc taagcctgtt gctgcaccaa ctagcgccga tcccgccaag    4260
ctcgcgcgcg ccgaagccgt cgtcatggag gttctcgctg ccaagactgg ctacgaggtc    4320
gacatgatcg aggctgacat gctgctcgac gccgagctcg gcatcgactc ggtcaagcgc    4380
attgagatcc tggcggctgt ccaagcccag ctcggggtcg aggccaagga cgtcgacgcg    4440
ctcagccgca cacgcacggt tggcgaggtc gtcgaggcca tgaaggctga gatcggcggg    4500
caagcgacca gtgcacctgc gtccgtggcc cagccccaaa tctctgtgtc ccctacgcct    4560
ctcgctgcat ctcctagtgc cgatcctgcc aagctcgcgc gcgccgaagc cgtcgtcatg    4620
gaggttctcg ctgccaagac tggctacgag gtcgacatga tcgaggctga catgctgctc    4680
gacgccgagc tcggcatcga ctccgtcaag cgcatcgaga tcctggcggc tgtccaggcc    4740
cagctcgggg tcgaggccaa ggacgtcgac gcgctcagcc gcacgcac tgttggcgag    4800 gtcgttgacg ccatgaaggc tgagatcggc gggcaagcga ccagtgcgcc tgcatccgtg    4860
gcccagcccc aagcctcagc accgtcgccg tccgctactg cctctgtgct gcctaagcct    4920
gttgctgcac caactagcgc cgatcccgcc aagctcgcgc gcgccgaagc cgtcgtcatg    4980
gaggttctcg ctgccaagac tggctacgag gtcgacatga tcgaggctga catgctgctc    5040
gacgccgagc tcggcatcga ctcggtcaag cgcatcgaga tcctggcggc tgtccaagcc    5100
cagctcgggg tcgaggccaa ggacgtcgac gcgctcagcc gcacacgcac ggttggcgag    5160
gtcgtcgagg ccatgaaggc tgagatcggc gggcaagcga ccagtgcacc tgcgtccatg    5220
gcccagcccc aaatctctgt gtcccctacg cctctcgctg catctcctag tgccgatcct    5280
```

```
gccaagctcg cgcgcgccga ggccgtcgtc atggaggttc tcgctgccaa gactggctac    5340
gaggtcgaca tgatcgaggc cgacatgctg ctcgacgccg agctcggcat cgactcggtc    5400
aagcgcatcg agatcctggc ggctgtccaa gctcagctcg gggtcgaggc caaggacgtc    5460
gacgcgctca gccgcacacg cacggttggc gaggtcgttg atgccatgaa ggctgagatc    5520
ggcgggcaag cgaccagtgc gcctgcatcc gtggcccagc cccaagcctc agcaccgtcg    5580
ccgtccgcta ctgcctctgc gcctgttacg cctctcgctg caccagctag tgtcgatccc    5640
gccaagctcg cgcgcgccga agccgtcgtc atggaggttc tcgccgccaa gactggctac    5700
gaggtcgaca tgatcgaggc tgacatgctg ctcgacgccg agctcggcat cgactccgtc    5760
aagcggattg agatcctggc ggctgtccaa gcccagctcg gggtcgaggc caaggacgtc    5820
gacgcgctca gccgcacacg cactgttggc gaggtcgttg acgccatgaa ggctgagatc    5880
ggcgggcaag cgaccagcgc acctgcgtcc gtggcccagc cccaagcctc agcaccgtcg    5940
ccgtccgcta ctgcctctgt gctgcctaag cctgttgctt caccagctag tgtcgatccc    6000
gccaagctcg cgcgcgccga agcggtcgtc atggaggttc tcgctgccaa gactggctac    6060
gaggtcgaca tgatcgacgc tgacatgctg ctcgacgccg agctcggcat cgactccgtc    6120
aagcgcatcg agatcctggc ggctgtccaa gcccagctcg gggtcgaggc caaggacgtc    6180
gacgcgctca gccgcacacg aacggttggc gaggtcgtcg aggccatgaa ggctgagatc    6240
ggggcagcag gtccaaacga tgcacaagca gcgtctgggc atctctttgg cacgggatgt    6300
gaagacctga gcctttgctc tgcttctgtg gttgagattg ctcgttgcag cgaactagct    6360
ctggagcgcc cgatggatcg gcccattctt attgtaagcg atggatcagc attgccggcg    6420
gctctggcta gtcgactggg gtcgtgtgca gtaatcctca cgaccgcagg cgagaccgac    6480
caatctgtgc gctcgacgaa gcacgttgac atggaagggt ggggcgaggc agatctcgtg    6540
cgcgctcttg aagcagtaga gtctcgattc ggcgtcccag gcggcgtcgt ggtgcttgag    6600
cgcgcctcag aaacagctag ggaccagctt ggctttgccc tgctgcttgc caagcattcg    6660
agcaaagcgc tcaaccagca gatcccaggc gggcgcgcct gcttcgtggg cgtctcgcga    6720
atcgacggaa agctcggact agcggagct tgcgcgaaag gaaagggctg gctgaggcc    6780 gcagagattg ctcagcaagg agccgtcgcg ggcttgtgca agaccttgga cctagagtgg    6840
ccgcacgtct tcgctcgcag catcgacatc gagcttggcg cgaacgaaga aacagctgcg    6900
caagcaatct ttgaggagct ctcttgcccg gacctaacgg tgcgcgaagc aggatacacc    6960
aaagacggca agcggtggac gactgaggcg cgaccggttg ggcttggcaa gcccaagcag    7020
gcactacgtt cttcggacgt cttcttggtt tctggtgggg cgcggggaat tacacctgtt    7080
tgcgttcgcg agttggccaa atcgatcagt ggtggcactt ttgtcctcct cgggcggtcc    7140
cctctcgctg atgatccggc gtgggcttgc ggcgtcgagg aagcaaacat tgggacagcc    7200
gctatggcgc acctcaaggc cgagttcgca gccgggcgcg gcccgaagcc gacgccaaag    7260
gcccacaaag cactcgttgg gagcgtcctg ggggcgcgcg aagtccttgg ttcgctagag    7320
agtattcgcg cccagggtgc gcgcgccgag tacgtttcct cgacgtttc gtgtgcggag    7380 cgcgtcaagg ccgtcgtcga cgatctcgag cgacgggtcg gggctgtaac tggggttgtg    7440
cacgcctctg gtgttctccg agacaagtcc gttgagcgct tggagctcgc cgacttcgag    7500
gtcgtgtacg gcaccaaggt ggacggcctg ctcaacctgc tgcaggccgt ggaccgcccc    7560
aaactccggc acttggtcct cttcagctcc ctggccggtt ccacggcaa cactgggcag    7620 gccgtgtacg ctatggcgaa tgaggcgctg aacaagatgg ccttccattt ggaaactgcg    7680
```

-continued

```
atgcctggcc tctcggtcaa gacgatcggg tttggacctt gggacggcgg catggtcaac    7740
gatgcgctga aagcgcactt tgcgtctatg ggcgtccaaa ttattccgct cgacggcggc    7800
gcggagaccg tttcccgaat catcggggcg tgctcgccaa cacaagttct ggttggcaac    7860
tggggcttgc ccctgtagt tcctaacgcg agcgtgcaca agattactgt gaggcttggc    7920
ggggagtctg caaacccttt cctgtcctcg cacacgattc aaggcagaaa ggtcttgccg    7980
atgactgtgg cgcttgggct tctcgctgag gcggctcgag ggctctacgt cggtcaccaa    8040
gtagtcggga ttgaggacgc ccaagtcttc cagggagtcg tgttggacaa aggggcgacg    8100
tgtgaggtcc agcttcgccg cgagtcttcg actgcaagcc caagcgaggt tgtgctgagt    8160
gcttcgctca atgtattcgc ggcgggaaag gttgtgcctg cgtaccgcgc gcatgtcgtg    8220
ctcggcgctt cagggccacg cactggcggc gtgcagcttg aactgaaaga tttgggcgtg    8280
gacgccgacc ctgcttgctc cgttggcaag ggtgcgctgt acgacggtag gacgctgttc    8340
catgggccgg cgtttcagta catggatgag gttcttcggt gctcgcctgc agagcttgcc    8400
gtgcggtgcc gtgtcgttcc gagcgcggct caggaccgcg gccaatttgt ttcgcgcgga    8460
gtgttgtacg acccgttcct gaacgacacg gtgtttcaag ctctccttgt ttgggcccgt    8520
ctggtcaggg acagcgcttc gctaccgagc aacgttgaac gaatctcgtt ccacggccag    8580
ccgccgagcg agggcgaggt gttttacacc acgctcaagc tggacagtgc tgcgagcggg    8640
ccgctcgacc cgattgcaaa ggcgcagttc ttcctccacc gagcttgcgg ggcggtcttt    8700
gcatcagggc gagcgagtgt ggttctgaac aaggctcttt cgttttga                8748
```

<210> SEQ ID NO 9
<211> LENGTH: 6123
<212> TYPE: DNA
<213> ORGANISM: T. aureum

<400> SEQUENCE: 9

```
caagcaatcg gccatcgagc tgcgcgttgg agctgccgat cgaaatcgaa agcaagaggc      60
cacaaggctc agaaagagat gaaccagggc gggagaaatg acgagggcgt ctcggtggcg     120
cgcgcggacc catgccctga cacgcggatc gctgtcgtgg gcatggcggt cgagtatgca     180
gggtgccgcg gcaaggaagc gttctgggac acgctcatga acggcaaaat caactctgcc     240
tgtatctcag acgatcgcct cggtcagca cgacgagaag agcactatgc gcccgagagg     300
tcaaagtacg ccgatacgtt ctgcaacgag aggtacggat gcatcgatcc caaagtcgac     360
aacgagcacg acctgctcct cggcctcgcc gcggctgcgc ttcaagacgc gcaggacagg     420
cgcagcgacg gcggcaagtt cgacccagcg cagctcaagc gctgcggcat tgtcagcggc     480
tgcctgtcct tcccgatgga caacctgcaa ggcgagctgc tcaacccttta ccaagcccat     540 gctgagaggc ggattggcaa gcattgcttc gcggaccaaa cgccctggtc gacgcgaacc     600
agagcgcttc acccgctgcc cggggacccg aggacccacc gcgacccagc ctccttcgtc     660
gccggacagc tcggcctcgg cccgctgcac tactcgctcg acgccgcctg cgcctcggcc     720
ctttacgttc tgcgactcgc tcaggaccac ctcctctcgg gcgaggctga cttgatgctg     780
tgcggagcga cgtgcttccc agagcccttc ttcatcctga ctgggtttag cacgttccac     840
gcgatgccag tcggtgagaa cggtgtctcg atgccgtttc atcgggacac gcaagggctg     900
acgcccggcg agggcggctc ggtgatggtg ctcaagcgcc tcgcggacgc cgagcgcgac     960
ggagaccaca tctacgggac gcttcttgga gccagcttga gcaacgcagg ctgcgggctt    1020
cctctcaagc cgcaccagcc aagcgaggag gcctgcttga aagccaccta cgagctcgtc    1080
```

```
ggcgtgccgc cccgagacgt ccagtacgtc gagtgccacg ccaccggcac gccgcagggc   1140
gacaccgtcg agctccaagc cgtcaaagcc tgctttgagg gcgcaagccc ccggatcggg   1200
tccacgaaag gcaacttcgg acacaccctc gtcgcggccg gctttgcggg aatgtgcaag   1260
gttctccttg caatggagcg cggcgtgatc cccccgaccc cgggcgttga ctctggcacc   1320
cagattgatc ccctcgtcgt cacagcggcg ctcccgtggc cggatacgcg cggcgggccg   1380
aaacgcgcag gactctccgc attcggattc gggggcacaa acgcgcacgc cgtctttgag   1440
gagcatattc cctcgagagc tccgcccgca gtactctgcc agcctcgcct cggcagcgga   1500
ccaaaccgaa agcttgctat cgtcggcatg gatgccacgt ttggatcctt gaagggtctc   1560
tccgcactag aagctgcgct ttacgaggca aggcacgctg cgcggcccct gcctgcgaag   1620
cgctggcgct tcttgggcgg ggacgagtcc tttctccacg agatcggact cgagtgctct   1680
ccgcacgggt gctacattga ggacgtggat gtggacttta agcgactccg cacgccaatg   1740
gtgccggagg acttgctccg gccgcaacag ctcctggccg tgtcgacgat tgacaaggcc   1800
atcctcgact cgggcttggc caagggcggc aacgtggctg tccttgtcgg cctcgggacg   1860
gacctcgagc tctaccgcca ccgagctcgg gttgcgctta aggagcgtct tcaaggactg   1920
gttcgctctg ccgagggagg agccctgacg tctcgcctga tgaactatat caatgatagc   1980
ggaacgtcga cctcctacac gtcgtatatc ggcaacctcg tcgccacgcg cgtctcgtcc   2040
cagtggggct tcactgggcc gtcgttcacc gtcacggaag gggccaactc ggtccatcgg   2100 tgcgccagc tcgccaagta catgctcgac cgcggcgagg tcgacgccgt cgtggttgca   2160
ggagtcgacc tgtgcgggag cgccgaggcg ttcttcgtga ggtcgcgccg catgcagatc   2220
tcgaaaagtc agcgcccggc cgcgccgttt gaccgcgccg cagacggctt cttcgcgggg   2280
gaagggtgcg gcgccctcgt cttcaaacgc ctgactgact gtgtgtctgg cgagcgaatc   2340
tacgcgtccc tcgactcggt cgtcgtcgca accacgccgc gcgccgctct tcgtgctgcc   2400
gcagggtcgg cgcgggttga cccagccagc atcgacatgg tcgagctgag cgcagattcc   2460
caccggtttg tgcgggcgcc aggcaccgtg gctcagcctc tgacagccga agtcgaggtc   2520
ggggcggtgc gggaagtgat cgggaccgcg gggagggget ctcgaagcgt ggccgtcgga   2580
tcggtccgcg ccaacgtcgg ggacgcaggg tttgcttccg gggccgctgc cctcgtaaaa   2640
actgcgctct gcttgcacaa ccgctacttg gcggctaccc caggctggga tgcgcctgct   2700
gccggcgtgg attttggtgc cgagctgtac gtttgccgcg agtcgcgtgc ttgggtcaag   2760
aacgccggcg ttgcacggca cgccgcaatt tctggcgtgg acgaaggcgg gtcgtgctat   2820
gggctggttc tttcggacgt gcctgggcag tacgagaccg gcaaccgcat ctccctccag   2880
gccgagtcgc ccaagctctt gctcctctcg gctccagacc acgccgcctt gctggacaag   2940
gtggcggccg agctcgcagc ccttgagcaa gccgacggct tgagcgccgc cgcggctgcc   3000
gtagaccgct tactcggcga gtcgctcgtc ggttgcgcgc ctggcagcgg cgggctgacc   3060
ctttgcttgg tggcttcgcc tgccagcctc cacaaggagc ttgcgctggc ccatcgaggg   3120
atcccgcgct gcatcaaagc acggcgcgac tgggccagcc cggcagggag ctacttcgcc   3180
ccggagccga tcgcaagcga ccgcgtcgcg ttcatgtacg gggaaggacg aagcccgtac   3240
tgcggcgtcg gccgcgacct ccaccggatc tggcccgcgc tgcatgagcg ggtgaacgcc   3300
aagactgtca acctctgggg tgacggtgac gcctggctgc tgccacgtgc aacctcggcc   3360
gaggaagagg agcaactctg ccgcaacttc gactcgaacc aggttgagat gtttcgaacg   3420
ggcgtgtaca tctcgatgtg cttgaccgac ctcgctcgaa gcttgattgg actgggccct   3480
```

```
aaggcgagct tgggctcag cctaggcgag gtttccatgc tcttcgctct gagcgagtcc    3540
aactgtagac tgtcggagga aatgacccgc aggctccgtg cgtccccggt gtggaactcg    3600
gagctcgccg tcgagttcaa cgcccttcga aagttgtggg gggtcgcgcc gggggcaccc    3660
gtcgactcgt tctggcaagg ttatgtcgtg cgcgcaacgc gggctcaggt ggagcaagcc    3720
attggggagg acaatcagtt tgtgcgtctc ctgatcgtga acgactcgca atcagtcctg    3780
atcgccggca agccggcggc gtgcgaagcc gtaattgctc gcatcgggtc tattcttccc    3840
ccgctgcaag tgtcgcaagg catggtgggg cactgtgccg aggtcttgcc gtacacgagc    3900
gagatcgggc gcatccacaa catgcttcgc ttcccatcgc aggacgaaac gggcggttgc    3960
aaaatgtact ctagcgtctc aaactcgcgc atcgggccag tcgaggagag ccagatgggc    4020
ccaggcactg agctcgtttt ctcgccgtca atggaagact ttgtcgccca gctgtactcg    4080
cgagttgcag actttccggc gatcaccgag gcggtttacc agcagggtca tgacgtgttt    4140
gtcgaagtgg ggccggacca ttcacggtcg gctgctgtcc gctccacgct tggacccact    4200
cggcgacaca tcgctgtggc gatggaccgc aagggtgagt cagcttggtc gcagcttctg    4260
aaaatgctgg ctacgcttgc gtcgcaccgc gtgccgggcc tggaccttc atccatgtac    4320 caccccgcag tggtggagcg ttgcaggctg gcgctggcag cacaacgatc gggccagcca    4380
gagcagcgga acaagttttt gcgcacgata gaggtgaatg ggttctacga cccggccgac    4440
gcgaccatcc ctgaggccgt cgcaacaatt ctgccggcaa ctgctgcgat tcgcctcca    4500 aagcttggcc tccgcacga ctcgcaaccc gaggcggagg ctcgcccgt gggcgaggcc    4560 tctgtgccaa ggcgggccac gagctcgagc aaattggcca ggacgcttgc catcgatgct    4620
tgcgactccg acgtgcgcgc cgccttgctg gacctggacg cgccaatcgc ggtcggcggc    4680
tcctcgcgcg cccaagtccc gccgtgccca gtgagcgcgc tcggaagcgc cgcctttcga    4740
gcggcacacg cgtcgatta tgcgctctac atgggcgcaa tggccaaagg cgtcgcgtca    4800
gcggagatgg tcatcgctgc tggcaaggcc cgcatgctcg cgtcatttgg cgcggggggg    4860
cttcccctgg gcgaggtcga agaggcgttg gacaagatcc aggccgctct gcccgagggg    4920
ccgttcgccg tcaacctcat tcactcgccg ttcgatccaa accttgagga gggcaacgtc    4980
gagctgttcc tgaggcgcgg tatccggctg gtcgaggcct ctgcgttcat gtcggtcacg    5040
ccgtcgttgg tgcgctaccg agtcgccgga ctcgagcgag gccctggcgg gaccgcccga    5100
gtgctgaacc gcgtgattgg caaggtgagc cgtgcggagc tcgcagaaat gtttatgcgg    5160
ccgcctcccg ccgcgatcgt ctccaagctc ctcgcccagg gcctggtcac tgaggagcag    5220
gcgtcacttg cagagatcgt cccactggtt gacgacgttg caatcgaagc cgactcgggc    5280
ggtcacacag acaaccgccc gatccacgtc gttttgcccg tcgtcctcgc gctgcgagac    5340
cgcgtcatgc gtgagtgcaa gtatccagcc gccaatcgcg tccgcgtggg cgccggaggc    5400
gggatcggct gccctgccgc ggcgcgagct gcgttcgaca tgggcgcagc attcgttctc    5460
acgggctcga tcaaccagct cacgcgccaa gctgggacga gcgacagcgt gcgtgctgcc    5520
cttgcacgcg cgacctactc ggacgtgaca atggcccggg cggccgatat gtttgaccag    5580
ggcgtcaagc tgcaggtctt gaagcgcggc acgatgttcc cggcgcgcgc aaacaagctg    5640
tacgagttgt tcaccactta ccagtcgctg acgcgatcc ctcgggctga gctggctcgc    5700
ctggaaaagc gagttttccg catgtccatc gacgaggttt ggaacgaaac caagcagttc    5760
tacgagaccc ggctcaacaa ccccgccaag gttcccgggc ggagcgcga ccccaagctc    5820 aagatgtcgc tctgctttcg gtggtacttg tcgaaaagct ccaagtgggc atcgactgga    5880
```

-continued

```
caagttgggc gcgagctgga ctaccaggtc tggtgcggcc ccacgattgg cgctttcaac    5940
gagttcgtga agggtccag cctcgacgcg gaggcttgcg gggggcggtt tccttgcgtt    6000
gtgcgcgtta accaggagat attatgtggc gctgcttacg agcagcgact ggcgcgtttc    6060
atgctgctcg ctggccggga agcgcggac gcgttggcgt acacggttgc ggaagccaga    6120
tag                                                                   6123
```

<210> SEQ ID NO 10
<211> LENGTH: 2915
<212> TYPE: PRT
<213> ORGANISM: T. aureum

<400> SEQUENCE: 10

| | | | | | | | | | | | | | | |
|---|---|---|---|---|---|---|---|---|---|---|---|---|---|---|
|Arg|Lys|Cys|Ile|Arg|Pro|Ser|Leu|Gly|His|His|Trp|Ala|Ile|Ile|Gly|
|1| | | |5| | | | |10| | | | |15| |

Val Leu Gly Arg Ala Leu Arg Ile Val Arg Pro Ile Arg Tyr Glu Ala
                20                  25                  30

Thr Asn Leu Arg Arg Leu Pro Arg Ser Gly Trp Leu Val Ala Leu Gly
            35                  40                  45

Leu Phe Cys Asp Leu Ser Ser Cys Ala Gly Lys Leu Asp Leu Gln Thr
 50                  55                  60

Arg Asp Thr Ala Lys Asp Pro Cys Cys Lys Arg Lys Trp Ser Ala Ser
65                  70                  75                  80

Arg Ala Pro Pro Arg Pro Arg Ala Glu Ala Asp Lys Ala Ser Asn Glu
                85                  90                  95

Met Glu Thr Lys Asp Asp Arg Val Ala Ile Val Gly Met Ser Ala Ile
            100                 105                 110

Leu Pro Cys Gly Glu Ser Val Arg Glu Ser Trp Glu Ala Ile Arg Glu
        115                 120                 125

Gly Leu Asp Cys Leu Gln Asp Leu Pro Ala Asp Arg Val Asp Ile Thr
130                 135                 140

Ala Tyr Tyr Asp Pro Asn Lys Thr Thr Lys Asp Lys Ile Tyr Cys Lys
145                 150                 155                 160

Arg Gly Gly Phe Ile Pro Glu Tyr Asp Phe Asp Ala Arg Glu Phe Gly
                165                 170                 175

Leu Asn Met Phe Gln Met Glu Asp Ser Asp Ala Asn Gln Thr Val Thr
            180                 185                 190

Leu Leu Lys Val Lys Glu Ala Leu Glu Asp Ala Gly Val Glu Pro Phe
        195                 200                 205

Thr Lys Lys Lys Asn Ile Gly Cys Val Leu Gly Ile Gly Gly Gly
210                 215                 220

Gln Lys Ala Ser His Glu Phe Tyr Ser Arg Leu Asn Tyr Val Val Val
225                 230                 235                 240

Glu Lys Val Leu Arg Lys Met Asn Leu Pro Asp Glu Val Val Glu Ala
                245                 250                 255

Ala Val Glu Lys Tyr Lys Ala Asn Phe Pro Glu Trp Arg Leu Asp Ser
            260                 265                 270

Phe Pro Gly Phe Leu Gly Asn Val Thr Ala Gly Arg Cys Ser Asn Val
        275                 280                 285

Phe Asn Met Glu Gly Met Asn Cys Val Val Asp Ala Ala Cys Ala Ser
290                 295                 300

Ser Leu Ile Ala Ile Lys Val Ala Ile Asp Glu Leu Leu His Gly Asp
305                 310                 315                 320

Cys Asp Thr Met Ile Ala Gly Ala Thr Cys Thr Asp Asn Ser Ile Gly

```
                   325                 330                 335
Met Tyr Met Ala Phe Ser Lys Thr Pro Val Phe Ser Thr Asp Gln Ser
            340                 345                 350
Val Lys Ala Tyr Asp Ala Lys Thr Lys Gly Met Leu Ile Gly Glu Gly
            355                 360                 365
Ser Ala Met Val Val Leu Lys Arg Tyr Ala Asp Ala Val Arg Asp Gly
    370                 375                 380
Asp Glu Ile His Ala Val Ile Arg Ala Cys Ala Ser Ser Asp Gly
385                 390                 395                 400
Lys Ala Ala Gly Ile Tyr Ala Pro Thr Val Ser Gly Gln Glu Ala
                405                 410                 415
Leu Arg Arg Ala Tyr Ala Arg Ala Gly Val Asp Pro Ser Thr Val Thr
            420                 425                 430
Leu Val Glu Gly His Gly Thr Gly Thr Pro Val Gly Asp Arg Ile Glu
            435                 440                 445
Leu Thr Ala Leu Arg Asn Val Phe Asp Ala Ala Asn Lys Gly Arg Lys
    450                 455                 460
Glu Thr Val Ala Val Gly Ser Ile Lys Ser Gln Ile Gly His Leu Lys
465                 470                 475                 480
Ala Val Ala Gly Phe Ala Gly Leu Val Lys Val Val Met Ala Leu Lys
                485                 490                 495
His Lys Thr Leu Pro Gln Thr Ile Asn Val His Asp Pro Pro Ala Leu
            500                 505                 510
His Asp Gly Ser Pro Ile Gln Asp Ser Ser Leu Tyr Ile Asn Thr Met
            515                 520                 525
Asn Arg Pro Trp Phe Thr Ala Pro Gly Val Pro Arg Arg Ala Gly Ile
    530                 535                 540
Ser Ser Phe Gly Phe Gly Gly Ala Asn Tyr His Ala Val Leu Glu Glu
545                 550                 555                 560
Ala Glu Pro Glu His Ala Lys Pro Tyr Arg Met Asn Gln Val Pro Gln
                565                 570                 575
Pro Val Leu Leu His Ala Ser Ser Ala Ser Leu Ala Ser Ile Cys
            580                 585                 590
Asp Ala Gln Ala Asp Ala Leu Gln Ala Ala Val Ser Pro Glu Ala Ser
            595                 600                 605
Lys His Ala Asp Tyr Arg Ala Ile Val Ala Phe His Glu Ala Phe Lys
    610                 615                 620
Leu Arg Ala Gly Val Pro Ala Gly His Ala Arg Ile Gly Phe Val Ser
625                 630                 635                 640
Gly Ser Ala Ala Ala Thr Leu Ala Val Leu Arg Ala Ala Ser Ala Lys
                645                 650                 655
Leu Lys Gln Ser Ser Ala Thr Leu Glu Trp Thr Leu Leu Arg Glu Gly
            660                 665                 670
Val Thr Tyr Arg Ser Ala Met His Thr Pro Gly Ser Val Ala Ala
    675                 680                 685
Leu Phe Ala Gly Gln Gly Ala Gln Tyr Thr His Met Phe Ala Asp Val
    690                 695                 700
Ala Met Asn Trp Pro Pro Phe Arg Ser Ala Val Gln Glu Met Asp Ala
705                 710                 715                 720
Ala Gln Val Thr Ala Ala Pro Lys Arg Leu Ser Glu Val Leu Tyr
                725                 730                 735
Pro Arg Lys Pro Tyr Ala Ala Glu Pro Glu Gln Asp Asn Lys Ala Ile
            740                 745                 750
```

-continued

```
Ser Met Thr Ile Asn Ser Gln Pro Ala Leu Met Ala Cys Ala Ala Gly
            755                 760                 765

Ala Phe Glu Val Phe Arg Gln Ala Gly Leu Ala Pro Asp His Val Ala
        770                 775                 780

Gly His Ser Leu Gly Glu Phe Gly Ala Leu Leu Ala Ala Gly Cys Ala
785                 790                 795                 800

Ser Arg Glu Glu Leu Phe Arg Leu Val Cys Ser Arg Ala Lys Ala Met
                805                 810                 815

Gln Asp Val Pro Lys Pro Ser Glu Gly Val Met Ala Ala Val Ile Gly
            820                 825                 830

Arg Gly Ala Asp Lys Leu Thr Leu Gln Gly Asp Gly Ala Trp Leu Ala
        835                 840                 845

Asn Cys Asn Ser Pro Ser Gln Val Val Ile Ser Gly Asp Lys Thr Ala
850                 855                 860

Val Glu Arg Glu Ser Ser Arg Leu Ala Gly Leu Gly Phe Arg Ile Ile
865                 870                 875                 880

Pro Leu Ala Cys Glu Gly Ala Phe His Ser Pro His Met Thr Ala Ala
                885                 890                 895

Gln Ala Thr Phe Gln Ala Ala Leu Asp Ser Leu Lys Ile Ser Thr Pro
            900                 905                 910

Thr Asn Gly Ala Arg Leu Tyr Asn Asn Val Ser Gly Lys Thr Cys Arg
        915                 920                 925

Ser Leu Gly Glu Leu Arg Asp Cys Leu Gly Lys His Met Thr Ser Pro
930                 935                 940

Val Leu Phe Gln Ala Gln Val Glu Asn Met Tyr Ala Ala Gly Ala Arg
945                 950                 955                 960

Ile Phe Val Glu Phe Gly Pro Lys Gln Val Leu Ser Lys Leu Val Gly
                965                 970                 975

Glu Ile Leu Ala Asp Lys Ser Asp Phe Val Thr Val Ala Val Asn Ser
            980                 985                 990

Ser Ser Ser Lys Asp Ser Asp Val Gln Leu Arg Glu Ala Ala Ala Lys
        995                 1000                1005

Leu Ala Val Leu Gly Val Pro Leu Ala Asn Phe Asp Pro Trp Glu Leu
    1010                1015                1020

Cys Asp Ala Arg Arg Leu Arg Glu Cys Pro Arg Ser Lys Thr Thr Leu
1025                1030                1035                1040

Arg Leu Ser Ala Ala Thr Tyr Val Ser Asn Lys Thr Leu Ala Ala Arg
                1045                1050                1055

Glu Lys Val Met Glu Asp Asn Cys Asp Phe Ser Ser Leu Phe Ala Ser
            1060                1065                1070

Gly Pro Ala Ser Gln Glu Met Glu Arg Glu Ile Ala Asn Leu Arg Ala
        1075                1080                1085

Glu Leu Glu Ala Ala Gln Arg Gln Leu Asp Thr Ala Lys Thr Gln Leu
    1090                1095                1100

Ala Arg Lys Gln Val Gln Asp Pro Thr Ala Asp Arg Gln Arg Asp Met
1105                1110                1115                1120

Ile Ala Lys His Arg Ser Thr Leu Ala Ala Met Val Lys Glu Phe Glu
                1125                1130                1135

Ala Leu Ala Ser Gly Ser Pro Cys Ala Val Pro Phe Ala Pro Val Val
            1140                1145                1150

Asp Thr Ala Val Glu Asp Val Pro Phe Ala Asp Lys Val Ser Thr Pro
        1155                1160                1165

Pro Pro Gln Val Thr Ser Ala Pro Ile Ala Glu Leu Ala Arg Ala Glu
    1170                1175                1180
```

```
Ala Val Val Met Glu Val Leu Ala Ala Lys Thr Gly Tyr Glu Val Asp
1185                1190                1195                1200

Met Ile Glu Ala Asp Met Leu Leu Asp Ala Glu Leu Gly Ile Asp Ser
            1205                1210                1215

Val Lys Arg Ile Glu Ile Leu Ala Ala Val Gln Ala Gln Leu Gly Val
        1220                1225                1230

Glu Ala Lys Asp Val Asp Ala Leu Ser Arg Thr Arg Thr Val Gly Glu
    1235                1240                1245

Val Val Asp Ala Met Lys Ala Glu Ile Gly Gly Gln Ala Thr Ser Ala
1250                1255                1260

Pro Ser Pro Met Ala Gln Pro Gln Ala Ser Ala Pro Ser Pro Ser Pro
1265                1270                1275                1280

Thr Ala Ser Val Leu Pro Lys Pro Val Ala Leu Pro Ala Ser Val Asp
            1285                1290                1295

Pro Ala Lys Leu Ala Arg Ala Glu Ala Val Val Met Glu Val Leu Ala
        1300                1305                1310

Ala Lys Thr Gly Tyr Glu Val Asp Met Ile Glu Ala Asp Met Leu Leu
    1315                1320                1325

Asp Ala Glu Leu Gly Ile Asp Ser Val Lys Arg Ile Glu Ile Leu Ala
    1330                1335                1340

Ala Val Gln Ala Gln Leu Gly Val Glu Ala Lys Asp Val Asp Ala Leu
1345                1350                1355                1360

Ser Arg Thr Arg Thr Val Gly Glu Val Val Asp Ala Met Lys Ala Glu
            1365                1370                1375

Ile Gly Gly Gln Ala Thr Ser Ala Pro Ala Ser Val Ala Gln Pro Gln
        1380                1385                1390

Ala Ser Ala Pro Ser Pro Ser Ala Thr Thr Ala Ser Val Leu Pro Lys
    1395                1400                1405

Pro Val Ala Ala Pro Thr Ser Ala Asp Pro Ala Lys Leu Ala Arg Ala
    1410                1415                1420

Glu Ala Val Val Met Glu Val Leu Ala Ala Lys Thr Gly Tyr Glu Val
1425                1430                1435                1440

Asp Met Ile Glu Ala Asp Met Leu Leu Asp Ala Glu Leu Gly Ile Asp
            1445                1450                1455

Ser Val Lys Arg Ile Glu Ile Leu Ala Ala Val Gln Ala Gln Leu Gly
        1460                1465                1470

Val Glu Ala Lys Asp Val Asp Ala Leu Ser Arg Thr Arg Thr Val Gly
    1475                1480                1485

Glu Val Val Glu Ala Met Lys Ala Glu Ile Gly Gly Gln Ala Thr Ser
    1490                1495                1500

Ala Pro Ala Ser Val Ala Gln Pro Gln Ile Ser Val Ser Pro Thr Pro
1505                1510                1515                1520

Leu Ala Ala Ser Pro Ser Ala Asp Pro Ala Lys Leu Ala Arg Ala Glu
            1525                1530                1535

Ala Val Val Met Glu Val Leu Ala Ala Lys Thr Gly Tyr Glu Val Asp
        1540                1545                1550

Met Ile Glu Ala Asp Met Leu Leu Asp Ala Glu Leu Gly Ile Asp Ser
    1555                1560                1565

Val Lys Arg Ile Glu Ile Leu Ala Ala Val Gln Ala Gln Leu Gly Val
    1570                1575                1580

Glu Ala Lys Asp Val Asp Ala Leu Ser Arg Thr Arg Thr Val Gly Glu
1585                1590                1595                1600

Val Val Asp Ala Met Lys Ala Glu Ile Gly Gly Gln Ala Thr Ser Ala
```

-continued

Pro Ala Ser Val Ala Gln Pro Gln Ala Ser Pro Ser Pro Ser Ala
            1605                1610                1615
Thr Ala Ser Val Leu Pro Lys Pro Val Ala Ala Pro Thr Ser Ala Asp
    1620                1625                1630
Pro Ala Lys Leu Ala Arg Ala Glu Ala Val Val Met Glu Val Leu Ala
1635                1640                1645
Ala Lys Thr Gly Tyr Glu Val Asp Met Ile Glu Ala Asp Met Leu Leu
1650                1655                1660
Asp Ala Glu Leu Gly Ile Asp Ser Val Lys Arg Ile Glu Ile Leu Ala
1665                1670                1675            1680
Ala Val Gln Ala Gln Leu Gly Val Glu Ala Lys Asp Val Asp Ala Leu
        1685                1690                1695
Ser Arg Thr Arg Thr Val Gly Glu Val Val Glu Ala Met Lys Ala Glu
    1700                1705                1710
Ile Gly Gly Gln Ala Thr Ser Ala Pro Ala Ser Met Ala Gln Pro Gln
1715                1720                1725
Ile Ser Val Ser Pro Thr Pro Leu Ala Ala Ser Pro Ser Ala Asp Pro
1730                1735                1740
Ala Lys Leu Ala Arg Ala Glu Ala Val Val Met Glu Val Leu Ala Ala
1745                1750                1755            1760
Lys Thr Gly Tyr Glu Val Asp Met Ile Glu Ala Asp Met Leu Leu Asp
        1765                1770                1775
Ala Glu Leu Gly Ile Asp Ser Val Lys Arg Ile Glu Ile Leu Ala Ala
    1780                1785                1790
Val Gln Ala Gln Leu Gly Val Glu Ala Lys Asp Val Asp Ala Leu Ser
1795                1800                1805
Arg Thr Arg Thr Val Gly Glu Val Val Asp Ala Met Lys Ala Glu Ile
1810                1815                1820
Gly Gly Gln Ala Thr Ser Ala Pro Ala Ser Val Ala Gln Pro Gln Ala
1825                1830                1835            1840
Ser Ala Pro Ser Pro Ser Ala Thr Ala Ser Ala Pro Val Thr Pro Leu
        1845                1850                1855
Ala Ala Pro Ala Ser Val Asp Pro Ala Lys Leu Ala Arg Ala Glu Ala
    1860                1865                1870
Val Val Met Glu Val Leu Ala Ala Lys Thr Gly Tyr Glu Val Asp Met
1875                1880                1885
Ile Glu Ala Asp Met Leu Leu Asp Ala Glu Leu Gly Ile Asp Ser Val
1890                1895                1900
Lys Arg Ile Glu Ile Leu Ala Ala Val Gln Ala Gln Leu Gly Val Glu
1905                1910                1915            1920
Ala Lys Asp Val Asp Ala Leu Ser Arg Thr Arg Thr Val Gly Glu Val
        1925                1930                1935
Val Asp Ala Met Lys Ala Glu Ile Gly Gly Gln Ala Thr Ser Ala Pro
    1940                1945                1950
Ala Ser Val Ala Gln Pro Gln Ala Ser Ala Pro Ser Pro Ser Ala Thr
1955                1960                1965
Ala Ser Val Leu Pro Lys Pro Val Ala Ser Pro Ala Ser Val Asp Pro
1970                1975                1980
Ala Lys Leu Ala Arg Ala Glu Ala Val Val Met Glu Val Leu Ala Ala
1985                1990                1995            2000
Lys Thr Gly Tyr Glu Val Asp Met Ile Asp Ala Asp Met Leu Leu Asp
        2005                2010                2015
                            2020                2025                2030

```
Ala Glu Leu Gly Ile Asp Ser Val Lys Arg Ile Glu Ile Leu Ala Ala
        2035                2040                2045

Val Gln Ala Gln Leu Gly Val Glu Ala Lys Asp Val Asp Ala Leu Ser
2050                2055                2060

Arg Thr Arg Thr Val Gly Glu Val Val Glu Ala Met Lys Ala Glu Ile
2065                2070                2075                2080

Gly Ala Ala Gly Pro Asn Asp Ala Gln Ala Ala Ser Gly His Leu Phe
            2085                2090                2095

Gly Thr Gly Cys Glu Asp Leu Ser Leu Cys Ser Ala Ser Val Val Glu
            2100                2105                2110

Ile Ala Arg Cys Ser Glu Leu Ala Leu Glu Arg Pro Met Asp Arg Pro
        2115                2120                2125

Ile Leu Ile Val Ser Asp Gly Ser Ala Leu Pro Ala Ala Leu Ala Ser
        2130                2135                2140

Arg Leu Gly Ser Cys Ala Val Ile Leu Thr Thr Ala Gly Glu Thr Asp
2145                2150                2155                2160

Gln Ser Val Arg Ser Thr Lys His Val Asp Met Glu Gly Trp Gly Glu
            2165                2170                2175

Ala Asp Leu Val Arg Ala Leu Glu Ala Val Glu Ser Arg Phe Gly Val
            2180                2185                2190

Pro Gly Gly Val Val Leu Glu Arg Ala Ser Glu Thr Ala Arg Asp
            2195                2200                2205

Gln Leu Gly Phe Ala Leu Leu Leu Ala Lys His Ser Ser Lys Ala Leu
        2210                2215                2220

Asn Gln Gln Ile Pro Gly Gly Arg Ala Cys Phe Val Gly Val Ser Arg
2225                2230                2235                2240

Ile Asp Gly Lys Leu Gly Leu Ser Gly Ala Cys Ala Lys Gly Lys Gly
            2245                2250                2255

Trp Ala Glu Ala Ala Glu Ile Ala Gln Gln Gly Ala Val Ala Gly Leu
            2260                2265                2270

Cys Lys Thr Leu Asp Leu Glu Trp Pro His Val Phe Ala Arg Ser Ile
        2275                2280                2285

Asp Ile Glu Leu Gly Ala Asn Glu Glu Thr Ala Ala Gln Ala Ile Phe
        2290                2295                2300

Glu Glu Leu Ser Cys Pro Asp Leu Thr Val Arg Glu Ala Gly Tyr Thr
2305                2310                2315                2320

Lys Asp Gly Lys Arg Trp Thr Thr Glu Ala Arg Pro Val Gly Leu Gly
            2325                2330                2335

Lys Pro Lys Gln Ala Leu Arg Ser Ser Asp Val Phe Leu Val Ser Gly
            2340                2345                2350

Gly Ala Arg Gly Ile Thr Pro Val Cys Val Arg Glu Leu Ala Lys Ser
            2355                2360                2365

Ile Ser Gly Gly Thr Phe Val Leu Leu Gly Arg Ser Pro Leu Ala Asp
        2370                2375                2380

Asp Pro Ala Trp Ala Cys Gly Val Glu Glu Ala Asn Ile Gly Thr Ala
2385                2390                2395                2400

Ala Met Ala His Leu Lys Ala Glu Phe Ala Ala Gly Arg Gly Pro Lys
            2405                2410                2415

Pro Thr Pro Lys Ala His Lys Ala Leu Val Gly Ser Val Leu Gly Ala
            2420                2425                2430

Arg Glu Val Leu Gly Ser Leu Glu Ser Ile Arg Ala Gln Gly Ala Arg
        2435                2440                2445

Ala Glu Tyr Val Ser Cys Asp Val Ser Cys Ala Glu Arg Val Lys Ala
        2450                2455                2460
```

```
Val Val Asp Asp Leu Glu Arg Arg Val Gly Ala Val Thr Gly Val Val
2465                2470                2475                2480

His Ala Ser Gly Val Leu Arg Asp Lys Ser Val Arg Leu Glu Leu
            2485                2490                2495

Ala Asp Phe Glu Val Val Tyr Gly Thr Lys Val Asp Gly Leu Leu Asn
                2500                2505                2510

Leu Leu Gln Ala Val Asp Arg Pro Lys Leu Arg His Leu Val Leu Phe
            2515                2520                2525

Ser Ser Leu Ala Gly Phe His Gly Asn Thr Gly Gln Ala Val Tyr Ala
            2530                2535                2540

Met Ala Asn Glu Ala Leu Asn Lys Met Ala Phe His Leu Glu Thr Ala
2545                2550                2555                2560

Met Pro Gly Leu Ser Val Lys Thr Ile Gly Phe Gly Pro Trp Asp Gly
                2565                2570                2575

Gly Met Val Asn Asp Ala Leu Lys Ala His Phe Ala Ser Met Gly Val
                2580                2585                2590

Gln Ile Ile Pro Leu Asp Gly Gly Ala Glu Thr Val Ser Arg Ile Ile
            2595                2600                2605

Gly Ala Cys Ser Pro Thr Gln Val Leu Val Gly Asn Trp Gly Leu Pro
            2610                2615                2620

Pro Val Val Pro Asn Ala Ser Val His Lys Ile Thr Val Arg Leu Gly
2625                2630                2635                2640

Gly Glu Ser Ala Asn Pro Phe Leu Ser Ser His Thr Ile Gln Gly Arg
                2645                2650                2655

Lys Val Leu Pro Met Thr Val Ala Leu Gly Leu Leu Ala Glu Ala Ala
            2660                2665                2670

Arg Gly Leu Tyr Val Gly His Gln Val Val Gly Ile Glu Asp Ala Gln
            2675                2680                2685

Val Phe Gln Gly Val Val Leu Asp Lys Gly Ala Thr Cys Glu Val Gln
            2690                2695                2700

Leu Arg Arg Glu Ser Ser Thr Ala Ser Pro Ser Glu Val Val Leu Ser
2705                2710                2715                2720

Ala Ser Leu Asn Val Phe Ala Ala Gly Lys Val Pro Ala Tyr Arg
                2725                2730                2735

Ala His Val Leu Gly Ala Ser Gly Pro Arg Thr Gly Gly Val Gln
                2740                2745                2750

Leu Glu Leu Lys Asp Leu Gly Val Asp Ala Asp Pro Ala Cys Ser Val
            2755                2760                2765

Gly Lys Gly Ala Leu Tyr Asp Gly Arg Thr Leu Phe His Gly Pro Ala
2770                2775                2780

Phe Gln Tyr Met Asp Glu Val Leu Arg Cys Ser Pro Ala Glu Leu Ala
2785                2790                2795                2800

Val Arg Cys Arg Val Val Pro Ser Ala Ala Gln Asp Arg Gly Gln Phe
                2805                2810                2815

Val Ser Arg Gly Val Leu Tyr Asp Pro Phe Leu Asn Asp Thr Val Phe
            2820                2825                2830

Gln Ala Leu Leu Val Trp Ala Arg Leu Val Arg Asp Ser Ala Ser Leu
            2835                2840                2845

Pro Ser Asn Val Glu Arg Ile Ser Phe His Gly Gln Pro Pro Ser Glu
            2850                2855                2860

Gly Glu Val Phe Tyr Thr Thr Leu Lys Leu Asp Ser Ala Ala Ser Gly
2865                2870                2875                2880

Pro Leu Asp Pro Ile Ala Lys Ala Gln Phe Phe Leu His Arg Ala Cys
```

```
                2885                2890                2895
Gly Ala Val Phe Ala Ser Gly Arg Ala Ser Val Val Leu Asn Lys Ala
                2900                2905                2910

Leu Ser Phe
        2915

<210> SEQ ID NO 11
<211> LENGTH: 2040
<212> TYPE: PRT
<213> ORGANISM: T. aureum

<400> SEQUENCE: 11

Gln Ala Ile Gly His Arg Ala Ala Arg Trp Ser Cys Arg Ser Lys Ser
1               5                   10                  15

Lys Ala Arg Gly His Lys Ala Gln Lys Glu Met Asn Gln Gly Gly Arg
            20                  25                  30

Asn Asp Glu Gly Val Ser Val Ala Arg Ala Asp Pro Cys Pro Asp Thr
        35                  40                  45

Arg Ile Ala Val Val Gly Met Ala Val Glu Tyr Ala Gly Cys Arg Gly
    50                  55                  60

Lys Glu Ala Phe Trp Asp Thr Leu Met Asn Gly Lys Ile Asn Ser Ala
65                  70                  75                  80

Cys Ile Ser Asp Asp Arg Leu Gly Ser Ala Arg Arg Glu Glu His Tyr
                85                  90                  95

Ala Pro Glu Arg Ser Lys Tyr Ala Asp Thr Phe Cys Asn Glu Arg Tyr
            100                 105                 110

Gly Cys Ile Asp Pro Lys Val Asp Asn Glu His Asp Leu Leu Leu Gly
        115                 120                 125

Leu Ala Ala Ala Leu Gln Asp Ala Gln Asp Arg Arg Ser Asp Gly
    130                 135                 140

Gly Lys Phe Asp Pro Ala Gln Leu Lys Arg Cys Gly Ile Val Ser Gly
145                 150                 155                 160

Cys Leu Ser Phe Pro Met Asp Asn Leu Gln Gly Glu Leu Leu Asn Leu
                165                 170                 175

Tyr Gln Ala His Ala Glu Arg Arg Ile Gly Lys His Cys Phe Ala Asp
            180                 185                 190

Gln Thr Pro Trp Ser Thr Arg Thr Arg Ala Leu His Pro Leu Pro Gly
        195                 200                 205

Asp Pro Arg Thr His Arg Asp Pro Ala Ser Phe Val Ala Gly Gln Leu
    210                 215                 220

Gly Leu Gly Pro Leu His Tyr Ser Leu Asp Ala Ala Cys Ala Ser Ala
225                 230                 235                 240

Leu Tyr Val Leu Arg Leu Ala Gln Asp His Leu Leu Ser Gly Glu Ala
                245                 250                 255

Asp Leu Met Leu Cys Gly Ala Thr Cys Phe Pro Glu Pro Phe Phe Ile
            260                 265                 270

Leu Thr Gly Phe Ser Thr Phe His Ala Met Pro Val Gly Glu Asn Gly
        275                 280                 285

Val Ser Met Pro Phe His Arg Asp Thr Gln Gly Leu Thr Pro Gly Glu
    290                 295                 300

Gly Gly Ser Val Met Val Leu Lys Arg Leu Ala Asp Ala Glu Arg Asp
305                 310                 315                 320

Gly Asp His Ile Tyr Gly Thr Leu Leu Gly Ala Ser Leu Ser Asn Ala
                325                 330                 335

Gly Cys Gly Leu Pro Leu Lys Pro His Gln Pro Ser Glu Glu Ala Cys
```

-continued

```
                340                 345                 350
Leu Lys Ala Thr Tyr Glu Leu Val Gly Val Pro Pro Arg Asp Val Gln
            355                 360                 365

Tyr Val Glu Cys His Ala Thr Gly Thr Pro Gln Gly Asp Thr Val Glu
        370                 375                 380

Leu Gln Ala Val Lys Ala Cys Phe Glu Gly Ala Ser Pro Arg Ile Gly
385                 390                 395                 400

Ser Thr Lys Gly Asn Phe Gly His Thr Leu Val Ala Ala Gly Phe Ala
                405                 410                 415

Gly Met Cys Lys Val Leu Leu Ala Met Glu Arg Gly Val Ile Pro Pro
            420                 425                 430

Thr Pro Gly Val Asp Ser Gly Thr Gln Ile Asp Pro Leu Val Val Thr
        435                 440                 445

Ala Ala Leu Pro Trp Pro Asp Thr Arg Gly Pro Lys Arg Ala Gly
450                 455                 460

Leu Ser Ala Phe Gly Phe Gly Gly Thr Asn Ala His Ala Val Phe Glu
465                 470                 475                 480

Glu His Ile Pro Ser Arg Ala Pro Pro Ala Val Leu Cys Gln Pro Arg
                485                 490                 495

Leu Gly Ser Gly Pro Asn Arg Lys Leu Ala Ile Val Gly Met Asp Ala
            500                 505                 510

Thr Phe Gly Ser Leu Lys Gly Leu Ser Ala Leu Glu Ala Ala Leu Tyr
        515                 520                 525

Glu Ala Arg His Ala Ala Arg Pro Leu Pro Ala Lys Arg Trp Arg Phe
            530                 535                 540

Leu Gly Gly Asp Glu Ser Phe Leu His Glu Ile Gly Leu Glu Cys Ser
545                 550                 555                 560

Pro His Gly Cys Tyr Ile Glu Asp Val Asp Val Asp Phe Lys Arg Leu
                565                 570                 575

Arg Thr Pro Met Val Pro Glu Asp Leu Leu Arg Pro Gln Gln Leu Leu
            580                 585                 590

Ala Val Ser Thr Ile Asp Lys Ala Ile Leu Asp Ser Gly Leu Ala Lys
        595                 600                 605

Gly Gly Asn Val Ala Val Leu Val Gly Leu Gly Thr Asp Leu Glu Leu
    610                 615                 620

Tyr Arg His Arg Ala Arg Val Ala Leu Lys Glu Arg Leu Gln Gly Leu
625                 630                 635                 640

Val Arg Ser Ala Glu Gly Gly Ala Leu Thr Ser Arg Leu Met Asn Tyr
                645                 650                 655

Ile Asn Asp Ser Gly Thr Ser Thr Ser Tyr Thr Ser Tyr Ile Gly Asn
            660                 665                 670

Leu Val Ala Thr Arg Val Ser Ser Gln Trp Gly Phe Thr Gly Pro Ser
        675                 680                 685

Phe Thr Val Thr Glu Gly Ala Asn Ser Val His Arg Cys Ala Gln Leu
    690                 695                 700

Ala Lys Tyr Met Leu Asp Arg Gly Glu Val Asp Ala Val Val Val Ala
705                 710                 715                 720

Gly Val Asp Leu Cys Gly Ser Ala Glu Ala Phe Phe Val Arg Ser Arg
                725                 730                 735

Arg Met Gln Ile Ser Lys Ser Gln Arg Pro Ala Ala Pro Phe Asp Arg
            740                 745                 750

Ala Ala Asp Gly Phe Ala Gly Glu Gly Cys Gly Ala Leu Val Phe
        755                 760                 765
```

-continued

```
Lys Arg Leu Thr Asp Cys Val Ser Gly Glu Arg Ile Tyr Ala Ser Leu
    770             775                 780

Asp Ser Val Val Val Ala Thr Thr Pro Arg Ala Ala Leu Arg Ala Ala
785             790                 795                 800

Ala Gly Ser Ala Arg Val Asp Pro Ala Ser Ile Asp Met Val Glu Leu
                805                 810                 815

Ser Ala Asp Ser His Arg Phe Val Arg Ala Pro Gly Thr Val Ala Gln
            820                 825                 830

Pro Leu Thr Ala Glu Val Glu Val Gly Ala Val Arg Glu Val Ile Gly
        835                 840                 845

Thr Ala Gly Arg Gly Ser Arg Ser Val Ala Val Gly Ser Val Arg Ala
    850                 855                 860

Asn Val Gly Asp Ala Gly Phe Ala Ser Gly Ala Ala Ala Leu Val Lys
865                 870                 875                 880

Thr Ala Leu Cys Leu His Asn Arg Tyr Leu Ala Ala Thr Pro Gly Trp
                885                 890                 895

Asp Ala Pro Ala Ala Gly Val Asp Phe Gly Ala Glu Leu Tyr Val Cys
            900                 905                 910

Arg Glu Ser Arg Ala Trp Val Lys Asn Ala Gly Val Ala Arg His Ala
        915                 920                 925

Ala Ile Ser Gly Val Asp Glu Gly Gly Ser Cys Tyr Gly Leu Val Leu
    930                 935                 940

Ser Asp Val Pro Gly Gln Tyr Glu Thr Gly Asn Arg Ile Ser Leu Gln
945                 950                 955                 960

Ala Glu Ser Pro Lys Leu Leu Leu Ser Ala Pro Asp His Ala Ala
                965                 970                 975

Leu Leu Asp Lys Val Ala Ala Glu Leu Ala Leu Glu Gln Ala Asp
            980                 985                 990

Gly Leu Ser Ala Ala Ala Ala Val Asp Arg Leu Leu Gly Glu Ser
        995                 1000                1005

Leu Val Gly Cys Ala Ala Gly Ser Gly Gly Leu Thr Leu Cys Leu Val
    1010                1015                1020

Ala Ser Pro Ala Ser Leu His Lys Glu Leu Ala Leu Ala His Arg Gly
1025                1030                1035                1040

Ile Pro Arg Cys Ile Lys Ala Arg Arg Asp Trp Ala Ser Pro Ala Gly
                1045                1050                1055

Ser Tyr Phe Ala Pro Glu Pro Ile Ala Ser Asp Arg Val Ala Phe Met
            1060                1065                1070

Tyr Gly Glu Gly Arg Ser Pro Tyr Cys Gly Val Gly Arg Asp Leu His
        1075                1080                1085

Arg Ile Trp Pro Ala Leu His Glu Arg Val Asn Ala Lys Thr Val Asn
    1090                1095                1100

Leu Trp Gly Asp Gly Asp Ala Trp Leu Leu Pro Arg Ala Thr Ser Ala
1105                1110                1115                1120

Glu Glu Glu Glu Gln Leu Cys Arg Asn Phe Asp Ser Asn Gln Val Glu
                1125                1130                1135

Met Phe Arg Thr Gly Val Tyr Ile Ser Met Cys Leu Thr Asp Leu Ala
            1140                1145                1150

Arg Ser Leu Ile Gly Leu Gly Pro Lys Ala Ser Phe Gly Leu Ser Leu
        1155                1160                1165

Gly Glu Val Ser Met Leu Phe Ala Leu Ser Glu Ser Asn Cys Arg Leu
    1170                1175                1180

Ser Glu Glu Met Thr Arg Arg Leu Arg Ala Ser Pro Val Trp Asn Ser
1185                1190                1195                1200
```

```
Glu Leu Ala Val Glu Phe Asn Ala Leu Arg Lys Leu Trp Gly Val Ala
            1205                1210                1215
Pro Gly Ala Pro Val Asp Ser Phe Trp Gln Gly Tyr Val Val Arg Ala
        1220                1225                1230
Thr Arg Ala Gln Val Glu Gln Ala Ile Gly Glu Asp Asn Gln Phe Val
    1235                1240                1245
Arg Leu Leu Ile Val Asn Asp Ser Gln Ser Val Leu Ile Ala Gly Lys
1250                1255                1260
Pro Ala Ala Cys Glu Ala Val Ile Ala Arg Ile Gly Ser Ile Leu Pro
1265                1270                1275                1280
Pro Leu Gln Val Ser Gln Gly Met Val Gly His Cys Ala Glu Val Leu
        1285                1290                1295
Pro Tyr Thr Ser Glu Ile Gly Arg Ile His Asn Met Leu Arg Phe Pro
    1300                1305                1310
Ser Gln Asp Glu Thr Gly Gly Cys Lys Met Tyr Ser Ser Val Ser Asn
1315                1320                1325
Ser Arg Ile Gly Pro Val Glu Ser Gln Met Gly Pro Gly Thr Glu
    1330                1335                1340
Leu Val Phe Ser Pro Ser Met Glu Asp Phe Val Ala Gln Leu Tyr Ser
1345                1350                1355                1360
Arg Val Ala Asp Phe Pro Ala Ile Thr Glu Ala Val Tyr Gln Gln Gly
        1365                1370                1375
His Asp Val Phe Val Glu Val Gly Pro Asp His Ser Arg Ser Ala Ala
    1380                1385                1390
Val Arg Ser Thr Leu Gly Pro Thr Arg His Ile Ala Val Ala Met
        1395                1400                1405
Asp Arg Lys Gly Glu Ser Ala Trp Ser Gln Leu Leu Lys Met Leu Ala
    1410                1415                1420
Thr Leu Ala Ser His Arg Val Pro Gly Leu Asp Leu Ser Ser Met Tyr
1425                1430                1435                1440
His Pro Ala Val Val Glu Arg Cys Arg Leu Ala Leu Ala Ala Gln Arg
        1445                1450                1455
Ser Gly Gln Pro Glu Gln Arg Asn Lys Phe Leu Arg Thr Ile Glu Val
    1460                1465                1470
Asn Gly Phe Tyr Asp Pro Ala Asp Ala Thr Ile Pro Glu Ala Val Ala
    1475                1480                1485
Thr Ile Leu Pro Ala Thr Ala Ala Ile Ser Pro Pro Lys Leu Gly Ala
1490                1495                1500
Pro His Asp Ser Gln Pro Glu Ala Glu Ala Arg Pro Val Gly Glu Ala
1505                1510                1515                1520
Ser Val Pro Arg Arg Ala Thr Ser Ser Ser Lys Leu Ala Arg Thr Leu
            1525                1530                1535
Ala Ile Asp Ala Cys Asp Ser Asp Val Arg Ala Ala Leu Leu Asp Leu
        1540                1545                1550
Asp Ala Pro Ile Ala Val Gly Gly Ser Ser Arg Ala Gln Val Pro Pro
    1555                1560                1565
Cys Pro Val Ser Ala Leu Gly Ser Ala Ala Phe Arg Ala Ala His Gly
    1570                1575                1580
Val Asp Tyr Ala Leu Tyr Met Gly Ala Met Ala Lys Gly Val Ala Ser
1585                1590                1595                1600
Ala Glu Met Val Ile Ala Ala Gly Lys Ala Arg Met Leu Ala Ser Phe
        1605                1610                1615
Gly Ala Gly Gly Leu Pro Leu Gly Glu Val Glu Glu Ala Leu Asp Lys
```

```
                1620            1625            1630
Ile Gln Ala Ala Leu Pro Glu Gly Pro Phe Ala Val Asn Leu Ile His
        1635            1640            1645

Ser Pro Phe Asp Pro Asn Leu Glu Glu Gly Asn Val Glu Leu Phe Leu
    1650            1655            1660

Arg Arg Gly Ile Arg Leu Val Glu Ala Ser Ala Phe Met Ser Val Thr
1665            1670            1675            1680

Pro Ser Leu Val Arg Tyr Arg Val Ala Gly Leu Glu Arg Gly Pro Gly
            1685            1690            1695

Gly Thr Ala Arg Val Leu Asn Arg Val Ile Gly Lys Val Ser Arg Ala
        1700            1705            1710

Glu Leu Ala Glu Met Phe Met Arg Pro Pro Ala Ala Ile Val Ser
        1715            1720            1725

Lys Leu Leu Ala Gln Gly Leu Val Thr Glu Glu Gln Ala Ser Leu Ala
        1730            1735            1740

Glu Ile Val Pro Leu Val Asp Val Ala Ile Glu Ala Asp Ser Gly
1745            1750            1755            1760

Gly His Thr Asp Asn Arg Pro Ile His Val Val Leu Pro Val Val Leu
            1765            1770            1775

Ala Leu Arg Asp Arg Val Met Arg Glu Cys Lys Tyr Pro Ala Ala Asn
        1780            1785            1790

Arg Val Arg Val Gly Ala Gly Gly Ile Gly Cys Pro Ala Ala Ala
        1795            1800            1805

Arg Ala Ala Phe Asp Met Gly Ala Ala Phe Val Leu Thr Gly Ser Ile
        1810            1815            1820

Asn Gln Leu Thr Arg Gln Ala Gly Thr Ser Asp Ser Val Arg Ala Ala
1825            1830            1835            1840

Leu Ala Arg Ala Thr Tyr Ser Asp Val Thr Met Ala Pro Ala Ala Asp
            1845            1850            1855

Met Phe Asp Gln Gly Val Lys Leu Gln Val Leu Lys Arg Gly Thr Met
        1860            1865            1870

Phe Pro Ala Arg Ala Asn Lys Leu Tyr Glu Leu Phe Thr Thr Tyr Gln
        1875            1880            1885

Ser Leu Asp Ala Ile Pro Arg Ala Glu Leu Ala Arg Leu Glu Lys Arg
        1890            1895            1900

Val Phe Arg Met Ser Ile Asp Glu Val Trp Asn Glu Thr Lys Gln Phe
1905            1910            1915            1920

Tyr Glu Thr Arg Leu Asn Asn Pro Ala Lys Val Ala Arg Ala Glu Arg
            1925            1930            1935

Asp Pro Lys Leu Lys Met Ser Leu Cys Phe Arg Trp Tyr Leu Ser Lys
        1940            1945            1950

Ser Ser Lys Trp Ala Ser Thr Gly Gln Val Gly Arg Glu Leu Asp Tyr
        1955            1960            1965

Gln Val Trp Cys Gly Pro Thr Ile Gly Ala Phe Asn Glu Phe Val Lys
        1970            1975            1980

Gly Ser Ser Leu Asp Ala Glu Ala Cys Gly Gly Arg Phe Pro Cys Val
1985            1990            1995            2000

Val Arg Val Asn Gln Glu Ile Leu Cys Gly Ala Ala Tyr Glu Gln Arg
            2005            2010            2015

Leu Ala Arg Phe Met Leu Leu Ala Gly Arg Glu Ser Ala Asp Ala Leu
        2020            2025            2030

Ala Tyr Thr Val Ala Glu Ala Arg
        2035            2040
```

<210> SEQ ID NO 12
<211> LENGTH: 1476
<212> TYPE: DNA
<213> ORGANISM: T. aureum

<400> SEQUENCE: 12

```
atggagacaa aggacgatcg cgttgcgatc gtgggcatgt cggccatact gccttgcggt      60
gagtcagtgc gcgagtcgtg ggaggcgatt cgcgagggc tcgattgcct gcaggacctg     120
cctgcggacc gagtcgatat cacggcgtac tacgacccga acaagacaac caaggacaag     180
atctactgca agcgcggcgg cttcattccc gagtatgact tgacgcgcg cgagttcggc      240
ctcaacatgt tccagatgga ggactcggac gccaaccaaa ccgtgacttt gctcaaggtc     300
aaggaggctc tcgaggacgc cggggtggag cccttcacaa agaagaagaa gaacattggc     360
tgcgtgctcg gcatcggcgg cgggcagaag gcgagccacg agttttactc ccgactcaac     420
tatgtggtcg tggagaaggt gcttcgcaag atgaacctcc ccgacgaggt tgtcgaggcc     480
gccgtcgaaa agtacaaggc caactttcct gaatggcgcc tcgactcgtt ccctgggttt     540
cttggcaacg tgaccgccgg gcggtgcagc aacgtcttca acatggaagg catgaactgc     600
gtcgtggacg ctgcgtgcgc cagctcgctc atcgcgatca aggttgccat tgatgagctc     660
ctccacgggg actgcgacac catgattgcc ggtgcgacct gcaccgacaa ctcgatcggg     720
atgtacatgg ccttttccaa acccccagtt ttctccaccg accagagcgt caaggcgtac     780
gacgccaaga cgaaaggcat gctcatcggc gaaggctcgg ccatggtcgt gctcaagcgg     840
tacgcggacg ccgttcggga tggtgatgag atccatgccg tcatcagggc atgcgcctcg     900
tccagcgacg gcaaggctgc tggcatttac gcaccgacgg tgtcgggtca agaagaggca     960
ctgcggcgcg cgtacgcccg agctggcgtg gacccctcca ccgtcacgct ggtggagggc    1020
cacggcactg gcacacccgt cggggaccgg attgagctga ccgccttgcg caacgtcttt    1080
gacgcagcca acaaaggccg caaggaaaca gtcgcggtgg aagcatcaa gtcgcagatc     1140
ggtcacctga aggccgtggc cggctttgcc ggtctcgtca aggttgtcat ggccctcaag    1200
cacaagacgc tgccgcagac catcaacgtt acgacccgc cgcactgca cgacggctcg     1260
cccatccagg attcgagtct ttacatcaac acgatgaacc ggccctggtt tacggcacct    1320
ggcgtccccc gccgtgcagg catctctagc tttgggtttg gcggcgccaa ctaccacgct    1380
gttctcgaag aggccgagcc tgagcacgcg aagccgtatc gcatgaacca gttccacaa     1440
ccggtgctct tgcacgcaag ctccgcgtca gctctt                              1476
```

<210> SEQ ID NO 13
<211> LENGTH: 482
<212> TYPE: PRT
<213> ORGANISM: T. aureum

<400> SEQUENCE: 13

Met Glu Thr Lys Asp Asp Arg Val Ala Ile Val Gly Met Ser Ala Ile
1               5                   10                  15

Leu Pro Cys Gly Glu Ser Val Arg Glu Ser Trp Glu Ala Ile Arg Glu
            20                  25                  30

Gly Leu Asp Cys Leu Gln Asp Leu Pro Ala Asp Arg Val Asp Ile Thr
        35                  40                  45

Ala Tyr Tyr Asp Pro Asn Arg Gly Gly Phe Ile Pro Glu Tyr Asp Phe
    50                  55                  60

Asp Ala Arg Glu Phe Gly Leu Asn Met Phe Gln Met Glu Asp Ser Asp
65                  70                  75                  80

```
Ala Asn Gln Thr Val Thr Leu Leu Lys Val Lys Glu Ala Leu Glu Asp
                85                  90                  95

Ala Gly Val Glu Pro Phe Thr Lys Lys Lys Asn Ile Gly Cys Val
            100                 105                 110

Leu Gly Ile Gly Gly Gln Lys Ala Ser His Glu Phe Tyr Ser Arg
            115                 120                 125

Leu Asn Tyr Val Val Glu Lys Val Leu Arg Lys Met Asn Leu Pro
            130                 135                 140

Asp Glu Val Val Glu Ala Val Glu Lys Tyr Lys Ala Asn Phe Pro
145                 150                 155                 160

Glu Trp Arg Leu Asp Ser Phe Pro Gly Phe Leu Gly Asn Val Thr Ala
                165                 170                 175

Gly Arg Cys Ser Asn Val Phe Asn Met Glu Gly Met Asn Cys Val Val
                180                 185                 190

Asp Ala Ala Cys Ala Ser Ser Leu Ile Ala Ile Lys Val Ala Ile Asp
                195                 200                 205

Glu Leu Leu His Gly Asp Cys Asp Thr Met Ile Ala Gly Ala Thr Cys
    210                 215                 220

Thr Asp Asn Ser Ile Gly Met Tyr Met Ala Phe Ser Lys Thr Pro Val
225                 230                 235                 240

Phe Ser Thr Asp Gln Ser Val Lys Ala Tyr Asp Ala Lys Thr Lys Gly
                245                 250                 255

Met Leu Ile Gly Glu Gly Ser Ala Met Val Val Leu Lys Arg Tyr Ala
                260                 265                 270

Asp Ala Val Arg Asp Gly Asp Glu Ile His Ala Val Ile Arg Ala Cys
                275                 280                 285

Ala Ser Ser Asp Gly Lys Ala Ala Gly Ile Tyr Ala Pro Thr Val
    290                 295                 300

Ser Gly Gln Glu Glu Ala Leu Arg Arg Ala Tyr Ala Arg Ala Gly Val
305                 310                 315                 320

Asp Pro Ser Thr Val Thr Leu Val Glu Gly His Gly Thr Gly Thr Pro
                325                 330                 335

Val Gly Asp Arg Ile Glu Leu Thr Ala Leu Arg Asn Val Phe Asp Ala
                340                 345                 350

Ala Asn Lys Gly Arg Lys Glu Thr Val Ala Val Gly Ser Ile Lys Ser
                355                 360                 365

Gln Ile Gly His Leu Lys Ala Val Ala Gly Phe Ala Gly Leu Val Lys
    370                 375                 380

Val Val Met Ala Leu Lys His Lys Thr Leu Pro Gln Thr Ile Asn Val
385                 390                 395                 400

His Asp Pro Pro Ala Leu His Asp Gly Ser Pro Ile Gln Asp Ser Ser
                405                 410                 415

Leu Tyr Ile Asn Thr Met Asn Arg Pro Trp Phe Thr Ala Pro Gly Val
                420                 425                 430

Pro Arg Arg Ala Gly Ile Ser Ser Phe Gly Phe Gly Gly Ala Asn Tyr
                435                 440                 445

His Ala Val Leu Glu Glu Ala Glu Pro Glu His Ala Lys Pro Tyr Arg
    450                 455                 460

Met Asn Gln Val Pro Gln Pro Val Leu Leu His Ala Ser Ser Ala Ser
465                 470                 475                 480

Ala Leu
```

<210> SEQ ID NO 14

<211> LENGTH: 1329
<212> TYPE: DNA
<213> ORGANISM: T. aureum

<400> SEQUENCE: 14

```
cagtcgagtg cgacgctcga atggaccctg ctccgcgagg cgtcacgta ccgctccgcc      60
gcgatgcaca ctcctggcag tgtcgctgct ctgtttgccg ggcaaggcgc gcagtacacg     120
cacatgttcg ctgacgttgc catgaactgg ccaccgtttc gaagcgccgt gcaagagatg     180
gatgccgctc aagtcacggc ggcagcgccg aagcgcctca gcgaggtcct gtatccgcgc    240
aagccgtacg ctgcagagcc cgagcaagac aacaaggcca tctcgatgac gattaactcg    300
caaccggccc tcatggcctg cgctgctggg gcgtttgagg tgtttcgtca agctggtctt    360
gcgcccgacc acgtcgcggg tcattctctc ggcgagtttg gtgctttgct cgccgctgga    420
tgcgcaagcc gtgaggagct cttccgtctg gtctgcagca gagcgaaggc aatgcaagac    480
gttcccaagc aagcgaggg cgtcatggca gctgtcatcg gccgtggtgc tgacaagctc     540
acgctgcaag gcgatggtgc gtggcttgcc aactgcaact cgccaagcca agtggtcatt    600
tccggcgaca agactgctgt cgagcgtgaa tccagccggt tggcaggcct tggcttcagg    660
atcattccgc ttgcatgcga aggcgccttc cattcaccgc acatgacggc ggcccaggcc    720
acgtttcagg ctgcactgga cagcctcaag atctccaccc cgacgaacgg ggcgcgcctg    780
tacaacaacg tttccggaaa gacctgccga tccctgggtg aactccgcga ctgcctgggc    840
aagcacatga caagtcctgt gctcttccag gcacaggtag agaacatgta cgctgccggg    900
gcgcgcattt tcgtggagtt tggcccgaag caagtcctct ccaagctcgt aggcgagatt    960
ctcgccgaca gtcagactt tgtgacagtc gcggtcaact cgtcatcgtc caaggacagc   1020
gacgtgcaac ttcgtgaagc tgctgcgaag ctcgcggtcc ttggcgtccc gttggcgaac  1080
tttgaccctt gggagctctg cgacgcgcgg cgtcttcgcg aatgcccgcg atccaagacg  1140
acgttgcgct tgtctgcagc gacctacgtg tcgaacaaga cccttgctgc tagggagaag  1200
gtcatggagg acaactgcga cttttcttcg ctctttgcct ccggtccagc aagccaagag  1260
atggagcgag aaatagccaa ccttcgcgct gagctggagg cggcccaacg ccagcttgac  1320
acggccaaa                                                          1329
```

<210> SEQ ID NO 15
<211> LENGTH: 443
<212> TYPE: PRT
<213> ORGANISM: T. aureum

<400> SEQUENCE: 15

```
Gln Ser Ser Ala Thr Leu Glu Trp Thr Leu Leu Arg Glu Gly Val Thr
 1               5                  10                  15

Tyr Arg Ser Ala Ala Met His Thr Pro Gly Ser Val Ala Ala Leu Phe
            20                  25                  30

Ala Gly Gln Gly Ala Gln Tyr Thr His Met Phe Ala Asp Val Ala Met
        35                  40                  45

Asn Trp Pro Pro Phe Arg Ser Ala Val Gln Glu Met Asp Ala Ala Gln
    50                  55                  60

Val Thr Ala Ala Ala Pro Lys Arg Leu Ser Glu Val Leu Tyr Pro Arg
65                  70                  75                  80

Lys Pro Tyr Ala Ala Glu Pro Glu Gln Asp Asn Lys Ala Ile Ser Met
                85                  90                  95

Thr Ile Asn Ser Gln Pro Ala Leu Met Ala Cys Ala Ala Gly Ala Phe
            100                 105                 110
```

Glu Val Phe Arg Gln Ala Gly Leu Ala Pro Asp His Val Ala Gly His
    115                 120                 125

Ser Leu Gly Glu Phe Gly Ala Leu Leu Ala Ala Gly Cys Ala Ser Arg
130                 135                 140

Glu Glu Leu Phe Arg Leu Val Cys Ser Arg Ala Lys Ala Met Gln Asp
145                 150                 155                 160

Val Pro Lys Pro Ser Glu Gly Val Met Ala Ala Val Ile Gly Arg Gly
                165                 170                 175

Ala Asp Lys Leu Thr Leu Gln Gly Asp Gly Ala Trp Leu Ala Asn Cys
            180                 185                 190

Asn Ser Pro Ser Gln Val Val Ile Ser Gly Asp Lys Thr Ala Val Glu
        195                 200                 205

Arg Glu Ser Ser Arg Leu Ala Gly Leu Gly Phe Arg Ile Ile Pro Leu
    210                 215                 220

Ala Cys Glu Gly Ala Phe His Ser Pro His Met Thr Ala Ala Gln Ala
225                 230                 235                 240

Thr Phe Gln Ala Ala Leu Asp Ser Leu Lys Ile Ser Thr Pro Thr Asn
                245                 250                 255

Gly Ala Arg Leu Tyr Asn Asn Val Ser Gly Lys Thr Cys Arg Ser Leu
            260                 265                 270

Gly Glu Leu Arg Asp Cys Leu Gly Lys His Met Thr Ser Pro Val Leu
        275                 280                 285

Phe Gln Ala Gln Val Glu Asn Met Tyr Ala Ala Gly Ala Arg Ile Phe
    290                 295                 300

Val Glu Phe Gly Pro Lys Gln Val Leu Ser Lys Leu Val Gly Glu Ile
305                 310                 315                 320

Leu Ala Asp Lys Ser Asp Phe Val Thr Val Ala Val Asn Ser Ser Ser
                325                 330                 335

Ser Lys Asp Ser Asp Val Gln Leu Arg Glu Ala Ala Lys Leu Ala
            340                 345                 350

Val Leu Gly Val Pro Leu Ala Asn Phe Asp Pro Trp Glu Leu Cys Asp
        355                 360                 365

Ala Arg Arg Leu Arg Glu Cys Pro Arg Ser Lys Thr Thr Leu Arg Leu
    370                 375                 380

Ser Ala Ala Thr Tyr Val Ser Asn Lys Thr Leu Ala Arg Glu Lys
385                 390                 395                 400

Val Met Glu Asp Asn Cys Asp Phe Ser Ser Leu Phe Ala Ser Gly Pro
                405                 410                 415

Ala Ser Gln Glu Met Glu Arg Glu Ile Ala Asn Leu Arg Ala Glu Leu
            420                 425                 430

Glu Ala Ala Gln Arg Gln Leu Asp Thr Ala Lys
    435                 440

<210> SEQ ID NO 16
<211> LENGTH: 267
<212> TYPE: DNA
<213> ORGANISM: T. aureum

<400> SEQUENCE: 16
caagtcactt ccgctcccat cgccgagctc gcgcgcgccg aggccgtcgt catggaggtt     60
ctcgctgcca agactggcta cgaggtcgac atgatcgagg ccgacatgct gctcgacgcc    120
gagctcggca tcgactcggt caagcgcatt gagatcctgg cagctgtcca ggcccagctc    180
ggggtcgagg ccaaggacgt cgacgcgctc agccgcacac gaacagttgg cgaggtcgtt    240

```
gacgccatga aggctgagat cggcggg                                        267
```

<210> SEQ ID NO 17
<211> LENGTH: 89
<212> TYPE: PRT
<213> ORGANISM: T. aureum

<400> SEQUENCE: 17

```
Gln Val Thr Ser Ala Pro Ile Ala Glu Leu Ala Arg Ala Glu Ala Val
 1               5                  10                  15

Val Met Glu Val Leu Ala Ala Lys Thr Gly Tyr Glu Val Asp Met Ile
            20                  25                  30

Glu Ala Asp Met Leu Leu Asp Ala Glu Leu Gly Ile Asp Ser Val Lys
        35                  40                  45

Arg Ile Glu Ile Leu Ala Ala Val Gln Ala Gln Leu Gly Val Glu Ala
    50                  55                  60

Lys Asp Val Asp Ala Leu Ser Arg Thr Arg Thr Val Gly Glu Val Val
65                  70                  75                  80

Asp Ala Met Lys Ala Glu Ile Gly Gly
                85
```

<210> SEQ ID NO 18
<211> LENGTH: 2466
<212> TYPE: DNA
<213> ORGANISM: T. aureum

<400> SEQUENCE: 18

```
catctctttg gcacgggatg tgaagacctg agcctttgct ctgcttctgt ggttgagatt     60
gctcgttgca gcgaactagc tctggagcgc ccgatggatc ggcccattct tattgtaagc    120
gatggatcag cattgccggc ggctctggct agtcgactgg ggtcgtgtgc agtaatcctc    180
acgaccgcag gcgagaccga ccaatctgtg cgctcgacga agcacgttga catggaaggg    240
tggggcgagg cagatctcgt gcgcgctctt gaagcagtag agtctcgatt cggcgtccca    300
ggcggcgtcg tggtgcttga gcgcgcctca gaaacagcta gggaccagct tggctttgcc    360
ctgctgcttg ccaagcattc gagcaaagcg ctcaaccagc agatcccagg cgggcgcgcc    420
tgcttcgtgg gcgtctcgcg aatcgacgga agctcggac ttagcggagc ttgcgcgaaa    480
ggaaagggct gggctgaggc cgcagagatt gctcagcaag gagccgtcgc gggcttgtgc    540
aagaccttgg acctagagtg gccgcacgtc ttcgctcgca gcatcgacat cgagcttggc    600
gcgaacgaag aaacagctgc gcaagcaatc tttgaggagc tctcttgccc ggacctaacg    660
gtgcgcgaag caggatacac caaagacggc aagcggtgga cgactgaggc gcgaccggtt    720
gggcttggca gcccaagca ggcactacgt tcttcggacg tcttcttggt ttctggtggg    780
gcgcggggaa ttacacctgt ttgcgttcgc gagttggcca aatcgatcag tggtggcact    840
tttgtcctcc tcgggcggtc ccctctcgct gatgatccgg cgtgggcttg cggcgtcgag    900
gaagcaaaca ttgggacagc cgctatggcg cacctcaagg ccgagttcgc agccgggcgc    960
ggcccgaagc cgacgccaaa ggcccacaaa gcactcgttg ggagcgtcct ggggcgcgcg   1020
gaagtccttg gttcgctaga gagtattcgc gcccagggtg cgcgcgccga gtacgtttcc   1080
tgcgacgttt cgtgtgcgga gcgcgtcaag gccgtcgtcg acgatctcga gcgacgggtc   1140
ggggctgtaa ctgggggttgt gcacgcctct ggtgttctcc gagacaagtc cgttgagcgc   1200
ttggagctcg ccgacttcga ggtcgtgtac ggcaccaagg tggacggcct gctcaacctg   1260
ctgcaggccg tggaccgccc caaactccgg cacttggtcc tcttcagctc cctggccggt   1320
```

```
ttccacggca acactgggca ggccgtgtac gctatggcga atgaggcgct gaacaagatg    1380
gccttccatt tggaaactgc gatgcctggc ctctcggtca agacgatcgg gtttggacct    1440
tgggacggcg gcatggtcaa cgatgcgctg aaagcgcact ttgcgtctat gggcgtccaa    1500
attattccgc tcgacggcgg cgcggagacc gtttcccgaa tcatcgggcc gtgctcgcca    1560
acacaagttc tggttggcaa ctggggcttg cccctgtag ttcctaacgc gagcgtgcac     1620
aagattactg tgaggcttgg cggggagtct gcaaacccct tcctgtcctc gcacacgatt    1680
caaggcagaa aggtcttgcc gatgactgtg gcgcttgggc ttctcgctga ggcggctcga    1740
gggctctacg tcggtcacca gtagtcggg attgaggacg cccaagtctt ccagggagtc     1800
gtgttggaca aggggcgac gtgtgaggtc cagcttcgcc gcgagtcttc gactgcaagc     1860
ccaagcgagt tgtgctgag tgcttcgctc aatgtattcg cggcgggaaa ggttgtgcct     1920
gcgtaccgcg cgcatgtcgt gctcggcgct tcagggccac gcactggcgg cgtgcagctt    1980
gaactgaaag atttgggcgt ggacgccgac cctgcttgct ccgttggcaa gggtgcgctg    2040
tacgacggta ggacgctgtt ccatgggccg gcgtttcagt acatggatga ggttcttcgg    2100
tgctcgcctg cagagcttgc cgtgcggtgc cgtgtcgttc cgagcgcggc tcaggaccgc    2160
ggccaatttg tttcgcgcgg agtgttgtac gacccgttcc tgaacgacac ggtgttttcaa   2220
gctctccttg tttgggcccg tctggtcagg acagcgctt cgctaccgag caacgttgaa     2280
cgaatctcgt tccacggcca gccgccgagc gagggcgagg tgttttacac cacgctcaag    2340
ctggacagtg ctgcgagcgg gccgctcgac ccgattgcaa aggcgcagtt cttcctccac    2400
cgagcttgcg gggcggtctt tgcatcaggg cgagcgagtg tggttctgaa caaggctctt    2460
tcgttt                                                              2466
```

<210> SEQ ID NO 19
<211> LENGTH: 825
<212> TYPE: PRT
<213> ORGANISM: T. aureum

<400> SEQUENCE: 19

Ala Ser Gly His Leu Phe Gly Thr Gly Cys Glu Asp Leu Ser Leu Cys
1               5                   10                  15

Ser Ala Ser Val Val Glu Ile Ala Arg Cys Ser Glu Leu Ala Leu Glu
            20                  25                  30

Arg Pro Met Asp Arg Pro Ile Leu Ile Val Ser Asp Gly Ser Ala Leu
        35                  40                  45

Pro Ala Leu Ala Ser Arg Leu Gly Ser Cys Ala Val Ile Leu Thr
    50                  55                  60

Thr Ala Gly Glu Thr Asp Gln Ser Val Arg Ser Thr Lys His Val Asp
65                  70                  75                  80

Met Glu Gly Trp Gly Glu Ala Asp Leu Val Arg Ala Leu Glu Ala Val
                85                  90                  95

Glu Ser Arg Phe Gly Val Pro Gly Val Val Leu Glu Arg Ala
            100                 105                 110

Ser Glu Thr Ala Arg Asp Gln Leu Gly Phe Ala Leu Leu Leu Ala Lys
        115                 120                 125

His Ser Ser Lys Ala Leu Asn Gln Gln Ile Pro Gly Gly Arg Ala Cys
    130                 135                 140

Phe Val Gly Val Ser Arg Ile Asp Gly Lys Leu Gly Leu Ser Gly Ala
145                 150                 155                 160

Cys Ala Lys Gly Lys Gly Trp Ala Glu Ala Ala Glu Ile Ala Gln Gln
                165                 170                 175

```
Gly Ala Val Ala Gly Leu Cys Lys Thr Leu Asp Leu Glu Trp Pro His
                180                 185                 190

Val Phe Ala Arg Ser Ile Asp Ile Glu Leu Gly Ala Asn Glu Glu Thr
            195                 200                 205

Ala Ala Gln Ala Ile Phe Glu Glu Leu Ser Cys Pro Asp Leu Thr Val
        210                 215                 220

Arg Glu Ala Gly Tyr Thr Lys Asp Gly Lys Arg Trp Thr Thr Glu Ala
225                 230                 235                 240

Arg Pro Val Gly Leu Gly Lys Pro Lys Gln Ala Leu Arg Ser Ser Asp
                245                 250                 255

Val Phe Leu Val Ser Gly Gly Ala Arg Gly Ile Thr Pro Val Cys Val
            260                 265                 270

Arg Glu Leu Ala Lys Ser Ile Ser Gly Gly Thr Phe Val Leu Leu Gly
        275                 280                 285

Arg Ser Pro Leu Ala Asp Asp Pro Ala Trp Ala Cys Gly Val Glu Glu
290                 295                 300

Ala Asn Ile Gly Thr Ala Ala Met Ala His Leu Lys Ala Glu Phe Ala
305                 310                 315                 320

Ala Gly Arg Gly Pro Lys Pro Thr Pro Lys Ala His Lys Ala Leu Val
                325                 330                 335

Gly Ser Val Leu Gly Ala Arg Glu Val Leu Gly Ser Leu Glu Ser Ile
            340                 345                 350

Arg Ala Gln Gly Ala Arg Ala Glu Tyr Val Ser Cys Asp Val Ser Cys
        355                 360                 365

Ala Glu Arg Val Lys Ala Val Val Asp Asp Leu Glu Arg Arg Val Gly
370                 375                 380

Ala Val Thr Gly Val Val His Ala Ser Gly Val Leu Arg Asp Lys Ser
385                 390                 395                 400

Val Glu Arg Leu Glu Leu Ala Asp Phe Glu Val Val Tyr Gly Thr Lys
                405                 410                 415

Val Asp Gly Leu Leu Asn Leu Leu Gln Ala Val Asp Arg Pro Lys Leu
            420                 425                 430

Arg His Leu Val Leu Phe Ser Ser Leu Ala Gly Phe His Gly Asn Thr
        435                 440                 445

Gly Gln Ala Val Tyr Ala Met Ala Asn Glu Ala Leu Asn Lys Met Ala
        450                 455                 460

Phe His Leu Glu Thr Ala Met Pro Gly Leu Ser Val Lys Thr Ile Gly
465                 470                 475                 480

Phe Gly Pro Trp Asp Gly Gly Met Val Asn Asp Ala Leu Lys Ala His
                485                 490                 495

Phe Ala Ser Met Gly Val Gln Ile Ile Pro Leu Asp Gly Gly Ala Glu
            500                 505                 510

Thr Val Ser Arg Ile Ile Gly Ala Cys Ser Pro Thr Gln Val Leu Val
        515                 520                 525

Gly Asn Trp Gly Leu Pro Pro Val Pro Asn Ala Ser Val His Lys
        530                 535                 540

Ile Thr Val Arg Leu Gly Gly Glu Ser Ala Asn Pro Phe Leu Ser Ser
545                 550                 555                 560

His Thr Ile Gln Gly Arg Lys Val Leu Pro Met Thr Val Ala Leu Gly
                565                 570                 575

Leu Leu Ala Glu Ala Ala Arg Gly Leu Tyr Val Gly His Gln Val Val
            580                 585                 590

Gly Ile Glu Asp Ala Gln Val Phe Gln Gly Val Val Leu Asp Lys Gly
```

```
                595                 600                 605
Ala Thr Cys Glu Val Gln Leu Arg Arg Glu Ser Ser Thr Ala Ser Pro
    610                 615                 620

Ser Glu Val Val Leu Ser Ala Ser Leu Asn Val Phe Ala Ala Gly Lys
625                 630                 635                 640

Val Val Pro Ala Tyr Arg Ala His Val Leu Gly Ala Ser Gly Pro
                645                 650                 655

Arg Thr Gly Gly Val Gln Leu Glu Leu Lys Asp Leu Gly Val Asp Ala
            660                 665                 670

Asp Pro Ala Cys Ser Val Gly Lys Gly Ala Leu Tyr Asp Gly Arg Thr
        675                 680                 685

Leu Phe His Gly Pro Ala Phe Gln Tyr Met Asp Glu Val Leu Arg Cys
    690                 695                 700

Ser Pro Ala Glu Leu Ala Val Arg Cys Arg Val Val Pro Ser Ala Ala
705                 710                 715                 720

Gln Asp Arg Gly Gln Phe Val Ser Arg Gly Val Leu Tyr Asp Pro Phe
                725                 730                 735

Leu Asn Asp Thr Val Phe Gln Ala Leu Leu Val Trp Ala Arg Leu Val
            740                 745                 750

Arg Asp Ser Ala Ser Leu Pro Ser Asn Val Glu Arg Ile Ser Phe His
        755                 760                 765

Gly Gln Pro Pro Ser Glu Gly Glu Val Phe Tyr Thr Thr Leu Lys Leu
    770                 775                 780

Asp Ser Ala Ala Ser Gly Pro Leu Asp Pro Ile Ala Lys Ala Gln Phe
785                 790                 795                 800

Phe Leu His Arg Ala Cys Gly Ala Val Phe Ala Ser Gly Arg Ala Ser
                805                 810                 815

Val Val Leu Asn Lys Ala Leu Ser Phe
            820                 825

<210> SEQ ID NO 20
<211> LENGTH: 1383
<212> TYPE: DNA
<213> ORGANISM: T. aureum

<400> SEQUENCE: 20
atgaaccagg gcgggagaaa tgacgagggc gtctcggtgg cgcgcgcgga cccatgccct      60
gacacgcgga tcgctgtcgt gggcatggcg gtcgagtatg cagggtgccg cggcaaggaa     120
gcgttctggg acacgctcat gaacggcaaa atcaactctg cctgtatctc agacgatcgc     180
ctcgggtcag cacgacgaga gagcactat gcgcccgaga ggtcaaagta cgccgatacg      240
ttctgcaacg agaggtacgg atgcatcgat cccaaagtcg acaacgagca cgacctgctc     300
ctcggcctcg ccgcggctgc gcttcaagac gcgcaggaca ggcgcagcga cggcggcaag     360
ttcgacccag cgcagctcaa cgctgcggc attgtcagcg ctgcctgtc cttcccgatg       420 gacaacctgc aaggcgagct gctcaacctt taccagccc atgctgagag gcggattggc      480
aagcattgct tcgcggacca aacgcctgg tcgacgcgaa ccagagcgct tcacccgctg      540 cccgggacc cgaggaccca ccgcgaccca gcctccttcg tcgccggaca gctcggcctc     600
ggcccgctgc actactcgct cgacgccgcc tgcgcctcgg ccctttacgt tctgcgactc    660
gctcaggacc acctcctctc gggcgaggct gacttgatgc tgtgcggagc gacgtgcttc    720
ccagagccct tcttcatcct gactgggttt agcacgttcc acgcgatgcc agtcggtgag   780
aacggtgtct cgatgccgtt tcatcgggac acgcaagggc tgacgcccgg cgagggcggc    840
```

```
tcggtgatgg tgctcaagcg cctcgcggac gccgagcgcg acggagacca catctacggg    900
acgcttcttg gagccagctt gagcaacgca ggctgcgggc ttcctctcaa gccgcaccag    960
ccaagcgagg aggcctgctt gaaagccacc tacgagctcg tcggcgtgcc gccccgagac   1020
gtccagtacg tcgagtgcca cgccaccggc acgccgcagg gcgacaccgt cgagctccaa   1080
gccgtcaaag cctgctttga gggcgcaagc ccccggatcg ggtccacgaa aggcaacttc   1140
ggacacaccc tcgtcgcggc cggctttgcg ggaatgtgca aggttctcct tgcaatggag   1200
cgcggcgtga tcccccgac cccgggcgtt gactctggca cccagattga tccctcgtc    1260 gtcacagcgg cgctcccgtg gccggatacg cgcggcgggc cgaaacgcgc aggactctcc   1320
gcattcggat tcggggcac aaacgcgcac gccgtctttg aggagcatat tccctcgaga   1380
gct                                                                1383
```

<210> SEQ ID NO 21
<211> LENGTH: 461
<212> TYPE: PRT
<213> ORGANISM: T. aureum

<400> SEQUENCE: 21

```
Met Asn Gln Gly Gly Arg Asn Asp Glu Gly Val Ser Val Ala Arg Ala
 1               5                  10                  15

Asp Pro Cys Pro Asp Thr Arg Ile Ala Val Val Gly Met Ala Val Glu
            20                  25                  30

Tyr Ala Gly Cys Arg Gly Lys Glu Ala Phe Trp Asp Thr Leu Met Asn
        35                  40                  45

Gly Lys Ile Asn Ser Ala Cys Ile Ser Asp Asp Arg Leu Gly Ser Ala
    50                  55                  60

Arg Arg Glu Glu His Tyr Ala Pro Glu Arg Ser Lys Tyr Ala Asp Thr
65                  70                  75                  80

Phe Cys Asn Glu Arg Tyr Gly Cys Ile Asp Pro Lys Val Asp Asn Glu
                85                  90                  95

His Asp Leu Leu Leu Gly Leu Ala Ala Ala Leu Gln Asp Ala Gln
            100                 105                 110

Asp Arg Arg Ser Asp Gly Gly Lys Phe Asp Pro Ala Gln Leu Lys Arg
        115                 120                 125

Cys Gly Ile Val Ser Gly Cys Leu Ser Phe Pro Met Asp Asn Leu Gln
    130                 135                 140

Gly Glu Leu Leu Asn Leu Tyr Gln Ala His Ala Glu Arg Arg Ile Gly
145                 150                 155                 160

Lys His Cys Phe Ala Asp Gln Thr Pro Trp Ser Thr Arg Thr Arg Ala
                165                 170                 175

Leu His Pro Leu Pro Gly Asp Pro Arg Thr His Arg Asp Pro Ala Ser
            180                 185                 190

Phe Val Ala Gly Gln Leu Gly Leu Gly Pro Leu His Tyr Ser Leu Asp
        195                 200                 205

Ala Ala Cys Ala Ser Ala Leu Tyr Val Leu Arg Leu Ala Gln Asp His
    210                 215                 220

Leu Leu Ser Gly Glu Ala Asp Leu Met Leu Cys Gly Ala Thr Cys Phe
225                 230                 235                 240

Pro Glu Pro Phe Phe Ile Leu Thr Gly Phe Ser Thr Phe His Ala Met
                245                 250                 255

Pro Val Gly Glu Asn Gly Val Ser Met Pro Phe His Arg Asp Thr Gln
            260                 265                 270

Gly Leu Thr Pro Gly Glu Gly Gly Ser Val Met Val Leu Lys Arg Leu
```

```
                275                 280                 285
Ala Asp Ala Glu Arg Asp Gly Asp His Ile Tyr Gly Thr Leu Leu Gly
        290                 295                 300
Ala Ser Leu Ser Asn Ala Gly Cys Gly Leu Pro Leu Lys Pro His Gln
305                 310                 315                 320
Pro Ser Glu Glu Ala Cys Leu Lys Ala Thr Tyr Glu Leu Val Gly Val
                325                 330                 335
Pro Pro Arg Asp Val Gln Tyr Val Glu Cys His Ala Thr Gly Thr Pro
            340                 345                 350
Gln Gly Asp Thr Val Glu Leu Gln Ala Val Lys Ala Cys Phe Glu Gly
        355                 360                 365
Ala Ser Pro Arg Ile Gly Ser Thr Lys Gly Asn Phe Gly His Thr Leu
370                 375                 380
Val Ala Ala Gly Phe Ala Gly Met Cys Lys Val Leu Leu Ala Met Glu
385                 390                 395                 400
Arg Gly Val Ile Pro Pro Thr Pro Gly Val Asp Ser Gly Thr Gln Ile
                405                 410                 415
Asp Pro Leu Val Val Thr Ala Ala Leu Pro Trp Pro Asp Thr Arg Gly
            420                 425                 430
Gly Pro Lys Arg Ala Gly Leu Ser Ala Phe Gly Phe Gly Gly Thr Asn
        435                 440                 445
Ala His Ala Val Phe Glu Glu His Ile Pro Ser Arg Ala
    450                 455                 460

<210> SEQ ID NO 22
<211> LENGTH: 1335
<212> TYPE: DNA
<213> ORGANISM: T. aureum

<400> SEQUENCE: 22
cagcctcgcc tcggcagcgg accaaaccga aagcttgcta tcgtcggcat ggatgccacg      60
tttggatcct tgaagggtct ctccgcacta gaagctgcgc tttacgaggc aaggcacgct    120
gcgcggcccc tgcctgcgaa gcgctggcgc ttcttgggcg gggacgagtc ctttctccac    180
gagatcggac tcgagtgctc tccgcacggg tgctacattg aggacgtgga tgtggacttt    240
aagcgactcc gcacgccaat ggtgccggag gacttgctcc ggccgcaaca gctcctggcc    300
gtgtcgacga ttgacaaggc catcctcgac tcgggcttgg ccaagggcgg caacgtggct    360
gtccttgtcg gcctcgggac ggacctcgag ctctaccgcc accgagctcg ggttgcgctt    420
aaggagcgtc ttcaaggact ggttcgctct gccgagggag gagccctgac gtctcgcctg    480
atgaactata tcaatgatag cggaacgtcg acctcctaca cgtcgtatat cggcaacctc    540
gtcgccacgc gcgtctcgtc ccagtggggc ttcactgggc cgtcgttcac cgtcacggaa    600
ggggccaact cggtccatcg gtgcgcccag ctcgccaagt acatgctcga ccgcggcgag    660
gtcgacgccg tcgtggttgc aggagtcgac ctgtgcggga cgccgaggc gttcttcgtg    720
aggtcgcgcc gcatgcagat ctcgaaaagt cagcgcccgg ccgcgccgtt gaccgcgcc    780
gcagacggct tcttcgcggg ggaagggtgc ggcgccctcg tcttcaaacg cctgactgac    840
tgtgtgtctg gcgagcgaat ctacgcgtcc ctcgactcgg tcgtcgtcgc aaccacgccg    900
cgcgccgctc ttcgtgctgc cgcagggtcg gcgcgggttg acccagccag catcgacatg    960
gtcgagctga gcgcagattc ccaccggttt gtgcgggcgc aggcaccgt ggctcagcct    1020
ctgacagcca aagtcgaggt cggggcggtg cgggaagtga tcgggaccgc ggggaggggc    1080
tctcgaagcg tggccgtcgg atcggtccgc gccaacgtcg gggacgcagg gtttgcttcc    1140
```

```
ggggccgctg ccctcgtaaa aactgcgctc tgcttgcaca accgctactt ggcggctacc    1200
ccaggctggg atgcgcctgc tgccggcgtg gattttggtg ccgagctgta cgtttgccgc    1260
gagtcgcgtg cttgggtcaa gaacgccggc gttgcacggc acgccgcaat tctggcgtg    1320 gacgaaggcg ggtcg                                                    1335
```

<210> SEQ ID NO 23
<211> LENGTH: 445
<212> TYPE: PRT
<213> ORGANISM: T. aureum

<400> SEQUENCE: 23

| | | | | | | | | | | | | | | | |
|---|---|---|---|---|---|---|---|---|---|---|---|---|---|---|---|
| Gln | Pro | Arg | Leu | Gly | Ser | Gly | Pro | Asn | Arg | Lys | Leu | Ala | Ile | Val | Gly |
| 1 | | | | 5 | | | | | 10 | | | | | 15 | |
| Met | Asp | Ala | Thr | Phe | Gly | Ser | Leu | Lys | Gly | Leu | Ser | Ala | Leu | Glu | Ala |
| | | 20 | | | | | 25 | | | | | 30 | | | |
| Ala | Leu | Tyr | Glu | Ala | Arg | His | Ala | Ala | Arg | Pro | Leu | Pro | Ala | Lys | Arg |
| | | | 35 | | | | | 40 | | | | | 45 | | |
| Trp | Arg | Phe | Leu | Gly | Gly | Asp | Glu | Ser | Phe | Leu | His | Glu | Ile | Gly | Leu |
| | 50 | | | | | 55 | | | | | 60 | | | | |
| Glu | Cys | Ser | Pro | His | Gly | Cys | Tyr | Ile | Glu | Asp | Val | Asp | Val | Asp | Phe |
| 65 | | | | | 70 | | | | | 75 | | | | | 80 |
| Lys | Arg | Leu | Arg | Thr | Pro | Met | Val | Pro | Glu | Asp | Leu | Leu | Arg | Pro | Gln |
| | | | | 85 | | | | | 90 | | | | | 95 | |
| Gln | Leu | Leu | Ala | Val | Ser | Thr | Ile | Asp | Lys | Ala | Ile | Leu | Asp | Ser | Gly |
| | | | 100 | | | | | 105 | | | | | 110 | | |
| Leu | Ala | Lys | Gly | Gly | Asn | Val | Ala | Val | Leu | Val | Gly | Leu | Gly | Thr | Asp |
| | | | | 115 | | | | | 120 | | | | | 125 | |
| Leu | Glu | Leu | Tyr | Arg | His | Arg | Ala | Arg | Val | Ala | Leu | Lys | Glu | Arg | Leu |
| | 130 | | | | | 135 | | | | | 140 | | | | |
| Gln | Gly | Leu | Val | Arg | Ser | Ala | Glu | Gly | Gly | Ala | Leu | Thr | Ser | Arg | Leu |
| 145 | | | | | 150 | | | | | 155 | | | | | 160 |
| Met | Asn | Tyr | Ile | Asn | Asp | Ser | Gly | Thr | Ser | Thr | Ser | Tyr | Thr | Ser | Tyr |
| | | | | 165 | | | | | 170 | | | | | 175 | |
| Ile | Gly | Asn | Leu | Val | Ala | Thr | Arg | Val | Ser | Ser | Gln | Trp | Gly | Phe | Thr |
| | | | 180 | | | | | 185 | | | | | 190 | | |
| Gly | Pro | Ser | Phe | Thr | Val | Thr | Glu | Gly | Ala | Asn | Ser | Val | His | Arg | Cys |
| | | | | 195 | | | | | 200 | | | | | 205 | |
| Ala | Gln | Leu | Ala | Lys | Tyr | Met | Leu | Asp | Arg | Gly | Glu | Val | Asp | Ala | Val |
| | 210 | | | | | 215 | | | | | 220 | | | | |
| Val | Val | Ala | Gly | Val | Asp | Leu | Cys | Gly | Ser | Ala | Glu | Ala | Phe | Phe | Val |
| 225 | | | | | 230 | | | | | 235 | | | | | 240 |
| Arg | Ser | Arg | Arg | Met | Gln | Ile | Ser | Lys | Ser | Gln | Arg | Pro | Ala | Ala | Pro |
| | | | | 245 | | | | | 250 | | | | | 255 | |
| Phe | Asp | Arg | Ala | Ala | Asp | Gly | Phe | Phe | Ala | Gly | Glu | Gly | Cys | Gly | Ala |
| | | | 260 | | | | | 265 | | | | | 270 | | |
| Leu | Val | Phe | Lys | Arg | Leu | Thr | Asp | Cys | Val | Ser | Gly | Glu | Arg | Ile | Tyr |
| | | | | 275 | | | | | 280 | | | | | 285 | |
| Ala | Ser | Leu | Asp | Ser | Val | Val | Ala | Thr | Thr | Pro | Arg | Ala | Ala | Leu |
| | 290 | | | | | 295 | | | | | 300 | | | | |
| Arg | Ala | Ala | Ala | Gly | Ser | Ala | Arg | Val | Asp | Pro | Ala | Ser | Ile | Asp | Met |
| 305 | | | | | 310 | | | | | 315 | | | | | 320 |
| Val | Glu | Leu | Ser | Ala | Asp | Ser | His | Arg | Phe | Val | Arg | Ala | Pro | Gly | Thr |
| | | | | 325 | | | | | 330 | | | | | 335 | |

| | | | | | | | | | | | | |
|---|---|---|---|---|---|---|---|---|---|---|---|---|
|Val|Ala|Gln|Pro|Leu|Thr|Ala|Glu|Val|Glu|Val|Gly|Ala|Val|Arg|Glu|
| | | |340| | | |345| | | |350| |
|Val|Ile|Gly|Thr|Ala|Gly|Arg|Gly|Ser|Arg|Ser|Val|Ala|Val|Gly|Ser|
| | | |355| | | |360| | | |365| |
|Val|Arg|Ala|Asn|Val|Gly|Asp|Ala|Gly|Phe|Ala|Ser|Gly|Ala|Ala|Ala|
| | | |370| | | |375| | | |380| |
|Leu|Val|Lys|Thr|Ala|Leu|Cys|Leu|His|Asn|Arg|Tyr|Leu|Ala|Ala|Thr|
|385| | | |390| | | |395| | | |400|
|Pro|Gly|Trp|Asp|Ala|Pro|Ala|Ala|Gly|Val|Asp|Phe|Gly|Ala|Glu|Leu|
| | | |405| | | |410| | | |415| |
|Tyr|Val|Cys|Arg|Glu|Ser|Arg|Ala|Trp|Val|Lys|Asn|Ala|Gly|Val|Ala|
| | | |420| | | |425| | | |430| |
|Arg|His|Ala|Ala|Ile|Ser|Gly|Val|Asp|Glu|Gly|Gly|Ser|
| | | |435| | | |440| | | |445|

<210> SEQ ID NO 24
<211> LENGTH: 1488
<212> TYPE: DNA
<213> ORGANISM: T. aureum

<400> SEQUENCE: 24

| | | | | |
|---|---|---|---|---|
|tgctatgggc|tggttctttc|ggacgtgcct|gggcagtacg|agaccggcaa ccgcatctcc|60|
|ctccaggccg|agtcgcccaa|gctcttgctc|ctctcggctc|agaccacgc cgccttgctg|120|
|gacaaggtgg|cggccgagct|cgcagccctt|gagcaagccg|acggcttgag cgccgccgcg|180|
|gctgccgtag|accgcttact|cggcgagtcg|ctcgtcggtt|gcgcggctgg cagcggcggg|240|
|ctgaccctt|gcttggtggc|ttcgcctgcc|agcctccaca|aggagcttgc gctggcccat|300|
|cgagggatcc|cgcgctgcat|caaagcacg|cgcgactggg|ccagcccggc agggagctac|360|
|ttcgccccgg|agccgatcgc|aagcgaccgc|gtcgcgttca|tgtacgggga aggacgaagc|420|
|ccgtactgcg|cgctcggccg|cgacctccac|cggatctggc|ccgcgctgca tgagcgggtg|480|
|aacgccaaga|ctgtcaacct|ctggggtgac|ggtgacgcct|ggctgctgcc acgtgcaacc|540|
|tcggccgaga|agaggagca|actctgccgc|aacttcgact|cgaaccaggt tgagatgttt|600|
|cgaacgggcg|tgtacatctc|gatgtgcttg|accgacctcg|ctcgaagctt gattggactg|660|
|ggccctaagg|cgagctttgg|gctcagccta|ggcgaggttt|ccatgctctt cgctctgagc|720|
|gagtccaact|gtagactgtc|ggaggaaatg|acccgcaggc|tccgtgcgtc cccggtgtgg|780|
|aactcggagc|tcgccgtcga|gttcaacgcc|cttcgaaagt|tgtgggggt cgcgccgggg|840|
|gcacccgtcg|actcgttctg|gcaaggttat|gtcgtgcgcg|caacgcgggc tcaggtggag|900|
|caagccattg|gggaggacaa|tcagtttgtg|cgtctcctga|tcgtgaacga ctcgcaatca|960|
|gtcctgatcg|ccggcaagcc|ggcggcgtgc|gaagccgtaa|ttgctcgcat cgggtctatt|1020|
|cttccccgc|tgcaagtgtc|gcaaggcatg|gtggggcact|gtgccgaggt cttgccgtac|1080|
|acgagcgaga|tcgggcgcat|ccacaacatg|cttcgcttcc|catcgcagga cgaaacgggc|1140|
|ggttgcaaaa|tgtactctag|cgtctcaaac|tcgcgcatcg|gccagtcga ggagagccag|1200|
|atgggcccag|gcactgagct|cgtttttctcg|ccgtcaatgg|aagactttgt cgcccagctg|1260|
|tactcgcgag|ttgcagactt|tccggcgatc|accgaggcgg|tttaccagca gggtcatgac|1320|
|gtgtttgtcg|aagtggggcc|ggaccattca|cggtcggctg|ctgtccgctc cacgcttgga|1380|
|cccactcggc|gacacatcgc|tgtggcgatg|gaccgcaagg|gtgagtcagc ttggtcgcag|1440|
|cttctgaaaa|tgctggctac|gcttgcgtcg|caccgcgtgc|cgggcctg|1488|

<210> SEQ ID NO 25
<211> LENGTH: 496
<212> TYPE: PRT
<213> ORGANISM: T. aureum

<400> SEQUENCE: 25

```
Cys Tyr Gly Leu Val Leu Ser Asp Val Pro Gly Gln Tyr Glu Thr Gly
  1               5                  10                  15

Asn Arg Ile Ser Leu Gln Ala Glu Ser Pro Lys Leu Leu Leu Leu Ser
             20                  25                  30

Ala Pro Asp His Ala Ala Leu Leu Asp Lys Val Ala Ala Glu Leu Ala
         35                  40                  45

Ala Leu Glu Gln Ala Asp Gly Leu Ser Ala Ala Ala Ala Val Asp
 50                  55                  60

Arg Leu Leu Gly Glu Ser Leu Val Gly Cys Ala Ala Gly Ser Gly Gly
 65                  70                  75                  80

Leu Thr Leu Cys Leu Val Ala Ser Pro Ala Ser Leu His Lys Glu Leu
                 85                  90                  95

Ala Leu Ala His Arg Gly Ile Pro Arg Cys Ile Lys Ala Arg Arg Asp
            100                 105                 110

Trp Ala Ser Pro Ala Gly Ser Tyr Phe Ala Pro Glu Pro Ile Ala Ser
        115                 120                 125

Asp Arg Val Ala Phe Met Tyr Gly Glu Gly Arg Ser Pro Tyr Cys Gly
    130                 135                 140

Val Gly Arg Asp Leu His Arg Ile Trp Pro Ala Leu His Glu Arg Val
145                 150                 155                 160

Asn Ala Lys Thr Val Asn Leu Trp Gly Asp Gly Asp Ala Trp Leu Leu
                165                 170                 175

Pro Arg Ala Thr Ser Ala Glu Glu Glu Gln Leu Cys Arg Asn Phe
            180                 185                 190

Asp Ser Asn Gln Val Glu Met Phe Arg Thr Gly Val Tyr Ile Ser Met
        195                 200                 205

Cys Leu Thr Asp Leu Ala Arg Ser Leu Ile Gly Leu Gly Pro Lys Ala
    210                 215                 220

Ser Phe Gly Leu Ser Leu Gly Glu Val Ser Met Leu Phe Ala Leu Ser
225                 230                 235                 240

Glu Ser Asn Cys Arg Leu Ser Glu Glu Met Thr Arg Arg Leu Arg Ala
                245                 250                 255

Ser Pro Val Trp Asn Ser Glu Leu Ala Val Glu Phe Asn Ala Leu Arg
            260                 265                 270

Lys Leu Trp Gly Val Ala Pro Gly Ala Pro Val Asp Ser Phe Trp Gln
        275                 280                 285

Gly Tyr Val Val Arg Ala Thr Arg Ala Gln Val Glu Gln Ala Ile Gly
    290                 295                 300

Glu Asp Asn Gln Phe Val Arg Leu Leu Ile Val Asn Asp Ser Gln Ser
305                 310                 315                 320

Val Leu Ile Ala Gly Lys Pro Ala Ala Cys Glu Ala Val Ile Ala Arg
                325                 330                 335

Ile Gly Ser Ile Leu Pro Leu Gln Val Ser Gln Gly Met Val Gly
            340                 345                 350

His Cys Ala Glu Val Leu Pro Tyr Thr Ser Ile Gly Arg Ile His
        355                 360                 365

Asn Met Leu Arg Phe Pro Ser Gln Asp Glu Thr Gly Gly Cys Lys Met
    370                 375                 380

Tyr Ser Ser Val Ser Asn Ser Arg Ile Gly Pro Val Glu Glu Ser Gln
```

|  |  |  | 385 |  |  |  | 390 |  |  |  | 395 |  |  |  | 400 |
|---|---|---|---|---|---|---|---|---|---|---|---|---|---|---|---|
| Met | Gly | Pro | Gly | Thr | Glu | Leu | Val | Phe | Ser | Pro | Ser | Met | Glu | Asp | Phe |

Val Ala Gln Leu Tyr Ser Arg Val Ala Asp Phe Pro Ala Ile Thr Glu
                420                        425                    430

Ala Val Tyr Gln Gln Gly His Asp Val Phe Val Glu Val Gly Pro Asp
        435                      440                      445

His Ser Arg Ser Ala Ala Val Arg Ser Thr Leu Gly Pro Thr Arg Arg
    450                          455                      460

His Ile Ala Val Ala Met Asp Arg Lys Gly Glu Ser Ala Trp Ser Gln
465                      470                      475                      480

Leu Leu Lys Met Leu Ala Thr Leu Ala Ser His Arg Val Pro Gly Leu
                485                        490                      495

<210> SEQ ID NO 26
<211> LENGTH: 1683
<212> TYPE: DNA
<213> ORGANISM: T. aureum

<400> SEQUENCE: 26

| gcgaccatcc | ctgaggccgt | cgcaacaatt | ctgccggcaa | ctgctgcgat | ttcgcctcca | 60 |
|---|---|---|---|---|---|---|
| aagcttggcg | ctccgcacga | ctcgcaaccc | gaggcggagg | ctcgcccgt | gggcgaggcc | 120 |
| tctgtgccaa | ggcgggccac | gagctcgagc | aaattggcca | ggacgcttgc | catcgatgct | 180 |
| tgcgactccg | acgtgcgcgc | cgccttgctg | gacctggacg | cgccaatcgc | ggtcggcggc | 240 |
| tcctcgcgcg | cccaagtccc | gccgtgccca | gtgagcgcgc | tcggaagcgc | cgcctttcga | 300 |
| gcggcacacg | cgtcgatta | tcgctctac | atgggcgcaa | tggccaaagg | cgtcgcgtca | 360 |
| gcggagatgg | tcatcgctgc | tggcaaggcc | cgcatgctcg | cgtcatttgg | cgcggggggg | 420 |
| cttcccctgg | gcgaggtcga | agaggcgttg | acaagatcc | aggccgctct | gcccgagggg | 480 |
| ccgttcgccg | tcaacctcat | tcactcgccg | ttcgatccaa | accttgagga | gggcaacgtc | 540 |
| gagctgttcc | tgaggcgcgg | tatccggctg | gtcgaggcct | ctgcgttcat | gtcggtcacg | 600 |
| ccgtcgttgg | tgcgctaccg | agtcgccgga | ctcgagcgag | gccctggcgg | gaccgcccga | 660 |
| gtgctgaacc | gcgtgattgg | caaggtgagc | cgtgcggagc | tcgcagaaat | gtttatgcgg | 720 |
| ccgcctcccg | ccgcgatcgt | ctccaagctc | ctcgcccagg | gcctggtcac | tgaggagcag | 780 |
| gcgtcacttg | cagagatcgt | cccactggtt | gacgacgttg | caatcgaagc | cgactcgggc | 840 |
| ggtcacacag | acaaccgccc | gatccacgtc | gttttgcccg | tcgtcctcgc | gctgcgagac | 900 |
| cgcgtcatgc | gtgagtgcaa | gtatccagcc | gccaatcgcg | tccgcgtggg | cgccggaggc | 960 |
| gggatcggct | gccctgccgc | ggcgcgagct | cgttcgaca | tgggcgcagc | attcgttctc | 1020 |
| acgggctcga | tcaaccagct | cacgcgccag | gctgggacga | gcgacagcgt | gcgtgctgcc | 1080 |
| cttgcacgcg | cgacctactc | ggacgtgaca | atgcccccgg | cggccgatat | gtttgaccag | 1140 |
| ggcgtcaagc | tgcaggtctt | gaagcgcggc | acgatgttcc | cggcgcgcgc | aaacaagctg | 1200 |
| tacgagttgt | tcaccactta | ccagtcgctg | gacgcgatcc | ctcgggctga | gctggctcgc | 1260 |
| ctggaaaagc | gagttttccg | catgtccatc | gacgaggttt | ggaacgaaac | caagcagttc | 1320 |
| tacgagaccc | ggctcaacaa | ccccgccaag | gttgcccggg | cggagcgcga | ccccaagctc | 1380 |
| aagatgtcgc | tctgctttcg | gtggtacttg | tcgaaaagct | ccaagtgggc | atcgactgga | 1440 |
| caagttgggc | gcgagctgga | ctaccaggtc | tggtgcggcc | ccacgattgg | cgcttcaac | 1500 |
| gagttcgtga | aggggtccag | cctcgacgcg | gaggcttgcg | ggggcggtt | tccttgcgtt | 1560 |

```
gtgcgcgtta accaggagat attatgtggc gctgcttacg agcagcgact ggcgcgtttc      1620
atgctgctcg ctggccggga aagcgcggac gcgttggcgt acacggttgc ggaagccaga      1680
tag                                                                    1683
```

<210> SEQ ID NO 27
<211> LENGTH: 560
<212> TYPE: PRT
<213> ORGANISM: T. aureum

<400> SEQUENCE: 27

```
Ala Thr Ile Pro Glu Ala Val Ala Thr Ile Leu Pro Ala Thr Ala Ala
 1               5                  10                  15

Ile Ser Pro Pro Lys Leu Gly Ala Pro His Asp Ser Gln Pro Glu Ala
            20                  25                  30

Glu Ala Arg Pro Val Gly Glu Ala Ser Val Pro Arg Ala Thr Ser
        35                  40                  45

Ser Ser Lys Leu Ala Arg Thr Leu Ala Ile Asp Ala Cys Asp Ser Asp
    50                  55                  60

Val Arg Ala Ala Leu Leu Asp Leu Asp Ala Pro Ile Ala Val Gly Gly
65                  70                  75                  80

Ser Ser Arg Ala Gln Val Pro Pro Cys Pro Val Ser Ala Leu Gly Ser
                85                  90                  95

Ala Ala Phe Arg Ala Ala His Gly Val Asp Tyr Ala Leu Tyr Met Gly
            100                 105                 110

Ala Met Ala Lys Gly Val Ala Ser Ala Glu Met Val Ile Ala Ala Gly
        115                 120                 125

Lys Ala Arg Met Leu Ala Ser Phe Gly Ala Gly Gly Leu Pro Leu Gly
    130                 135                 140

Glu Val Glu Glu Ala Leu Asp Lys Ile Gln Ala Ala Leu Pro Glu Gly
145                 150                 155                 160

Pro Phe Ala Val Asn Leu Ile His Ser Pro Phe Asp Pro Asn Leu Glu
                165                 170                 175

Glu Gly Asn Val Glu Leu Phe Leu Arg Arg Gly Ile Arg Leu Val Glu
            180                 185                 190

Ala Ser Ala Phe Met Ser Val Thr Pro Ser Leu Val Arg Tyr Arg Val
        195                 200                 205

Ala Gly Leu Glu Arg Gly Pro Gly Gly Thr Ala Arg Val Leu Asn Arg
    210                 215                 220

Val Ile Gly Lys Val Ser Arg Ala Glu Leu Ala Glu Met Phe Met Arg
225                 230                 235                 240

Pro Pro Pro Ala Ala Ile Val Ser Lys Leu Leu Ala Gln Gly Leu Val
                245                 250                 255

Thr Glu Glu Gln Ala Ser Leu Ala Glu Ile Val Pro Leu Val Asp Asp
            260                 265                 270

Val Ala Ile Glu Ala Asp Ser Gly Gly His Thr Asp Asn Arg Pro Ile
        275                 280                 285

His Val Val Leu Pro Val Val Leu Ala Leu Arg Asp Arg Val Met Arg
    290                 295                 300

Glu Cys Lys Tyr Pro Ala Ala Asn Arg Val Arg Val Gly Ala Gly Gly
305                 310                 315                 320

Gly Ile Gly Cys Pro Ala Ala Arg Ala Ala Phe Asp Met Gly Ala
                325                 330                 335

Ala Phe Val Leu Thr Gly Ser Ile Asn Gln Leu Thr Arg Gln Ala Gly
            340                 345                 350
```

-continued

```
Thr Ser Asp Ser Val Arg Ala Ala Leu Ala Arg Ala Thr Tyr Ser Asp
        355                 360                 365

Val Thr Met Ala Pro Ala Ala Asp Met Phe Asp Gln Gly Val Lys Leu
        370                 375                 380

Gln Val Leu Lys Arg Gly Thr Met Phe Pro Ala Arg Ala Asn Lys Leu
385                 390                 395                 400

Tyr Glu Leu Phe Thr Thr Tyr Gln Ser Leu Asp Ala Ile Pro Arg Ala
                405                 410                 415

Glu Leu Ala Arg Leu Glu Lys Arg Val Phe Arg Met Ser Ile Asp Glu
                420                 425                 430

Val Trp Asn Glu Thr Lys Gln Phe Tyr Glu Thr Arg Leu Asn Asn Pro
        435                 440                 445

Ala Lys Val Ala Arg Ala Glu Arg Asp Pro Lys Leu Lys Met Ser Leu
        450                 455                 460

Cys Phe Arg Trp Tyr Leu Ser Lys Ser Ser Lys Trp Ala Ser Thr Gly
465                 470                 475                 480

Gln Val Gly Arg Glu Leu Asp Tyr Gln Val Trp Cys Gly Pro Thr Ile
                485                 490                 495

Gly Ala Phe Asn Glu Phe Val Lys Gly Ser Ser Leu Asp Ala Glu Ala
                500                 505                 510

Cys Gly Gly Arg Phe Pro Cys Val Val Arg Val Asn Gln Glu Ile Leu
        515                 520                 525

Cys Gly Ala Ala Tyr Glu Gln Arg Leu Ala Arg Phe Met Leu Leu Ala
        530                 535                 540

Gly Arg Glu Ser Ala Asp Ala Leu Ala Tyr Thr Val Ala Glu Ala Arg
545                 550                 555                 560
```

The invention claimed is:

1. An isolated nucleic acid having a sequence of nucleotides comprising or complementary to a nucleic acid sequence encoding a polypeptide having polyketide synthase activity with a substrate selected from the group consisting of acetyl-CoA, malonyl-CoA, and methylmalonyl-CoA, wherein the amino acid sequence of said polypeptide has at least 95% amino acid sequence identity to the amino acid sequence set forth in SEQ ID NO:10.

2. An isolated nucleic acid sequence having a sequence of nucleotides comprising or complementary to a nucleic acid sequence having at least 90% nucleotide sequence identity to the nucleic acid sequence set forth in SEQ ID NO:8, wherein said isolated nucleic acid sequence encodes a polypeptide having polyketide synthase activity with a substrate selected from the group consisting of acetyl-CoA, malonyl-CoA, and methyl malonyl-CoA.

3. The isolated nucleic acid sequence of claim 1, wherein said polyketide synthase permits the production of at least one polyunsaturated fatty acid when expressed in a host cell.

4. The isolated nucleic acid sequence of claim 3, wherein said at least one polyunsaturated fatty acid is selected from the group consisting of eicosapentaenoic acid and docosahexaenoic acid.

5. The isolated nucleic acid sequence of claim 1 wherein said sequence is isolated from *Thraustochytrium* sp.

6. The isolated nucleic acid sequence of claim 5 wherein said sequence is isolated from *Thraustochytrium aureum*.

7. A method of producing a polyketide synthase comprising:
   a) isolating a nucleic acid sequence comprising SEQ ID NO:8;
   b) constructing a vector comprising said isolated nucleic acid sequence operably linked to a regulatory sequence; and
   c) introducing said vector into an isolated a host cell for a time and under conditions sufficient for expression of said polyketide synthase, whereby said polyketide synthase is produced.

8. The method of claim 7 wherein said host cell is selected from the group consisting of an eukaryotic cell and a prokaryotic cell.

9. A vector comprising a nucleic sequence comprising SEQ ID NO:8, operably linked to a regulatory sequence.

10. An isolated host cell comprising the vector of claim 9.

11. The host cell of claim 10 wherein said host cell is selected from the group consisting of an eukaryotic cell and a prokaryotic cell.

12. A method for producing a polyunsaturated fatty acid comprising:
   a) isolating a nucleic acid sequence comprising SEQ ID NO:8;
   b) constructing a vector comprising said isolated nucleic acid sequence operably linked to a regulatory sequence;
   c) introducing said vector into an isolated host cell for a time and under conditions sufficient for expression of the polyketide synthase encoded by said isolated nucleic sequence;
   d) exposing said polyketide synthase to a substrate selected from the group consisting of acetyl-CoA, malonyl-CoA, and methylmalonyl-CoA, to produce an acyl-chain intermediate product; and e) exposing said acyl-chain intermediate product to at least one enzyme selected from the group consisting of a ketosynthase, a ketoreductase, a dehydratase, an isomerase, an enoyl reductase, a desaturase, and an elongase, whereby said said polyunsaturated fatty acid is produced.

13. The method of claim 12, wherein said polyunsaturated fatty acid is selected from the group consisting of eicosapentaenoic acid (EPA) and docosahexaenoic acid (DHA).

* * * * *